United States Patent
Demarcq et al.

(10) Patent No.: US 11,304,881 B2
(45) Date of Patent: Apr. 19, 2022

(54) COMPOSITION BASED ON AN AQUEOUS PHASE CONTAINING A DISPERSION OF AN ANHYDROUS COMPOSITE MATERIAL

(71) Applicant: L'OREAL, Paris (FR)

(72) Inventors: Céline Demarcq, Gigors-et-Lozeron (FR); Noémie Pioud, Gigors-et-Lozeron (FR); Emmanuelle Camblong, Gigors-et-Lozeron (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/060,833

(22) PCT Filed: Dec. 16, 2016

(86) PCT No.: PCT/EP2016/081396
§ 371 (c)(1),
(2) Date: Jun. 8, 2018

(87) PCT Pub. No.: WO2017/103083
PCT Pub. Date: Jun. 22, 2017

(65) Prior Publication Data
US 2018/0360702 A1    Dec. 20, 2018

(30) Foreign Application Priority Data
Dec. 18, 2015  (FR) ...................... 1562831

(51) Int. Cl.
*A61K 8/04* (2006.01)
*A61K 8/25* (2006.01)
*A61K 8/31* (2006.01)
*A61K 8/37* (2006.01)
*A61K 8/44* (2006.01)
*A61Q 1/02* (2006.01)
*A61K 8/73* (2006.01)
*A61K 8/81* (2006.01)
*A61K 8/34* (2006.01)
*A61K 8/92* (2006.01)

(52) U.S. Cl.
CPC .............. *A61K 8/042* (2013.01); *A61K 8/044* (2013.01); *A61K 8/25* (2013.01); *A61K 8/31* (2013.01); *A61K 8/34* (2013.01); *A61K 8/375* (2013.01); *A61K 8/44* (2013.01); *A61K 8/731* (2013.01); *A61K 8/732* (2013.01); *A61K 8/8158* (2013.01); *A61K 8/92* (2013.01); *A61K 8/922* (2013.01); *A61Q 1/02* (2013.01); *A61K 2800/412* (2013.01)

(58) Field of Classification Search
None
See application file for complete search history.

(56) References Cited

U.S. PATENT DOCUMENTS

| | | | |
|---|---|---|---|
| 3,301,848 A | 1/1967 | Halleck | |
| 3,589,578 A | 6/1971 | Kamphausen | |
| 3,915,921 A | 10/1975 | Schlatzer, Jr. | |
| 4,031,307 A | 6/1977 | DeMartino et al. | |
| 4,509,949 A | 4/1985 | Huang et al. | |
| 2004/0096472 A1* | 5/2004 | Tournilhac | A61K 8/31 424/401 |
| 2014/0335136 A1* | 11/2014 | Brieva | A61K 8/585 424/401 |

FOREIGN PATENT DOCUMENTS

| | | |
|---|---|---|
| EP | 0216479 A1 | 4/1987 |
| EP | 0815928 A2 | 1/1988 |
| FR | 2843020 A1 | 2/2004 |
| WO | 2014128678 A1 | 8/2014 |
| WO | 2014128679 A1 | 8/2014 |
| WO | 2014128680 A1 | 8/2014 |
| WO | WO 2014/128680 * | 8/2014 |
| WO | 2014167543 A1 | 10/2014 |
| WO | 2015181733 | 3/2015 |
| WO | 2016001577 A1 | 1/2016 |
| WO | 2016001578 A1 | 1/2016 |

* cited by examiner

*Primary Examiner* — Shirley V Gembeh
(74) *Attorney, Agent, or Firm* — McNees Wallace & Nurick LLC

(57) ABSTRACT

The present invention relates to a composition, especially for caring for and/or making up keratin materials, comprising at least one aqueous phase containing at least one hydrophilic gelling agent, and a dispersion of at least one anhydrous composite material formed from at least:
- 3% to 15% by weight of at least one lipophilic gelling agent, relative to the total weight of the material;
- 10% to 50% by weight of fillers, relative to the total weight of the material; and
- 40% to 85% by weight of at least one fatty phase, relative to the total weight of the material.

The invention also relates to a cosmetic process for making up and/or caring for a keratin material, in particular the skin, comprising at least one step that consists in applying to said keratin material a composition as defined above.

27 Claims, No Drawings

COMPOSITION BASED ON AN AQUEOUS PHASE CONTAINING A DISPERSION OF AN ANHYDROUS COMPOSITE MATERIAL

The present invention relates to the cosmetic field, and in particular the field of caring for and/or making up keratin materials, especially the skin, the lips, the hair or the nails, preferably the skin.

In the field of cosmetic compositions for caring for and/or making up the skin, it is known practice to use mineral or organic fillers with a soft-focus effect which absorb fat, give an astounding "photoshop" optical effect, and also a very soft feel, for making the skin matt, and/or for optically smoothing the microrelief, filling wrinkles, hiding skin imperfections and better reflecting light.

Unfortunately, the use of such fillers may be accompanied by a dry, coarse feel, fluffing, white marks and a lack of comfort that are offputting to the user.

In order to overcome this problem and to afford comfortable care that has a soft-focus effect, alternative oily presentation forms are currently proposed on the cosmetic market.

However, these formulations have the drawbacks associated with the presence of large contents of fatty phase in the composition, namely producing shiny skin and/or the sensation of greasy and/or tacky skin.

The use of crosslinked silicones is another alternative. The reason for this is that starting materials of this type can combine a matt effect and a soft-focus effect. However, they have the drawback of being characterized by a relatively uncomfortable warm and greasy feel, with a "mask" effect.

Thus, it remains difficult to reconcile in the same composition opposing technical performance qualities, for instance a matt result (which may make the skin dry) and moisturization (which may make the skin shiny).

It thus remains difficult for a person skilled in the art to develop homogeneous compositions that are capable of affording an immediate visual result on the skin with a sensation of lightness and comfort on application, this expected immediate result preferentially being good covering of color imperfections and/or relief imperfections.

There also remains a need for cosmetic formulations, which are more particularly intended for caring for and/or making up facial skin, which are capable of rendering the skin microrelief optically matt and/or smooth, filling wrinkles, hiding skin imperfections and better reflecting light, while at the same time being capable of affording a pleasant feel especially when applied, and a very soft skin finish with no "mask" effect, and which allow the skin to breathe.

The object of the present invention is, precisely, to satisfy these expectations.

Thus, according to a first of its aspects, the present invention relates to a composition, especially for caring for and/or making up keratin materials, comprising at least one aqueous phase containing at least:
  a hydrophilic gelling agent; and
  a dispersion of at least one anhydrous composite material formed from at least:
    3% to 15% by weight of at least one lipophilic gelling agent, relative to the total weight of the material;
    10% to 50% by weight of fillers, relative to the total weight of the material; and
    40% to 85% by weight of at least one fatty phase, relative to the total weight of the material.

It is understood that the amount of fatty phase in the anhydrous composite material does not comprise the content of lipophilic gelling agent(s) included in this same material.

According to a preferred embodiment, a composition according to the invention comprises a weight ratio of anhydrous composite material/hydrophilic gelling agent(s) ranging from 0.2 to 30, in particular from 0.5 to 28, preferably from 0.6 to 21 and better still from 0.6 to 10.

Advantageously, the hydrophilic gelling agent is chosen from polysaccharides, in particular non-starchy polysaccharides, and non-particulate synthetic polymeric gelling agents, in particular 2-acrylamido-2-methylpropanesulfonic acid polymers and copolymers, and mixtures thereof, and preferably from xanthans, galactans, in particular carrageenans, celluloses and derivatives thereof, and 2-acrylamido-2-methylpropanesulfonic acid polymers and copolymers, and mixtures thereof.

According to a preferred embodiment of the invention, such hydrophilic gelling agents are used in the aqueous phase with a dispersion of an anhydrous composite material formed from at least:
  3% to 15% by weight, relative to the total weight of the material, of at least one lipophilic gelling agent chosen from triesters of a $C_8$-$C_{30}$ fatty acid and of mono- or polyglycerol, such as glyceryl trihydroxystearate;
  10% to 50% by weight of fillers, relative to the total weight of the material, including at least 5% by weight of a first filler chosen from spherical porous silica microparticles and spherical cellulose particles, and at least 5% by weight of a second filler different from the first, chosen from spherical cellulose particles; and
  40% to 85% by weight of at least one fatty phase, relative to the total weight of the material, comprising from 25% to 58% by weight, relative to the total weight of the material, of at least one oil chosen from hydrocarbon-based oils, preferably triglycerides, and from 5% to 10% by weight of at least one oil chosen from linear $C_7$-$C_{17}$ alkanes.

The term "keratin materials" especially means the skin, the lips, the eyebrows and/or the eyelashes, in particular the skin and/or the eyebrows, preferably the skin and especially facial skin.

Contrary to all expectation, the inventors have discovered that the use, in a composition, of an aqueous phase comprising a hydrophilic gelling agent combined with a dispersion of a specific anhydrous composite material comprising a fatty phase, a lipophilic gelling agent and fillers, in suitable amounts, makes it possible to satisfy the problem mentioned above. This composition has a presentation form endowed with a novel sensory effect both on application and on the skin finish, without, however, neglecting the cosmetic qualities.

Thus, the present invention makes it possible to obtain a novel presentation form that is most particularly advantageous with regard to its technical performance qualities and the sensory results it affords the user when it is applied to keratin materials, and in particular to the skin.

In particular, the composition in accordance with the invention affords comfortable care with a soft-focus effect, i.e. it can render the skin microrelief optically matt and/or smooth, fill wrinkles, hide skin imperfections and better reflect light, while at the same time giving a pleasant feel and a novel sensory effect, with powdery transformation especially when it is applied, with a velvety skin finish, and which allows the skin to breathe.

The comfort on application is reflected especially by an absence of tautness, of dryness sensations and/or of tacky and/or greasy sensations.

The composition according to the invention is stable, especially over time and/or with respect to temperature variations, while at the same time having good cosmetic and sensory properties.

The term "stable" means stable at room temperature (25° C.) for at least 1 month, preferably for at least 2 months.

It affords all the benefits of a serum, especially a very light texture and easy application, and/or of a conventional oily presentation form, without having the greasy feel or the shiny appearance thereof. The skin finish is homogeneous and comfortable.

The composition is friendly to the skin, it is pleasant and does not leave the skin greasy or tacky. The texture is soft and pleasant, and the composition is easy to take up. It affords an optical and tactile effect for immediately correcting the surface appearance of the skin, by attenuating the shadow areas of the skin relief such as wrinkles, fine lines, dilated pores and other skin imperfections. It fades out the signs of fatigue. It smooths and refines the skin grain, restoring the skin's radiance and freshness, for a natural result.

WO 2014/128680, WO 2014/167543, WO 2014/128679 and WO 2014/128678 describes cosmetic compositions comprising a gelled aqueous phase and a gelled lipophilic phase, said phases forming a macroscopically homogeneous mixture. In other word, these documents focus on the interpenetration of a gelled aqueous phase and a gelled oily phase, in order to form a stable and consistent product, by mixing interpenetrated macrodomains. Accordingly, such documents do not describe a dispersion of an anhydrous composite material in an aqueous phase, as achieved with the instant invention.

FR 2 843 020 also concerns cosmetic compositions, which contain esters of dextrin. Nonetheless, as for the above mentioned documents, it does not relate to specific galenic as considered in the present invention.

According to another aspect, a subject of the present invention is also a cosmetic process for making up and/or caring for a keratin material, in particular the skin, comprising at least one step that consists in applying to said keratin material a composition as defined above.

Aqueous Phase

As indicated previously, a composition according to the invention comprises at least one aqueous phase, this aqueous phase conveying at least one hydrophilic gelling agent and a dispersion of at least one specific anhydrous composite material. More precisely, this material is formed from at least one lipophilic gelling agent, fillers and a fatty phase.

In particular, the aqueous phase is present in a content at least equal to 40% by weight, preferably at least equal to 70% by weight, even more preferentially between 70% and 85% by weight and better still between 75% and 85% by weight, relative to the total weight of the composition.

Hydrophilic Gelling Agent

For the purposes of the present invention, the term "hydrophilic gelling agent" means a compound that is capable of gelling the aqueous phase of the compositions according to the invention.

The gelling agent is hydrophilic and is thus, in this respect, present in the aqueous phase of the composition. The gelling agent may be water-soluble or water-dispersible.

In particular, a composition according to the invention comprises from 0.01% to 10% by weight, preferably from 0.1% to 3% by weight, more preferentially from 0.5% to 2.5% by weight, and better still from 1.5% to 2.2% by weight of hydrophilic gelling agent(s), relative to the total weight of the composition.

The hydrophilic gelling agent may be chosen from synthetic polymeric gelling agents, polymeric gelling agents that are natural or of natural origin, mixed silicates and fumed silicas, and mixtures thereof.

Preferably, the hydrophilic gelling agent is chosen from polymeric gelling agents that are natural or of natural origin and synthetic polymeric gelling agents, and mixtures thereof.

Even more preferentially, the hydrophilic gelling agent is chosen from polysaccharides, in particular non-starchy polysaccharides, and non-particulate synthetic polymeric gelling agents, in particular 2-acrylamido-2-methylpropanesulfonic acid polymers and copolymers, and mixtures thereof.

Even more preferentially, the hydrophilic gelling agent is chosen from xanthans, galactans, in particular carrageenans, celluloses and derivatives thereof, and 2-acrylamido-2-methylpropanesulfonic acid polymers and copolymers, and mixtures thereof.

I. Polymeric Gelling Agents that are Natural or of Natural Origin

The polymeric hydrophilic gelling agents that are suitable for use in the invention may be natural or of natural origin. For the purposes of the invention, the term "of natural origin" is intended to denote polymeric gelling agents obtained by modification of natural polymeric gelling agents.

These gelling agents may be particulate or non-particulate.

More specifically, these gelling agents fall within the category of polysaccharides.

In general, polysaccharides may be divided into several categories.

Thus, the polysaccharides that are suitable for use in the invention may be homopolysaccharides such as fructans, glucans, galactans and mannans or heteropolysaccharides such as hemicellulose. Similarly, they may be linear polysaccharides such as pullulan or branched polysaccharides such as gum arabic and amylopectin, or mixed polysaccharides such as starch. More particularly, the polysaccharides that are suitable for use in the invention may be distinguished according to whether or not they are starchy.

I.A. Starchy Polysaccharides

As representatives of this category, mention may be made most particularly of native starches, modified starches and particulate starches.

Native Starches

The starches that may be used in the present invention are more particularly macromolecules in the form of polymers consisting of elementary moieties which are anhydroglucose units (dextrose), linked via $\alpha(1,4)$ bonds of chemical formula $(C_6H_{10}O_5)_n$. The number of these moieties and their assembly make it possible to distinguish amylose, a molecule formed from about 600 to 1,000 linearly linked glucose molecules, and amylopectin, a polymer branched approximately every 25 glucose residues ($\alpha(1,6)$ bond). The total chain may include between 10 000 and 100 000 glucose residues. Starch is described in particular in Kirk-Othmer's Encyclopaedia of Chemical Technology, 3rd edition, volume 21, pages 492-507, Wiley Interscience, 1983.

The relative proportions of amylose and of amylopectin, and their degree of polymerization, vary as a function of the botanical origin of the starches. On average, a sample of native starch consists of about 25% amylose and 75% amylopectin. Occasionally, phytoglycogen is present (between 0% and 20% of the starch), which is an analog of amylopectin but branched every 10 to 15 glucose residues.

Starch may be in the form of semicrystalline granules: amylopectin is organized in leaflets, amylose forms a less well organized amorphous zone between the various leaflets. Amylose is organized in a straight helix with six glucoses per turn. It dissociates into assimilable glucose under the action of enzymes, amylases, all the more easily when it is in amylopectin form. Specifically, the helical formation does not promote the accessibility of starch to the enzymes.

Starches are generally in the form of a white powder, which is insoluble in cold water, whose elemental particle size ranges from 3 to 100 microns.

By treating it with hot water, starch paste is obtained. It is exploited in industry for its thickening and gelling properties.

The botanical origin of the starch molecules used in the present invention may be cereals or tubers. Thus, the starches are chosen, for example, from corn starch, rice starch, cassava starch, tapioca starch, barley starch, potato starch, wheat starch, sorghum starch and pea starch.

The native starches are represented, for example, by the products sold under the names C*Amilogel™, Cargill Gel™, C*Gel™, Cargill Gum™, DryGel™ and C*Pharm Gel™ by the company Cargill, under the name Corn Starch by the company Roquette, and under the name Tapioca Pure by the company National Starch.

Modified Starches

The modified starches used in the composition of the invention may be modified via one or more of the following reactions: pregelatinization, degradation (acid hydrolysis, oxidation, dextrinization), substitution (esterification, etherification), crosslinking (esterification), bleaching. More particularly, these reactions can be carried out in the following way:

pregelatinization by splitting the starch granules (for example drying and cooking in a drying drum);

acid hydrolysis giving rise to very rapid retrogradation on cooling;

oxidation with strong oxidizing agents (alkaline medium, in the presence of sodium hypochlorite NaOCl for example) leading to the depolymerization of the starch molecule and to the introduction of carboxyl groups into the starch molecule (mainly oxidation of the hydroxyl group at $C_6$);

dextrinization in acid medium at high temperature (hydrolysis followed by repolymerization);

crosslinking with functional agents capable of reacting with the hydroxyl groups of the starch molecules, which will thus bond together (for example with glyceryl and/or phosphate groups);

esterification in alkaline medium for the grafting of functional groups, especially $C_1$-$C_6$ acyl (acetyl), $C_1$-$C_6$ hydroxyalkyl (hydroxyethyl or hydroxypropyl), carboxymethyl or octenylsuccinic.

Monostarch phosphates (of the type St-O—PO—(OX)$_2$), distarch phosphates (of the type St-O—PO—(OX)—O-St) or even tristarch phosphates (of the type St-O—PO—(O-St)$_2$) or mixtures thereof may especially be obtained by crosslinking with phosphorus compounds. X especially denotes alkali metals (for example sodium or potassium), alkaline-earth metals (for example calcium or magnesium), ammonium salts, amine salts, for instance those of monoethanolamine, diethanolamine, triethanolamine, 3-amino-1, 2-propanediol, or ammonium salts derived from basic amino acids such as lysine, arginine, sarcosine, ornithine or citrulline.

The phosphorus compounds can, for example, be sodium tripolyphosphate, sodium orthophosphate, phosphorus oxychloride or sodium trimetaphosphate.

According to the invention, it is also possible to use amphoteric starches, these amphoteric starches containing one or more anionic groups and one or more cationic groups. The anionic and cationic groups may be linked to the same reactive site of the starch molecule or to different reactive sites; they are preferably linked to the same reactive site. The anionic groups may be of carboxylic, phosphate or sulfate type, preferably carboxylic. The cationic groups can be of primary, secondary, tertiary or quaternary amine type. The amphoteric starches are in particular chosen from the compounds having the following formulae:

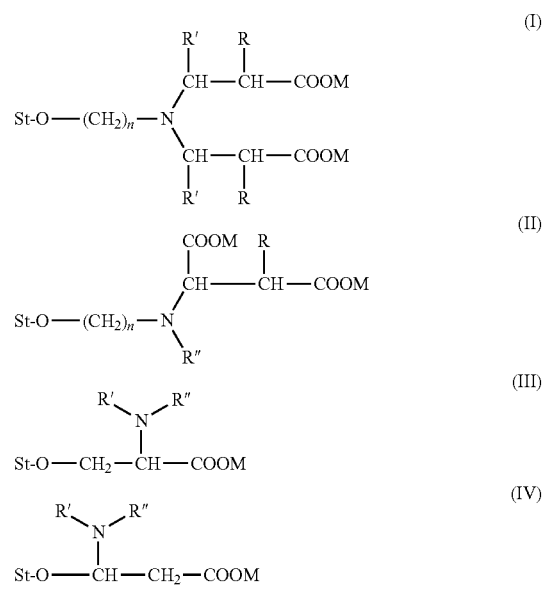

in which:
St-O represents a starch molecule;
R, which may be identical or different, represents a hydrogen atom or a methyl radical;
R', which may be identical or different, represents a hydrogen atom, a methyl radical or a —COOH group;
n is an integer equal to 2 or 3;
M, which may be identical or different, denotes a hydrogen atom, an alkali metal or alkaline-earth metal such as Na, K, Li or NH$_4$, a quaternary ammonium or an organic amine;
R" represents a hydrogen atom or an alkyl radical containing from 1 to 18 carbon atoms.

These compounds are especially described in U.S. Pat. Nos. 5,455,340 and 4,017,460.

The starch molecules may be derived from any plant source of starch, especially such as corn, potato, oat, rice, tapioca, sorghum, barley or wheat. It is also possible to use the hydrolysates of the starches mentioned above.

The modified starches are represented, for example, by the products sold under the names C*Tex-Instant (pregelatinized adipate), C*StabiTex-Instant (pregelatinized phosphate), C*PolarTex-Instant (pregelatinized hydroxypropyl), C*Set (acid hydrolysis, oxidation), C*size (oxidation), C*BatterCrisp (oxidation), C*DrySet (dextrinization), C*Tex™ (acetyl distarch adipate), C*PolarTex™ (hydroxypropyl distarch phosphate), C*StabiTex™ (distarch phosphate, acetyl distarch phosphate) by the company Cargill, by distarch phosphates or compounds rich in distarch phosphate such as the product sold under the references Prejel VA-70-T AGGL (gelatinized hydroxypropyl cassava distarch phosphate) or Prejel TK1 (gelatinized cassava distarch phosphate) or Prejel 200 (gelatinized acetyl cassava distarch phosphate) by the company Avebe or Structure Zea from National Starch (gelatinized corn distarch phosphate).

As examples of oxidized starches, use will be made especially of those sold under the name C*size from the company Cargill.

Particulate Starches

Particulate starches that may be mentioned in particular include:
- starches grafted with an acrylic polymer (homopolymer or copolymer) and especially with sodium polyacrylate, for instance those sold under the names Sanfresh ST100MC by the company Sanyo Chemical Industries or Makimousse 25, Makimousse 12 by the company Daito Kasei (INCI name: Sodium polyacrylate starch),
- hydrolyzed starches grafted with an acrylic polymer (homopolymer or copolymer) and especially acryloacrylamide/sodium acrylate copolymer, for instance those sold under the names Water Lock A-240, A-180, B-204, D-223, A-100, C-200 and D-223 by the company Grain Processing (INCI name: Starch/acrylamide/sodium acrylate copolymer);
- polymers based on starch, gum and cellulose derivative, such as the product containing starch and sodium carboxymethylcellulose, for instance the product sold under the name Lysorb 220 by the company Lysac.

Mention may be made most particularly of $C_1$-$C_4$ carboxyalkyl starches, also referred to hereinbelow as carboxyalkyl starch. These compounds are obtained by grafting carboxyalkyl groups onto one or more alcohol functions of starch, especially by reaction of starch and of sodium monochloroacetate in alkaline medium. The carboxyalkyl groups are generally attached via an ether function, more particularly to carbon 1. The degree of substitution with carboxyalkyl units of the $C_1$-$C_4$ carboxyalkyl starch preferably ranges from 0.1 to 1 and more particularly from 0.15 to 0.5. The degree of substitution is defined according to the present invention as being the mean number of hydroxyl groups substituted with an ester or ether group per monosaccharide unit of the polysaccharide.

The carboxyalkyl starches are advantageously used in the form of salts and especially of salts of alkali metals or alkaline-earth metals such as Na, K, Li, $NH_4$, or salts of a quaternary ammonium or of an organic amine such as monoethanolamine, diethanolamine or triethanolamine. The ($C_1$-$C_4$) carboxyalkyl starches are advantageously, in the context of the present invention, carboxymethyl starches. The carboxymethyl starches preferably comprise units having the following formula:

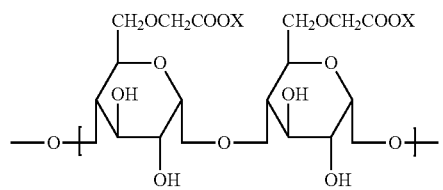

in which X, optionally covalently bonded to the carboxylic unit, denotes a hydrogen atom, an alkali metal or alkaline-earth metal such as Na, K, Li, $NH_4$, a quaternary ammonium or an organic amine, for instance monoethanolamine, diethanolamine or triethanolamine. Preferably, X denotes a cation $Na^+$. The carboxyalkyl starches that may be used according to the present invention are preferably non-pregelatinized carboxyalkyl starches. The carboxyalkyl starches that may be used according to the present invention are preferably partially or totally crosslinked carboxyalkyl starches.

In general, a crosslinked carboxyalkyl starch has, in contrast with a non-crosslinked carboxyalkyl starch, an increased, controllable viscosity of increased stability. The crosslinking thus makes it possible to reduce the syneresis phenomena and to increase the resistance of the gel to shear effects.

The carboxyalkyl starches under consideration according to the invention are more particularly potato carboxyalkyl starches. Thus, the carboxyalkyl starches that may be used according to the present invention are preferably sodium salts of carboxyalkyl starch, in particular a sodium salt of potato carboxymethyl starch, sold especially under the name Primojel® by the company DMV International or Glycolys® and Glycolys® LV by the company Roquette.

According to a particular mode, use will be made of the potato carboxymethyl starches sold especially under the name Glycolys® by the company Roquette. As stated previously, the $C_1$-$C_4$ carboxyalkyl starch particles are present in the compositions according to the invention in a swollen and non-split form. This swelling may be characterized by a swelling power Q which may advantageously be between 10 and 30 ml/g and preferably between 15 and 25 ml (volume of absorbed liquid)/g of dry particulate material.

Thus, the size of the swollen carboxyalkyl starch particles used according to the present invention generally ranges from 25 to 300 μm. For example, the gel Primojel® containing 10% by weight of potato carboxyalkyl starch and sodium salt in water contains more than 80% of swollen particles of this starch with a diameter of greater than 50 microns and more particularly greater than 100 microns.

According to a preferred embodiment variant of the invention, these particles are used for the preparation of the compositions according to the invention, in this swollen particulate state. To do so, these particles are advantageously used in the form of an aqueous gel either prepared beforehand or already commercially available. The gels under consideration according to the invention are advantageously translucent.

For example, a carboxymethyl starch gel such as Primojel® which is at a concentration of 10% by weight may be adjusted to the required concentration before being used for preparing the expected composition.

I.B. Non-Starchy Polysaccharides

According to one embodiment variant, the hydrophilic gelling agent is non-starchy.

In general, the non-starchy polysaccharides may be chosen from polysaccharides produced by microorganisms; polysaccharides isolated from algae, and higher plant polysaccharides, such as homogeneous polysaccharides, in particular celluloses and derivatives thereof or fructosans, heterogeneous polysaccharides such as gum arabics, galactomannans, glucomannans and pectins, and derivatives thereof; and mixtures thereof.

In particular, the polysaccharides may be chosen from fructans, gellans, glucans, amylose, amylopectin, glycogen, pullulan, dextrans, celluloses and derivatives thereof, in particular methylcelluloses, hydroxyalkylcelluloses, ethylhydroxyethylcelluloses and carboxymethylcelluloses, mannans, xylans, lignins, arabans, galactans, galacturonans, alginate-based compounds, chitin, chitosans, glucuronoxylans, arabinoxylans, xyloglucans, glucomannans, pectic acids and pectins, arabinogalactans, carrageenans, agars, glycosaminoglucans, gum arabics, tragacanth gums, ghatti gums, karaya gums, locust bean gums, galactomannans such as guar gums and nonionic derivatives thereof, in particular hydroxypropyl guar, and ionic derivatives thereof, biopolysaccharide gums of microbial origin, in particular scleroglucan or xanthan gums, mucopolysaccharides, and in particular chondroitin sulfates, and mixtures thereof.

These polysaccharides may be chemically modified, especially with urea or urethane groups or by hydrolysis, oxidation, esterification, etherification, sulfation, phosphatation, amination, amidation or alkylation reaction, or by several of these modifications. The derivatives obtained may be anionic, cationic, amphoteric or nonionic.

Advantageously, the polysaccharides may be chosen from carrageenans, in particular kappa carrageenan, gellan gum, agar-agar, xanthan gum, alginate-based compounds, in particular sodium alginate, scleroglucan gum, guar gum, inulin and pullulan, and mixtures thereof.

In general, the compounds of this type that may be used in the present invention are chosen from those described especially in Kirk-Othmer's Encyclopedia of Chemical Technology, Third Edition, 1982, volume 3, pp. 896-900, and volume 15, pp. 439-458, in Polymers in Nature by E. A. MacGregor and C. T. Greenwood, published by John Wiley & Sons, Chapter 6, pp. 240-328, 1980, in the book by Robert L. Davidson entitled Handbook of Water-Soluble Gums and Resins published by McGraw Hill Book Company (1980) and in Industrial Gums—Polysaccharides and their Derivatives, edited by Roy L. Whistler, Second Edition, published by Academic Press Inc.

More precisely, these polysaccharides that are suitable for use in the invention may be distinguished according to whether they are derived from microorganisms, from algae or from higher plants, and are detailed below.

Polysaccharides Produced by Microorganisms

Xanthan

Xanthan is a heteropolysaccharide produced at the industrial scale by the aerobic fermentation of the bacterium *Xanthomonas campestris*. Its structure consists of a main chain of β(1,4)-linked β-D-glucoses, similar to cellulose. One glucose molecule in two bears a trisaccharide side chain composed of an α-D-mannose, a β-D-glucuronic acid and a terminal β-D-mannose. The internal mannose residue is generally acetylated on carbon 6. About 30% of the terminal mannose residues bear a pyruvate group linked in chelated form between carbons 4 and 6. The charged pyruvic acids and glucuronic acids are ionizable, and are thus responsible for the anionic nature of xanthan (negative charge down to a pH equal to 1). The content of pyruvate and acetate residues varies according to the bacterial strain, the fermentation process, the conditions after fermentation and the purification steps. These groups may be neutralized in commercial products with $Na^+$, $K^+$ or $Ca^{2+}$ ions (Satia company, 1986). The neutralized form may be converted into the acid form by ion exchange or by dialysis of an acidic solution.

Xanthan gums have a molecular weight of between 1 000 000 and 50 000 000 and a viscosity of between 0.6 and 1.65 Pa·s for an aqueous composition containing 1% of xanthan gum (measured at 25° C. on a Brookfield viscometer of LVT type at 60 rpm).

Xanthan gums are represented, for example, by the products sold under the names Rhodicare by the company Rhodia Chimie, under the name Satiaxane™ by the company Cargill Texturizing Solutions (for the food, cosmetic and pharmaceutical industries), under the name Novaxan™ by the company ADM, and under the names Kelzan® and Keltrol® by the company CP-Kelco.

Pullulan

Pullulan is a polysaccharide consisting of maltotriose units, known under the name α(1,4)-α(1,6)-glucan. Three glucose units in maltotriose are connected via an α(1,4) glycoside bond, whereas the consecutive maltotriose units are connected to each other via an α(1,6) glycoside bond. Pullulan is produced, for example, under the reference Pullulan PF 20 by the group Hayashibara in Japan.

Dextran and Dextran Sulfate

Dextran is a neutral polysaccharide not bearing any charged groups, which is biologically inert, prepared by fermentation of beet sugar containing solely hydroxyl groups. It is possible to obtain dextran fractions of different molecular weights from native dextran by hydrolysis and purification. Dextran may in particular be in the form of dextran sulfate.

Dextran is represented, for example, by the products sold under the name Dextran or Dextran T by the company Pharmacosmos, or under the name Dextran 40 Powder or Dextran 70 Powder by the company Meito Sangyo Co. Dextran sulfate is sold by the company PK Chemical A/S under the name Dextran sulfate.

Succinoglycan

Succinoglycan is an extracellular polymer of high molecular weight produced by bacterial fermentation, consisting of octasaccharide repeating units (repetition of 8 sugars). Succinoglycans are sold, for example, under the name Rheozan by the company Rhodia.

Scleroglucan

Scleroglucan is a nonionic branched homopolysaccharide consisting of β-D-glucan units. The molecules consist of a linear main chain formed from D-glucose units linked via β(1,3) bonds and of which one in three is linked to a side D-glucose unit via a β(1,6) bond. A more complete description of scleroglucans and of their preparation may be found in U.S. Pat. No. 3,301,848.

Scleroglucan is sold, for example, under the name Amigel by the company Alban Müller, or under the name Actigum™ CS by the company Cargill.

Gellan Gum

Gellan gum is an anionic linear heteropolyoside based on oligoside units composed of 4 saccharides (tetra-oside). D-Glucose, L-rhamnose and D-glucuronic acid in 2:1:1 proportions are present in gellan gum in the form of monomer elements. It is sold, for example, under the name Kelcogel CG LA by the company CP Kelco.

Polysaccharides Isolated from Algae

Galactans

The polysaccharide according to the invention may be a galactan chosen especially from agar and carrageenans. Carrageenans are anionic polysaccharides constituting the cell walls of various red algae (Rhodophyceae) belonging to the Gigartinacae, Hypneaceae, Furcellariaceae and Polyideaceae families. They are generally obtained by hot aqueous extraction from natural strains of said algae. These linear polymers, formed by disaccharide units, are composed of two D-galactopyranose units linked alternately by α(1,3) and β(1,4) bonds. They are highly sulfated polysaccharides (20-50%) and the α-D-galactopyranosyl residues may be in 3,6-anhydro form. Depending on the number and position of sulfate-ester groups on the repeating disaccharide of the molecule, several types of carrageenans are distinguished, namely: kappa-carrageenans, which bear one sulfate-ester group, iota-carrageenans, which bear two sulfate-ester groups, and lambda-carrageenans, which bear three sulfate-ester groups.

Carrageenans are composed essentially of potassium, sodium, magnesium, triethanolamine and/or calcium salts of polysaccharide sulfate esters. Carrageenans are sold especially by the company SEPPIC under the name Solagum®, by the company Gelymar under the names Carragel®, Carralact® and Carrasol®, by the company Cargill, under the names Satiagel™ and Satiagum™, and by the company CP-Kelco under the names Genulacta®, Genugel® and Genuvisco®.

Galactans of agar type are galactose polysaccharides contained in the cell wall of some of these species of red algae (rhodophyceae). They are formed from a polymer group whose base backbone is a β(1,3) D-galactopyranose and α(1,4) L 3-6 anhydrogalactose chain, these units repeating regularly and alternately. The differences within the agar family are due to the presence or absence of solvated methyl or carboxyethyl groups. These hybrid structures are generally present in variable percentage, depending on the species of algae and the harvest season. Agar-agar is a mixture of polysaccharides (agarose and agaropectin) of high molecular mass, between 40 000 and 300 000 g·mol$^{-1}$. It is obtained by manufacturing algal extraction liquors, generally by autoclaving, and by treating these liquors which comprise about 2% of agar-agar, so as to extract the latter. Agar is produced, for example, by the group B&V Agar Producers under the names Gold Agar, Agarite and Grand Agar by the company Hispanagar, and under the names Agar-Agar, QSA (Quick Soluble Agar), and Puragar by the company Setexam.

Furcellaran

Furcellaran is obtained commercially from red algae *Furcellaria fasztigiata*. Furcellaran is produced, for example, by the company Est-Agar.

Alginate-Based Compound

For the purposes of the invention, the term "alginate-based compound" means alginic acid, alginic acid derivatives and salts of alginic acid (alginates) or of said derivatives. Preferably, the alginate-based compound is water-soluble.

Alginic acid, a natural substance resulting from brown algae or certain bacteria, is a polyuronic acid composed of 2 uronic acids linked by 1,4-glycosidic bonds: β-D-mannuronic (M) acid and α-L-glucuronic (G) acid. Alginic acid is capable of forming water-soluble salts (alginates) with alkali metals such as sodium, potassium or lithium, substituted cations of lower amines and of ammonium such as methylamine, ethanolamine, diethanolamine or triethanolamine. These alginates are water-soluble in aqueous medium at a pH equal to 4, but dissociate into alginic acid at a pH below 4.

This (these) alginate-based compound(s) are capable of crosslinking in the presence of at least one crosslinking agent, by formation of ionic bonds between said alginate-based compound(s) and said crosslinking agent(s). The formation of multiple crosslinking between several molecules of said alginate-based compound(s) leads to the formation of a water-insoluble gel.

Use is preferably made of alginate-based compounds with a weight-average molecular mass ranging from 10 000 to 1 000 000, preferably from 15 000 to 500 000 and better still from 20 000 to 250 000.

According to a preferred embodiment, the alginate-based compound is alginic acid and/or a salt thereof. Advantageously, the alginate-based compound is an alginate salt, and preferably sodium alginate.

The alginate-based compound may be chemically modified, especially with urea or urethane groups or by hydrolysis, oxidation, esterification, etherification, sulfatation, phosphatation, amination, amidation or alkylation reaction, or by several of these modifications. The derivatives obtained may be anionic, cationic, amphoteric or nonionic.

The alginate-based compounds that are suitable for use in the invention may be represented, for example, by the products sold under the names Kelcosol, Satialgine™ Cecalgum™ or Algogel™ by the company Cargill Products, under the name Protanal™ by the company FMC Biopolymer, under the name Grindsted® Alginate by the company Danisco, under the name Kimica Algin by the company Kimica, and under the names Manucol® and Manugel® by the company ISP.

Polysaccharides of Higher Plants

This category of polysaccharides may be divided into homogeneous polysaccharides (only one saccharide species) and heterogeneous polysaccharides composed of several types of saccharides.

a) Homogeneous Polysaccharides and Derivatives Thereof

The polysaccharide according to the invention may be chosen from celluloses and derivatives or fructosans.

Cellulose and Derivatives

The polysaccharide according to the invention may also be a cellulose or a derivative thereof, especially cellulose ethers or esters (e.g.: methylcellulose, carboxymethylcellulose, hydroxymethylcellulose, hydroxyethylcellulose, hydroxypropylcellulose, hydroxymethylpropylcellulose, cellulose acetate, cellulose nitrate, nitrocellulose).

The invention may also contain a cellulose-based associative polymer. According to the invention, the term "cellulose-based compound" means any polysaccharide compound bearing in its structure linear sequences of anhydroglucopyranose residues (AGU) linked together via β(1,4) glycoside bonds. The repeating unit is the cellobiose dimer. The AGUs are in chair conformation and bear 3 hydroxyl functions: 2 secondary alcohols (in position 2 and 3) and a primary alcohol (in position 6). The polymers thus formed combine together via intermolecular bonds of hydrogen bond type, thus giving the cellulose a fibrillar structure (about 1500 molecules per fiber). The degree of polymerization differs enormously depending on the origin of the cellulose; its value may range from a few hundred to several tens of thousands.

Cellulose has the following chemical structure:

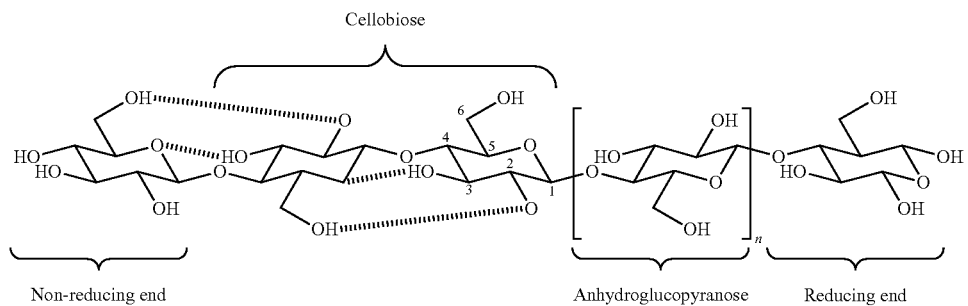

The hydroxyl groups of cellulose may react partially or totally with various chemical reagents to give cellulose derivatives having intrinsic properties. The cellulose derivatives may be anionic, cationic, amphoteric or nonionic. Among these derivatives, cellulose ethers, cellulose esters and cellulose ester ethers are distinguished.

Among the nonionic cellulose ethers, mention may be made of alkylcelluloses such as methylcelluloses and ethylcelluloses; hydroxyalkylcelluloses such as hydroxymethylcelluloses, hydroxyethylcelluloses and hydroxypropylcelluloses; and mixed hydroxy-alkylalkylcelluloses such as hydroxypropylmethylcelluloses, hydroxyethylmethylcelluloses, hydroxyethylethylcelluloses and hydroxybutylmethylcelluloses.

Among the anionic cellulose ethers, mention may be made of carboxyalkyl celluloses and salts thereof. By way of example, mention may be made of carboxymethylcelluloses, carboxymethylmethylcelluloses and carboxymethylhydroxyethylcelluloses and sodium salts thereof.

Among the cationic cellulose ethers, mention may be made of crosslinked or non-crosslinked, quaternized hydroxyethylcelluloses.

The quaternizing agent may in particular be glycidyltrimethylammonium chloride or a fatty amine such as laurylamine or stearylamine. Another cationic cellulose ether that may be mentioned is hydroxyethylcellulosehydroxypropyltrimethyl ammonium.

The quaternized cellulose derivatives are, in particular:
quaternized celluloses modified with groups comprising at least one fatty chain, such as alkyl, arylalkyl or alkylaryl groups comprising at least 8 carbon atoms, or mixtures thereof,
quaternized hydroxyethylcelluloses modified with groups comprising at least one fatty chain, such as alkyl, arylalkyl or alkylaryl groups comprising at least 8 carbon atoms, or mixtures thereof.

The alkyl radicals borne by the above quaternized celluloses or hydroxyethylcelluloses preferably contain from 8 to 30 carbon atoms. The aryl radicals preferably denote phenyl, benzyl, naphthyl or anthryl groups.

Examples of quaternized alkylhydroxyethylcelluloses containing $C_8$-$C_{30}$ fatty chains that may be indicated include the products Quatrisoft LM 200, Quatrisoft LM-X 529-18-A, Quatrisoft LM-X 529-18B ($C_{12}$ alkyl) and Quatrisoft LM-X 529-8 ($C_{18}$ alkyl) sold by the company Amerchol and the products Crodacel QM, Crodacel QL ($C_{12}$ alkyl) and Crodacel QS ($C_{18}$ alkyl) sold by the company Croda.

Among the cellulose derivatives, mention may also be made of:
celluloses modified with groups comprising at least one fatty chain, for instance hydroxyethylcelluloses modified with groups comprising at least one fatty chain, such as alkyl groups, especially of $C_8$-$C_{22}$, arylalkyl and alkylaryl groups, such as Natrosol Plus Grade 330 CS ($C_{16}$ alkyls) sold by the company Aqualon, and
celluloses modified with polyalkylene glycol alkylphenyl ether groups, such as the product Amercell Polymer HM-1500 (nonylphenyl polyethylene glycol (15) ether) sold by the company Amerchol.

Among the cellulose esters are inorganic esters of cellulose (cellulose nitrates, sulfates, phosphates, etc.), organic cellulose esters (cellulose monoacetates, triacetates, amidopropionates, acetatebutyrates, acetatepropionates and acetatetrimellitates, etc.), and mixed organic/inorganic esters of cellulose, such as cellulose acetatebutyrate sulfates and cellulose acetatepropionate sulfates. Among the cellulose ester ethers, mention may be made of hydroxypropylmethylcellulose phthalates and ethylcellulose sulfates.

The cellulose-based compounds of the invention may be chosen from unsubstituted celluloses and substituted celluloses.

The celluloses and derivatives are represented, for example, by the products sold under the names Avicel® (microcrystalline cellulose, MCC) by the company FMC Biopolymers, under the name Cekol (carboxymethylcellulose) by the company Noviant (CP-Kelco), under the name Akucell AF (sodium carboxymethylcellulose) by the company Akzo Nobel, under the name Methocel™ (cellulose ethers) and Ethocel™ (ethylcellulose) by the company Dow, and under the names Aqualon® (carboxymethylcellulose and sodium carboxymethyl-cellulose), Benecel® (methylcellulose), Blanose™ (carboxymethylcellulose), Culminal® (methylcellulose, hydroxypropylmethylcellulose), Klucel® (hydroxypropylcellulose), Polysurf® (cetylhydroxyethylcellulose) and Natrosol® CS (hydroxyethylcellulose) by the company Hercules Aqualon.

Fructosans

The polysaccharide according to the invention may especially be a fructosan chosen from inulin and derivatives thereof (especially dicarboxy and carboxymethyl inulins). Fructans or fructosans are oligosaccharides or polysaccharides comprising a sequence of anhydrofructose units optionally combined with several saccharide residues other than fructose. Fructans may be linear or branched. Fructans may be products obtained directly from a plant or microbial source or alternatively products whose chain length has been modified (increased or decreased) by fractionation, synthesis or hydrolysis, in particular enzymatic. Fructans generally have a degree of polymerization from 2 to about 1,000 and preferably from 2 to about 60. Three groups of fructans are distinguished. The first group corresponds to products whose fructose units are for the most part linked via β(2,1) bonds. These are essentially linear fructans such as inulins. The second group also corresponds to linear fructoses, but the fructose units are essentially linked via β(2,6) bonds. These products are levans. The third group corresponds to mixed fructans, i.e. containing β(2,6) and β(2,1) sequences. These are essentially branched fructans, such as graminans.

The preferred fructans in the compositions according to the invention are inulins. Inulin may be obtained, for example, from chicory, dahlia or Jerusalem artichoke, preferably from chicory.

In particular, the polysaccharide, especially the inulin, has a degree of polymerization from 2 to about 1,000 and preferably from 2 to about 60, and a degree of substitution of less than 2 on the basis of one fructose unit.

The inulin used for this invention is represented, for example, by the products sold under the name Beneo™ inulin by the company Orafti, and under the name Frutafit® by the company Sensus.

b) Heterogeneous Polysaccharides and Derivatives Thereof

The polysaccharides that may be used according to the invention may be gums, for instance cassia gum, karaya gum, konjac gum, gum tragacanth, tara gum, acacia gum or gum arabic.

Gum Arabic

Gum arabic is a highly branched acidic polysaccharide which is in the form of mixtures of potassium, magnesium and calcium salts. The monomer elements of the free acid (arabic acid) are D-galactose, L-arabinose, L-rhamnose and D-glucuronic acid.

Galactomannans (Guar, Locust Bean, Fenugreek, Tara Gum) and Derivatives (Guar Phosphate, Hydroxypropyl Guar, Etc.)

Galactomannans are nonionic polyosides extracted from the endosperm of leguminous seeds, of which they constitute the storage carbohydrate. Galactomannans are macromolecules consisting of a main chain of β(1,4) linked D-mannopyranose units, bearing side branches consisting of a single D-galactopyranose unit α(1,6) linked to the main chain. The various galactomannans differ, firstly, by the proportion of α-D-galactopyranose units present in the polymer, and secondly by significant differences in terms of distribution of galactose units along the mannose chain. The mannose/galactose (M/G) ratio is about 2 for guar gum, 3 for tara gum and 4 for locust bean gum. Galactomannans have the following chemical structure:

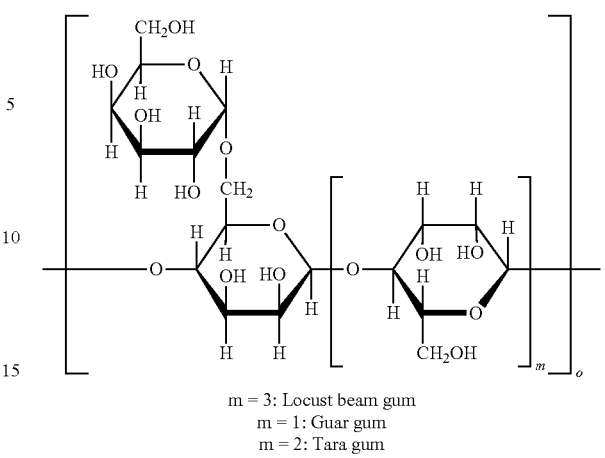

m = 3: Locust beam gum
m = 1: Guar gum
m = 2: Tara gum

Guar

Guar gum is characterized by a mannose/galactose ratio of the order of 2/1. The galactose group is regularly distributed along the mannose chain. The guar gums that may be used according to the invention may be nonionic, cationic or anionic. According to the invention, use may be made of chemically modified or unmodified nonionic guar gums.

The unmodified nonionic guar gums are, for example, the products sold under the names Vidogum GH, Vidogum G and Vidocrem by the company Unipektin and under the name Jaguar by the company Rhodia, under the name Meypro® Guar by the company Danisco, under the name Viscogum™ by the company Cargill, and under the name Supercol® guar gum by the company Aqualon.

The hydrolyzed nonionic guar gums that may be used according to the invention are represented, for example, by the products sold under the name Meyprodor® by the company Danisco.

The modified nonionic guar gums that may be used according to the invention are preferably modified with $C_1$-$C_6$ hydroxyalkyl groups, among which mention may be made, for example, of hydroxymethyl, hydroxyethyl, hydroxypropyl and hydroxybutyl groups.

Such nonionic guar gums optionally modified with hydroxyalkyl groups are sold, for example, under the trade names Jaguar HP60, Jaguar HP 105 and Jaguar HP 120 (hydroxypropyl guar) by the company Rhodia or under the name N-Hance® HP (hydroxypropyl guar) by the company Aqualon.

The cationic galactomannan gums preferably have a cationic charge density of less than or equal to 1.5 meq./g, more particularly between 0.1 and 1 meq./g. The charge density may be determined by the Kjeldahl method. It generally corresponds to a pH of the order of 3 to 9.

In general, for the purposes of the present invention, the term "cationic galactomannan gum" means any galactomannan gum containing cationic groups and/or groups that can be ionized into cationic groups.

The preferred cationic groups are chosen from those comprising primary, secondary, tertiary and/or quaternary amine groups.

The cationic galactomannan gums used generally have a weight-average molecular mass of between 500 and $5 \times 10^6$ approximately and preferably between $10^3$ and $3 \times 10^6$ approximately.

The cationic galactomannan gums that may be used according to the present invention are, for example, gums comprising tri($C_1$-$C_4$)alkylammonium cationic groups. Preferably, 2% to 30% by number of the hydroxyl functions of these gums bear trialkylammonium cationic groups.

Mention may very particularly be made, among these trialkylammonium groups, of the trimethylammonium and triethylammonium groups.

Even more preferentially, these groups represent from 5% to 20% by weight relative to the total weight of the modified galactomannan gum.

According to the invention, the cationic galactomannan gum is preferably a guar gum comprising hydroxypropylt-rimethylammonium groups, i.e. a guar gum modified, for example, with 2,3-epoxypropyltrimethylammonium chloride.

These galactomannan gums, in particular guar gums modified with cationic groups are products already known per se and are, for example, described in U.S. Pat. Nos. 3,589,578 and 4,031,307. Such products are moreover sold especially under the trade names Jaguar EXCEL, Jaguar C13 S, Jaguar C 15, Jaguar C 17 and Jaguar C162 (Guar Hydroxypropyltrimonium Chloride) by the company Rhodia, under the name Amilan® Guar (Guar Hydroxypropyltrimonium Chloride) by the company Degussa, and under the name N-Hance® 3000 (Guar Hydroxypropyltrimonium Chloride) by the company Aqualon.

The anionic guar gums that may be used according to the invention are polymers comprising groups derived from carboxylic, sulfonic, sulfenic, phosphoric, phosphonic or pyruvic acid. The anionic group is preferably a carboxylic acid group. The anionic group may also be in the form of an acid salt, especially a sodium, calcium, lithium or potassium salt.

The anionic guar gums that may be used according to the invention are preferentially carboxymethyl guar derivatives (carboxymethyl guar or carboxymethyl hydroxypropyl guar).

Locust Bean

Locust bean gum is extracted from the seeds of the locust bean tree (*Ceratonia siliqua*).

The unmodified locust bean gum that may be used in this invention is sold, for example, under the name Viscogum™ by the company Cargill, under the name Vidogum L by the company Unipektin and under the name Grinsted® LBG by the company Danisco. The chemically modified locust bean gums that may be used in this invention may be represented, for example, by the cationic locust beans sold under the name Catinal CLB (locust bean hydroxypropyltrimonium chloride) by the company Toho.

Tara Gum

The tara gum that may be used in the context of this invention is sold, for example, under the name Vidogum SP by the company Unipektin.

Glucomannan (Konjac Gum)

Glucomannan is a polysaccharide of high molecular weight (500 000<Mglucomannan <2 000 000) composed of D-mannose and D-glucose units with a branch every 50 or 60 units approximately. It is found in wood, but is also the main constituent of konjac gum. Konjac (*Amorphophallus konjac*) is a plant of the Araceae family.

The products that may be used according to the invention are sold, for example, under the names Propol® and Rheolex® by the company Shimizu.

LM and HM pectins, and derivatives

Pectins are linear polymers of α-D-galacturonic acid (at least 65%) linked in positions 1 and 4 with a certain proportion of carboxylic groups esterified with a methanol group. About 20% of the sugars constituting the pectin molecule are neutral sugars (L-rhamnose, D-glucose, D-galactose, L-arabinose, D-xylose). L-Rhamnose residues are found in all pectins, incorporated into the main chain in positions 1,2.

Uronic acid molecules bear carboxyl functions. This function gives pectins the capacity for exchanging ions, when they are in COO⁻ form. Divalent ions (in particular calcium) have the capacity of forming ionic bridges between two carboxyl groups of two different pectin molecules.

In the natural state, a certain proportion of the carboxylic groups are esterified with a methanol group. The natural degree of esterification of a pectin may range between 70% (apple, lemon) and 10% (strawberry) depending on the source used. Using pectins with a high degree of esterification it is possible to hydrolyze the —$COOCH_3$ groups, so as to obtain weakly esterified pectins. Depending on the proportion of methylated or non-methylated monomers, the chain is thus more or less acidic. HM (high-methoxy) pectins are thus defined as having a degree of esterification of greater than 50%, and LM (low-methoxy) pectins are defined as having a degree of esterification of less than 50%.

In the case of amidated pectins, the —$OCH_3$ group is substituted with an —$NH_2$ group.

Pectins are especially sold by the company Cargill under the name Unipectine™, by the company CP-Kelco under the name Genu, and by Danisco under the name Grinsted Pectin.

Other Polysaccharides

Among the other polysaccharides that may be used according to the invention, mention may also be made of chitin (poly-N-acetyl-D-glucosamine, β(1,4)-2-acetamido-2-deoxy-D-glucose), chitosan and derivatives (chitosan-beta-glycerophosphate, carboxymethylchitin, etc.) such as those sold by the company France-Chitine; glycosaminoglycans (GAG) such as hyaluronic acid, chondroitin sulfate, dermatan sulfate, keratan sulfate, and preferably hyaluronic acid; xylans (or arabinoxylans) and derivatives.

Arabinoxylans are polymers of xylose and arabinose, all grouped under the name pentosans.

Xylans consist of a main chain of β(1,4) linked D-xylose units and on which are found three substituents (Rouau & Thibault, 1987): acid units, α-L-arabinofuranose units, side chains which may contain arabinose, xylose, galactose and glucuronic acid.

According to this variant, the polysaccharide is preferably hyaluronic acid, or a salt thereof such as the sodium salt (sodium hyaluronate).

II. Synthetic Polymeric Gelling Agents

For the purposes of the invention, the term "synthetic" means that the polymer is neither naturally existing nor a derivative of a polymer of natural origin.

The synthetic polymeric hydrophilic gelling agent under consideration according to the invention may or may not be particulate. For the purposes of the invention, the term "particulate" means that the polymer is in the form of particles, preferably spherical particles.

As emerges from the text hereinbelow, the polymeric hydrophilic gelling agent is advantageously chosen from crosslinked acrylic homopolymers or copolymers; associative polymers, in particular associative polymers of polyurethane type; polyacrylamides and crosslinked and/or neutralized 2-acrylamido-2-methylpropanesulfonic acid polymers and copolymers; modified or unmodified carboxyvinyl polymers, and mixtures thereof, especially as defined below.

II.A. Particulate Synthetic Polymeric Gelling Agents

They are preferably chosen from crosslinked polymers. They may especially be crosslinked acrylic homopolymers or copolymers, which are preferably partially neutralized or neutralized, and which are in particulate form.

According to one embodiment, the particulate gelling agent according to the present invention is chosen from crosslinked sodium polyacrylates. Preferably, it has in the dry or non-hydrated state a mean size of less than or equal to 100 μm and preferably less than or equal to 50 μm. The mean size of the particles corresponds to the mass-average diameter (D50) measured by laser particle size analysis or another equivalent method known to those skilled in the art.

Thus, preferably, the particulate gelling agent according to the present invention is chosen from crosslinked sodium polyacrylates, preferably in the form of particles with a mean size (or mean diameter) of less than or equal to 100 microns, more preferably in the form of spherical particles.

As examples of crosslinked sodium polyacrylates, mention may be made of those sold under the names Octacare X100, X110 and RM100 by the company Avecia, those sold under the names Flocare GB300 and Flosorb 500 by the company SNF, those sold under the names Luquasorb 1003, Luquasorb 1010, Luquasorb 1280 and Luquasorb 1110 by the company BASF, those sold under the names Water Lock G400 and G430 (INCI name: Acrylamide/Sodium acrylate copolymer) by the company Grain Processing.

Mention may also be made of crosslinked polyacrylate microspheres, for instance those sold under the name Aquakeep® 10 SH NF by the company Sumitomo Seika.

II.B. Non-Particulate Synthetic Polymeric Gelling Agents

This family of gelling agents may be detailed under the following subfamilies:
1. Associative polymers,
2. Polyacrylamides and crosslinked and/or neutralized 2-acrylamido-2-methylpropanesulfonic acid polymers and copolymers, and
3. Modified or unmodified carboxyvinyl polymers.

II.B.1 Associative Polymers

For the purposes of the present invention, the term "associative polymer" means any amphiphilic polymer comprising in its structure at least one fatty chain and at least one hydrophilic portion. The associative polymers in accordance with the present invention may be anionic, cationic, nonionic or amphoteric.

Associative Anionic Polymers

Among the associative anionic polymers that may be mentioned are those comprising at least one hydrophilic unit, and at least one fatty-chain allyl ether unit, more particularly those whose hydrophilic unit is formed by an unsaturated ethylenic anionic monomer, more particularly by a vinylcarboxylic acid and most particularly by an acrylic acid or a methacrylic acid or mixtures thereof, and whose fatty-chain allyl ether unit corresponds to the monomer of formula (I) below:

$$CH_2=C(R')CH_2OB_nR \quad (I)$$

in which R' denotes H or CH$_3$, B denotes an ethylenoxy radical, n is zero or denotes an integer ranging from 1 to 100, R denotes a hydrocarbon-based radical chosen from alkyl, arylalkyl, aryl, alkylaryl and cycloalkyl radicals, containing from 8 to 30 carbon atoms, preferably 10 to 24 carbon atoms and even more particularly from 12 to 18 carbon atoms.

Anionic amphiphilic polymers of this type are described and prepared, according to an emulsion polymerization process, in patent EP 0 216 479.

Among the associative anionic polymers that may also be mentioned are maleic anhydride/C$_{30}$-C$_{38}$ α-olefin/alkyl maleate terpolymers, such as the product maleic anhydride/ C$_{30}$-C$_{38}$ α-olefin/isopropyl maleate copolymer sold under the name Performa V 1608 by the company Newphase Technologies.

Among the associative anionic polymers, mention may be made, according to a preferred embodiment, of copolymers comprising among their monomers an α,β-monoethylenically unsaturated carboxylic acid and an ester of an α,β-monoethylenically unsaturated carboxylic acid and of an oxyalkylenated fatty alcohol.

Preferentially, these compounds also comprise as monomer an ester of an α,β-monoethylenically unsaturated carboxylic acid and of a C$_1$-C$_4$ alcohol.

Examples of compounds of this type that may be mentioned include Aculyn 22® sold by the company Röhm & Haas, which is a methacrylic acid/ethyl acrylate/oxyalkylenated stearyl methacrylate (comprising 20 EO units) terpolymer or Aculyn 28® (methacrylic acid/ethyl acrylate/ oxyethylenated behenyl methacrylate (25 EO) terpolymer).

Associative anionic polymers that may also be mentioned include anionic polymers comprising at least one hydrophilic unit of olefinic unsaturated carboxylic acid type, and at least one hydrophobic unit exclusively of (C$_{10}$-C$_{30}$)alkyl ester of unsaturated carboxylic acid type. Examples that may be mentioned include the anionic polymers described and prepared according to U.S. Pat. Nos. 3,915,921 and 4,509,949.

Associative anionic polymers that may also be mentioned include anionic terpolymers.

The anionic terpolymer used according to the invention is a linear or branched and/or crosslinked terpolymer, of at least one monomer (1) bearing an acid function in free form, which is partially or totally salified with a nonionic monomer (2) chosen from N,N-dimethylacrylamide and 2-hydroxyethyl acrylate and at least one polyoxyethylenated alkyl acrylate monomer (3) of formula (I) below:

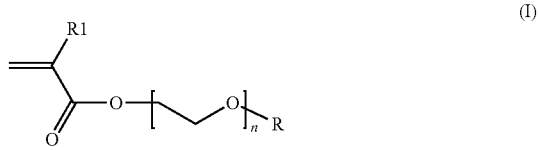

in which R$_1$ represents a hydrogen atom, R represents a linear or branched C$_2$-C$_8$ alkyl radical and n represents a number ranging from 1 to 10.

The term "branched polymer" denotes a non-linear polymer which bears pendent chains so as to obtain, when this polymer is dissolved in water, a high degree of entanglement leading to very high viscosities, at a low speed gradient. The term "crosslinked polymer" denotes a non-linear polymer which is in the form of a three-dimensional network that is insoluble in water but swellable in water, leading to the production of a chemical gel.

The acid function of the monomer (1) is especially a sulfonic acid or phosphonic acid function, said functions being in free or partially or totally salified form. The monomer (1) may be chosen from styrenesulfonic acid, ethanesulfonic acid and 2-methyl-2-[(1-oxo-2-propenyl] amino]-1-propanesulfonic acid (also known as acryloyldimethyltaurate) in free or partially or totally salified form. It is present in the anionic terpolymer preferably in molar proportions of between 5 mol % and 95 mol % and more particularly between 10 mol % and 90 mol %. The monomer (1) will more particularly be 2-methyl-2-[(1-oxo-2-propenyl)amino]-1-propanesulfonic acid in free or partially or totally salified form. The acid function in partially or totally salified form will preferably be an alkali metal salt such as a sodium or potassium salt, an ammonium salt, an amino alcohol salt such as a monoethanolamine salt, or an amino acid salt such as a lysine salt.

The monomer (2) is preferably present in the anionic terpolymer in molar proportions of between 4.9 mol % and 90 mol %, more particularly between 9.5 mol % and 85 mol % and even more particularly between 19.5 mol % and 75 mol %.

In formula (I), examples of linear $C_8$-$C_{16}$ alkyl radicals that may be mentioned include octyl, decyl, undecyl, tridecyl, tetradecyl, pentadecyl and hexadecyl. In formula (I), examples of branched $C_8$-$C_{16}$ alkyl radicals that may be mentioned include 2-ethylhexyl, 2-propylheptyl, 2-butyloctyl, 2-pentylnonyl, 2-hexyldecyl, 4-methylpentyl, 5-methylhexyl, 6-methylheptyl, 15-methylpentadecyl, 16-methylheptadecyl and 2-hexyloctyl.

According to a particular form of the invention, in formula (I), R denotes a $C_{12}$-$C_{16}$ alkyl radical. According to a particular form of the invention, in formula (I), n ranges from 3 to 5.

Tetraethoxylated lauryl acrylate will more particularly be used as monomer of formula (I).

The monomer (3) of formula (I) is preferably present in the anionic terpolymer in molar proportions of between 0.1 mol % and 10 mol % and more particularly between 0.5 mol % and 5 mol %.

According to a particular embodiment of the invention, the anionic terpolymer is crosslinked and/or branched with a diethylenic or polyethylenic compound in the proportion expressed relative to the total amount of monomers used, from 0.005 mol % to 1 mol %, preferably from 0.01 mol % to 0.5 mol % and more particularly from 0.01 mol % to 0.25 mol %.

The crosslinking agent and/or branching agent is preferably chosen from ethylene glycol dimethacrylate, diallyloxyacetic acid or a salt thereof, such as sodium diallyloxyacetate, tetraallyloxyethane, ethylene glycol diacrylate, diallylurea, triallylamine, trimethylolpropane triacrylate and methylenebis(acrylamide), or mixtures thereof.

The anionic terpolymer may contain additives such as complexing agents, transfer agents or chain-limiting agents.

Use will be made more particularly of an anionic terpolymer of 2-methyl-2-[(1-oxo-2-propenyl)amino]-1-propanesulfonic acid partially or totally salified in the form of the ammonium salt, N,N-dimethylacrylamide and tetraethoxylated lauryl acrylate crosslinked with trimethylolpropane triacrylate, of INCI name Polyacrylate Crosspolymer-6, such as the product sold under the trade name Sepimax Zen® by the company SEPPIC.

Cationic Associative Polymers

Cationic associative polymers that may be mentioned include polyacrylates bearing amine side groups.

The polyacrylates bearing quaternized or non-quaternized amine side groups contain, for example, hydrophobic groups of the type such as steareth-20 (polyoxyethylenated (20) stearyl alcohol).

Examples of polyacrylates bearing amino side chains that may be mentioned are the polymers 8781-121B or 9492-103 from the company National Starch.

Nonionic Associative Polymers

The nonionic associative polymers may be chosen from:
copolymers of vinylpyrrolidone and of fatty-chain hydrophobic monomers;
copolymers of $C_1$-$C_6$ alkyl methacrylates or acrylates and of amphiphilic monomers comprising at least one fatty chain;
copolymers of hydrophilic methacrylates or acrylates and of hydrophobic monomers comprising at least one fatty chain, for instance the polyethylene glycol methacrylate/lauryl methacrylate copolymer;
associative polyurethanes.

Associative polyurethanes are nonionic block copolymers comprising in the chain both hydrophilic blocks usually of polyoxyethylene nature (referred to as polyether polyurethanes), and hydrophobic blocks that may be aliphatic sequences alone and/or cycloaliphatic and/or aromatic sequences.

In particular, these polymers comprise at least two hydrocarbon-based lipophilic chains containing from 6 to 30 carbon atoms, separated by a hydrophilic block, the hydrocarbon-based chains possibly being pendent chains or chains at the end of the hydrophilic block. In particular, it is possible for one or more pendent chains to be envisaged. In addition, the polymer may comprise a hydrocarbon-based chain at one end or at both ends of a hydrophilic block.

Associative polyurethanes may be block polymers, in triblock or multiblock form. The hydrophobic blocks may thus be at each end of the chain (for example: triblock copolymer containing a hydrophilic central block) or distributed both at the ends and in the chain (for example: multiblock copolymer). These polymers may also be graft polymers or star polymers. Preferably, the associative polyurethanes are triblock copolymers in which the hydrophilic block is a polyoxyethylene chain comprising from 50 to 1000 oxyethylene groups. In general, associative polyurethanes comprise a urethane bond between the hydrophilic blocks, whence arises the name.

According to one preferred embodiment, a nonionic associative polymer of polyurethane type is used as gelling agent.

As examples of nonionic fatty-chain polyurethane polyethers that may be used in the invention, it is also possible to use Rheolate® FX 1100 (Steareth-100/PEG 136/HDI (hexamethyl diisocyanate) copolymer), Rheolate® 205 containing a urea function, sold by the company Elementis, or Rheolate® 208, 204 or 212, and also Acrysol® RM 184 or Acrysol® RM 2020.

Mention may also be made of the product Elfacos® T210 containing a $C_{12}$-$C_{14}$ alkyl chain, and the product Elfacos® T212 containing a $C_{16-18}$ alkyl chain (PPG-14 Palmeth-60 Hexyl Dicarbamate), from Akzo.

The product DW 1206B® from Röhm & Haas containing a $C_{20}$ alkyl chain and a urethane bond, sold at a solids content of 20% in water, may also be used.

Use may also be made of solutions or dispersions of these polymers, especially in water or in aqueous/alcoholic medium. Examples of such polymers that may be mentioned are Rheolate® 255, Rheolate® 278 and Rheolate® 244 sold by the company Elementis. The products DW 1206F and DW 1206J sold by the company Röhm & Haas may also be used.

The associative polyurethanes that may be used according to the invention are in particular those described in the article by G. Fonnum, J. Bakke and Fk. Hansen, Colloid Polym. Sci., 271, 380-389 (1993).

Even more particularly, according to the invention, use may also be made of an associative polyurethane that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold in particular by the company Röhm & Haas under the names Aculyn® 46 and Aculyn® 44. Aculyn® 46 is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%), and Aculyn® 44 is a polycondensate of polyethylene glycol containing 150 or 180 mol of ethylene oxide, of decyl alcohol and of methylenebis(4-cyclohexyl isocyanate) (SMDI), at 35% by weight in a mixture of propylene glycol (39%) and water (26%).

Use may also be made of solutions or dispersions of these polymers, especially in water or in aqueous/alcoholic medium. Examples of such polymers that may be mentioned include SER AD FX1010, SER AD FX1035 and SER AD 1070 from the company Elementis, and Rheolate® 255, Rheolate® 278 and Rheolate® 244 sold by the company Elementis. Use may also be made of the products Aculyn® 44, Aculyn® 46, DW 1206F and DW 1206J, and also Acrysol® RM 184 from the company Röhm & Haas, or alternatively Borchi Gel LW 44 from the company Borchers, and mixtures thereof.

Amphoteric Associative Polymers

Among the associative amphoteric polymers of the invention, mention may be made of crosslinked or non-crosslinked, branched or unbranched amphoteric polymers, which may be obtained by copolymerization:

1) of at least one monomer of formula (IVa) or (IVb):

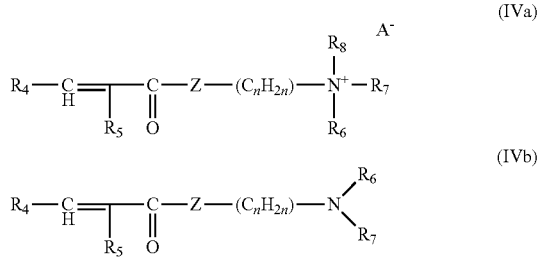

in which $R_4$ and $R_5$, which may be identical or different, represent a hydrogen atom or a methyl radical, $R_6$, $R_7$ and $R_8$, which may be identical or different, represent a linear or branched alkyl radical containing from 1 to 30 carbon atoms;

Z represents an NH group or an oxygen atom;

n is an integer from 2 to 5;

$A^-$ is an anion derived from an organic or mineral acid, such as a methosulfate anion or a halide such as chloride or bromide;

2) of at least one monomer of formula (V):

in which $R_9$ and $R_{10}$, which may be identical or different, represent a hydrogen atom or a methyl radical;

$Z_1$ represents a group OH or a group NHC$(CH_3)_2CH_2SO_3H$;

3) of at least one monomer of formula (VI):

in which $R_9$ and $R_{10}$, which may be identical or different, represent a hydrogen atom or a methyl radical, X denotes an oxygen or nitrogen atom and $R_{11}$ denotes a linear or branched alkyl radical containing from 1 to 30 carbon atoms;

4) optionally at least one crosslinking or branching agent; at least one of the monomers of formula (IVa), (IVb) or (VI) comprising at least one fatty chain containing from 8 to 30 carbon atoms and said compounds of the monomers of formulae (IVa), (IVb), (V) and (VI) possibly being quaternized, for example with a $C_1$-$C_4$ alkyl halide or a $C_1$-$C_4$ dialkyl sulfate.

The monomers of formulae (IVa) and (IVb) of the present invention are preferably chosen from the group consisting of:

dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide, dimethylaminopropylacrylamide, which are optionally quaternized, for example with a $C_1$-$C_4$ alkyl halide or a $C_1$-$C_4$ dialkyl sulfate.

More particularly, the monomer of formula (IVa) is chosen from acrylamidopropyltrimethylammonium chloride and methacrylamidopropyltrimethylammonium chloride.

The compounds of formula (V) of the present invention are preferably chosen from the group formed by acrylic acid, methacrylic acid, crotonic acid, 2-methylcrotonic acid, 2-acrylamido-2-methylpropanesulfonic acid and 2-methacrylamido-2-methylpropanesulfonic acid. More particularly, the monomer of formula (V) is acrylic acid.

The monomers of formula (VI) of the present invention are preferably chosen from the group formed by $C_{12}$-$C_{22}$ and more particularly $C_{16}$-$C_{18}$ alkyl acrylates or methacrylates.

The crosslinking or branching agent is preferably chosen from N,N'-methylenebisacrylamide, triallylmethylammonium chloride, allyl methacrylate, n-methylolacrylamide, polyethylene glycol dimethacrylates, ethylene glycol dimethacrylate, diethylene glycol dimethacrylate, 1,6-hexanediol dimethacrylate and allyl sucrose.

The polymers according to the invention may also contain other monomers such as nonionic monomers and in particular $C_1$-$C_4$ alkyl acrylates or methacrylates.

The ratio of the number of cationic charges/anionic charges in these amphoteric polymers is preferably equal to about 1.

The weight-average molecular weights of the associative amphoteric polymers represent a weight-average molecular mass of greater than 500, preferably between 10 000 and 10 000 000 and even more preferentially between 100 000 and 8 000 000.

Preferably, the associative amphoteric polymers of the invention contain from 1 mol % to 99 mol %, more preferentially from 20 mol % to 95 mol % and even more preferentially from 25 mol % to 75 mol % of compound(s) of formula (IVa) or (IVb). They also preferably contain from 1 mol % to 80 mol %, more preferentially from 5 mol % to 80 mol % and even more preferentially from 25 mol % to 75 mol % of compound(s) of formula (V). The content of compound(s) of formula (VI) is preferably between 0.1 mol % and 70 mol %, more preferentially between 1 mol % and 50 mol % and even more preferentially between 1 mol % and 10 mol %. The crosslinking or branching agent, when it is present, is preferably between 0.0001 mol % and 1 mol % and even more preferentially between 0.0001 mol % and 0.1 mol %.

Preferably, the mole ratio between the compound(s) of formula (IVa) or (IVb) and the compound(s) of formula (V) ranges from 20/80 to 95/5 and more preferentially from 25/75 to 75/25.

The associative amphoteric polymers according to the invention are described, for example, in patent application WO 98/44012.

The amphoteric polymers that are particularly preferred according to the invention are chosen from acrylic acid/acrylamidopropyltrimethylammonium chloride/stearyl methacrylate copolymers.

According to a preferred embodiment, the associative polymer is chosen from nonionic associative polymers and more particularly from associative polyurethanes, such as Steareth-100/PEG-136/HDI Copolymer sold under the name Rheolate FX 1100 by Elementis.

II.B.2 Polyacrylamides and 2-Acrylamido-2-Methylpropanesulfonic Acid Polymers and Copolymers The polymers used that are suitable as aqueous gelling agent for the invention may be crosslinked or non-crosslinked homopolymers or copolymers comprising at least the 2-acrylamido-2-methylpropanesulfonic acid (AMPS®) monomer, in a form partially or totally neutralized with a mineral base other than aqueous ammonia, such as sodium hydroxide or potassium hydroxide. They are preferably totally or almost totally neutralized, i.e. at least 90% neutralized.

These AMPS® polymers according to the invention may be crosslinked or non-crosslinked.

When the polymers are crosslinked, the crosslinking agents may be chosen from the polyolefinically unsaturated compounds commonly used for crosslinking polymers obtained by radical polymerization.

Examples of crosslinking agents that may be mentioned include divinylbenzene, diallyl ether, dipropylene glycol diallyl ether, polyglycol diallyl ethers, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allylic ethers of alcohols of the sugar series, or other allyl or vinyl ethers of polyfunctional alcohols, and also the allylic esters of phosphoric and/or vinylphosphonic acid derivatives, or mixtures of these compounds.

According to one preferred embodiment of the invention, the crosslinking agent is chosen from methylenebisacrylamide, allyl methacrylate and trimethylolpropane triacrylate (TMPTA). The degree of crosslinking generally ranges from 0.01 mol % to 10 mol % and more particularly from 0.2 mol % to 2 mol % relative to the polymer.

The AMPS® polymers that are suitable for use in the invention are water-soluble or water-dispersible. In this case, they are:
either "homopolymers" comprising only AMPS monomers and, if they are crosslinked, one or more crosslinking agents such as those defined above;
or copolymers obtained from AMPS® and from one or more hydrophilic or hydrophobic ethylenically unsaturated monomers and, if they are crosslinked, one or more crosslinking agents such as those defined above. When said copolymers comprise hydrophobic ethylenically unsaturated monomers, these monomers do not comprise a fatty chain and are preferably present in small amounts.

For the purpose of the present invention, the term "fatty chain" means any hydrocarbon-based chain comprising at least 7 carbon atoms. The term "water-soluble or water-dispersible" refers to polymers which, when introduced into an aqueous phase at 25° C., at a mass concentration equal to 1%, make it possible to obtain a macroscopically homogeneous and transparent solution, i.e. a solution with a maximum light transmittance value, at a wavelength equal to 500 nm, through a sample 1 cm thick, of at least 60% and preferably of at least 70%.

The "homopolymers" according to the invention are preferably crosslinked and neutralized, and they may be obtained according to the preparation process comprising the following steps:
(a) the monomer such as AMPS in free form is dispersed or dissolved in a solution of tert-butanol or of water and tert-butanol;
(b) the monomer solution or dispersion obtained in (a) is neutralized with one or more mineral or organic bases, preferably aqueous ammonia $NH_3$, in an amount making it possible to obtain a degree of neutralization of the sulfonic acid functions of the polymer ranging from 90% to 100%;
(c) the crosslinking monomer(s) are added to the solution or dispersion obtained in (b);
(d) a standard free-radical polymerization is performed in the presence of free-radical initiators at a temperature ranging from 10° C. to 150° C.; the polymer precipitates from the tert-butanol-based solution or dispersion.

The water-soluble or water-dispersible AMPS® copolymers according to the invention contain water-soluble ethylenically unsaturated monomers, hydrophobic monomers, or mixtures thereof.

The water-soluble comonomers may be ionic or nonionic.

Among the ionic water-soluble comonomers, examples that may be mentioned include the following compounds, and salts thereof:
(meth)acrylic acid,
styrenesulfonic acid,
vinylsulfonic acid and (meth)allylsulfonic acid,
vinylphosphonic acid,
maleic acid,
itaconic acid,
crotonic acid,
water-soluble vinyl monomers of formula (A) below:

in which:
$R_1$ is chosen from H, —$CH_3$, —$C_2H_5$ and —$C_3H_7$,
$X_1$ is chosen from:
alkyl oxides of type —$OR_2$ where $R_2$ is a linear or branched, saturated or unsaturated hydrocarbon-based radical containing from 1 to 6 carbon atoms, substituted with at least one sulfonic (—$SO_3$—) and/or sulfate (—$SO_4$—) and/or phosphate (—$PO_4H_2$—) group.

Among the nonionic water-soluble comonomers, examples that may be mentioned include:
(meth)acrylamide,
N-vinylacetamide and N-methyl-N-vinylacetamide,
N-vinylformamide and N-methyl-N-vinylformamide,
maleic anhydride,
vinylamine,
N-vinyllactams comprising a cyclic alkyl group containing from 4 to 9 carbon atoms, such as N-vinylpyrrolidone, N-butyrolactam and N-vinylcaprolactam,
vinyl alcohol of formula $CH_2$=CHOH,
water-soluble vinyl monomers of formula (B) below:

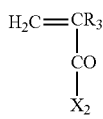

(B)

in which:
$R_3$ is chosen from H, —$CH_3$, —$C_2H_5$ and —$C_3H_7$,
$X_2$ is chosen from alkyl oxides of the type —$OR_4$ where $R_4$ is a linear or branched, saturated or unsaturated hydrocarbon-based radical containing from 1 to 6 carbon atoms, optionally substituted with a halogen (iodine, bromine, chlorine or fluorine) atom; a hydroxyl (—OH) group; ether.

Mention is made, for example, of glycidyl (meth)acrylate, hydroxyethyl methacrylate, and (meth)acrylates of ethylene glycol, of diethylene glycol or of polyalkylene glycol.

Among the hydrophobic comonomers without a fatty chain, mention may be made, for example, of:
styrene and derivatives thereof, such as 4-butylstyrene, α-methylstyrene and vinyltoluene;
vinyl acetate of formula $CH_2$=CH—$OCOCH_3$;
vinyl ethers of formula $CH_2$=CHOR in which R is a linear or branched, saturated or unsaturated hydrocarbon-based radical containing from 1 to 6 carbons;
acrylonitrile;
caprolactone;
vinyl chloride and vinylidene chloride;
silicone derivatives, which, after polymerization, result in silicone polymers such as methacryloxypropyltris(trimethylsiloxy)silane and silicone methacrylamides;
hydrophobic vinyl monomers of formula (C) below:

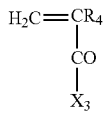

(C)

in which:
$R_4$ is chosen from H, —$CH_3$, —$C_2H_5$ and —$C_3H_7$;
$X_3$ is chosen from:
alkyl oxides of the type —$OR_5$ where $R_5$ is a linear or branched, saturated or unsaturated hydrocarbon-based radical containing from 1 to 6 carbon atoms.

Mention is made, for example, of methyl methacrylate, ethyl methacrylate, n-butyl (meth)acrylate, tert-butyl (meth)acrylate, cyclohexyl acrylate, isobornyl acrylate and 2-ethylhexyl acrylate.

The water-soluble or water-dispersible AMPS® polymers of the invention preferably have a molar mass ranging from 50 000 g/mol to 10 000 000 g/mol, preferably from 80 000 g/mol to 8 000 000 g/mol, and even more preferably from 100 000 g/mol to 7 000 000 g/mol.

As water-soluble or water-dispersible AMPS homopolymers suitable for use in the invention, mention may be made, for example, of crosslinked or non-crosslinked polymers of sodium acrylamido-2-methylpropanesulfonate, such as that used in the commercial product Simulgel 800 (CTFA name: Sodium Polyacryloyldimethyl Taurate), crosslinked ammonium acrylamido-2-methylpropanesulfonate polymers (INCI name: Ammonium Polydimethyltauramide) such as those described in patent EP 0 815 928 B1 and such as the product sold under the trade name Hostacerin AMPS® by the company Clariant.

As water-soluble or water-dispersible AMPS copolymers in accordance with the invention, examples that may be mentioned include:
crosslinked acrylamide/sodium acrylamido-2-methylpropanesulfonate copolymers, such as that used in the commercial product Sepigel 305 (CTFA name: Polyacrylamide/$C_{13}$-$C_{14}$ Isoparaffin/Laureth-7) or that used in the commercial product sold under the name Simulgel 600 (CTFA name: Acrylamide/Sodium acryloyldimethyltaurate/Isohexadecane/Polysorbate-80) by the company SEPPIC;
copolymers of AMPS® and of vinylpyrrolidone or vinylformamide, such as that used in the commercial product sold under the name Aristoflex AVC® by the company Clariant (CTFA name: Ammonium Acryloyldimethyltaurate/VP copolymer) but neutralized with sodium hydroxide or potassium hydroxide;
copolymers of AMPS® and of sodium acrylate, for instance the AMPS/sodium acrylate copolymer, such as that used in the commercial product sold under the name Simulgel EG® by the company SEPPIC or under the trade name Sepinov EM (CTFA name: Hydroxyethyl acrylate/Sodium acryloyldimethyltaurate copolymer);
copolymers of AMPS® and of hydroxyethyl acrylate, for instance the AMPS®/hydroxyethyl acrylate copolymer, such as that used in the commercial product sold under the name Simulgel NS® by the company SEPPIC (CTFA name: Hydroxyethyl acrylate/sodium acryloyldimethyltaurate copolymer (and) squalane (and) polysorbate 60), or such as the product sold under the name Sodium acrylamido-2-methylpropanesulfonate/hydroxyethyl acrylate copolymer, such as the commercial product Sepinov EMT 10 (INCI name: Hydroxyethyl acrylate/Sodium acryloyldimethyltaurate copolymer).

As preferred water-soluble or water-dispersible AMPS copolymers in accordance with the invention, mention may be made of copolymers of AMPS® and of hydroxyethyl acrylate.

II.B.3 Modified or Unmodified Carboxyvinyl Polymers

The modified or unmodified carboxyvinyl polymers may be copolymers derived from the polymerization of at least one monomer (a) chosen from α,β-ethylenically unsaturated carboxylic acids or esters thereof, with at least one ethylenically unsaturated monomer (b) comprising a hydrophobic group.

The term "copolymers" means both copolymers obtained from two types of monomer and those obtained from more than two types of monomer, such as terpolymers obtained from three types of monomer.

Their chemical structure more particularly comprises at least one hydrophilic unit and at least one hydrophobic unit.

The term "hydrophobic group or unit" means a radical with a saturated or unsaturated, linear or branched hydrocarbon-based chain, comprising at least 8 carbon atoms, preferably from 10 to 30 carbon atoms, in particular from 12 to 30 carbon atoms and more preferably from 18 to 30 carbon atoms.

Preferably, these copolymers are chosen from copolymers derived from the polymerization:
of at least one monomer of formula (1) below:

(1)

in which $R_1$ denotes H or $CH_3$ or $C_2H_5$, i.e. acrylic acid, methacrylic acid or ethacrylic acid monomers, and
of at least one monomer of unsaturated carboxylic acid ($C_{10}$-$C_{30}$)alkyl ester type corresponding to the monomer of formula (2) below:

(2)

in which $R_2$ denotes H or $CH_3$ or $C_2H_5$ (i.e. acrylate, methacrylate or ethacrylate units) and preferably H (acrylate units) or $CH_3$ (methacrylate units), $R_3$ denoting a $C_{10}$-$C_{30}$ and preferably $C_{12}$-$C_{22}$ alkyl radical.

The unsaturated carboxylic acid ($C_{10}$-$C_{30}$)alkyl esters are preferably chosen from lauryl acrylate, stearyl acrylate, decyl acrylate, isodecyl acrylate and dodecyl acrylate, and the corresponding methacrylates, such as lauryl methacrylate, stearyl methacrylate, decyl methacrylate, isodecyl methacrylate and dodecyl methacrylate, and mixtures thereof.

According to a preferred embodiment, these polymers are crosslinked.

Among the copolymers of this type that will be used more particularly are polymers derived from the polymerization of a monomer mixture comprising:
  essentially acrylic acid,
  an ester of formula (2) described above in which $R_2$ denotes H or $CH_3$, $R_3$ denoting an alkyl radical containing from 12 to 22 carbon atoms, and
  a crosslinking agent, which is a well-known copolymerizable unsaturated polyethylenic monomer, for instance diallyl phthalate, allyl (meth)acrylate, divinylbenzene, (poly)ethyl ene glycol dimethacrylate and methylenebisacrylamide.

Among the copolymers of this type, use will more particularly be made of those consisting of from 95% to 60% by weight of acrylic acid (hydrophilic unit), 4% to 40% by weight of $C_{10}$-$C_{30}$ alkyl acrylate (hydrophobic unit) and 0 to 6% by weight of crosslinking polymerizable monomer, or alternatively those consisting of from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described previously.

Among the abovementioned polymers, the ones that are most particularly preferred according to the present invention are acrylate/$C_{10}$-$C_{30}$-alkyl acrylate copolymers (INCI name: Acrylates/$C_{10-30}$ Alkyl acrylate Crosspolymer) such as the products sold by the company Lubrizol under the trade names Pemulen TR-1, Pemulen TR-2, Carbopol 1382, Carbopol EDT 2020 and Carbopol Ultrez 20 Polymer, and even more preferentially Pemulen TR-2.

Among the modified or unmodified carboxyvinyl polymers, mention may also be made of sodium polyacrylates such as those sold under the name Cosmedia SP® containing 90% solids and 10% water, or Cosmedia SPL® as an inverse emulsion containing about 60% solids, an oil (hydrogenated polydecene) and a surfactant (PPG-5 Laureth-5), both sold by the company Cognis.

Mention may also be made of partially neutralized sodium polyacrylates that are in the form of an inverse emulsion comprising at least one polar oil, for example the product sold under the name Luvigel® EM by the company BASF.

The modified or unmodified carboxyvinyl polymers may also be chosen from crosslinked (meth)acrylic acid homopolymers.

For the purposes of the present patent application, the term "(meth)acrylic" means "acrylic or methacrylic".

Examples that may be mentioned include the products sold by Lubrizol under the names Carbopol 910, 934, 940, 941, 934 P, 980, 981, 2984, 5984 and Carbopol Ultrez 10 Polymer, or by 3V-Sigma under the name Synthalen® K, Synthalen® L or Synthalen® M.

Among the modified or unmodified carboxyvinyl polymers, mention may be made in particular of Carbopol (CTFA name: carbomer) and Pemulen (CTFA name: Acrylates/$C_{10}$-30 alkyl acrylate crosspolymer) sold by the company Lubrizol.

III. Other Hydrophilic Gelling Agents

The hydrophilic gelling agents that are suitable for use in the invention may also be chosen from mixed silicates and fumed silicas.

III.A. Mixed Silicate

For the purposes of the present invention, the term "mixed silicate" means all silicates of natural or synthetic origin containing several (two or more) types of cations chosen from alkali metals (for example Na, Li, K) or alkaline-earth metals (for example Be, Mg, Ca), transition metals and aluminum.

According to a particular embodiment, the mixed silicate(s) are in the form of solid particles containing at least 10% by weight of at least one silicate relative to the total weight of the particles. In the rest of the present description, these particles are referred to as "silicate particles".

Preferably, the silicate particles contain less than 1% by weight of aluminum relative to the total weight of the particles. Even more preferably, they contain from 0 to 1% by weight of aluminum relative to the total weight of the particles.

Preferably, the silicate particles contain at least 50% by weight of silicate and better still at least 70% by weight relative to the total weight of the particles. Particles containing at least 90% by weight of silicates, relative to the total weight of the particles, are particularly preferred.

In particular, it is an alkali metal or alkaline-earth metal, aluminum or iron silicate or mixture of silicates.

Preferably, it is sodium, magnesium and/or lithium silicate.

To ensure good cosmetic properties, these silicates are generally in a finely divided form, and in particular in the form of particles with a mean size ranging from 2 nm to 1 µm (from 2 nm to 1000 nm), preferably from 5 nm to 600 nm and even more preferentially from 20 to 250 nm.

The silicate particles may have any form, for example the form of spheres, flakes, needles, platelets, disks, leaflets, or totally random forms. Preferably, the silicate particles are in the form of disks or leaflets.

Thus, the term "mean size" of the particles means the numerical mean size of the largest dimension (length) that it is possible to measure between two diametrically opposite points on an individual particle. The size may be determined, for example, by transmission electron microscopy or by measuring the specific surface area via the BET method or with a laser particle size analyzer.

When the particles are in the form of disks or leaflets, they generally have a thickness ranging from about 0.5 nm to 5 nm.

The silicate particles may consist of an alloy with metal or metalloid oxides, obtained, for example, by thermal melting of the various constituents thereof. When the particles also comprise such a metal or metalloid oxide, this oxide is preferably chosen from silicon, boron or aluminum oxide.

According to a particular embodiment of the invention, the silicates are phyllosilicates, namely silicates having a structure in which the $SiO_4$ tetrahedra are organized in leaflets between which the metal cations are enclosed.

The mixed silicates that are suitable for use in the invention may be chosen, for example, from montmorillonites, hectorites, bentonites, beidellite and saponites. According to a preferred embodiment of the invention, the mixed silicates used are more particularly chosen from hectorites and bentonites, and better still from laponites.

A family of silicates that is particularly preferred in the compositions of the present invention is thus the laponite family. Laponites are sodium magnesium silicates also possibly containing lithium, which have a layer structure similar to that of montmorillonites. Laponite is the synthetic form of the natural mineral known as hectorite. The synthetic origin of this family of silicates is of considerable advantage over the natural form, since it allows good control of the composition of the product. In addition, laponites have the advantage of having a particle size that is much smaller than that of the natural hectorite and bentonite.

Laponites that may especially be mentioned include the products sold under the following names: Laponite® XLS, Laponite® XLG, Laponite® RD, Laponite® RDS, Laponite® XL21 (these products are sodium magnesium silicates and sodium lithium magnesium silicates) by the company Rockwood Additives Limited.

III.B. Hydrophilic Fumed Silica

The fumed silicas according to the present invention are hydrophilic.

The hydrophilic fumed silicas are obtained by pyrolysis of silicon tetrachloride ($SiCl_4$) in a continuous flame at 1000° C. in the presence of hydrogen and oxygen. Among the fumed silicas of hydrophilic nature that may be used according to the present invention, mention may especially be made of those sold by the company Degussa or Evonik Degussa under the trade names Aerosil® 90, 130, 150, 200, 300 and 380 or alternatively by the company Cabot under the name Carbosil $H_5$.

Dispersion of Anhydrous Composite Material

As indicated previously, a composition according to the invention comprises in its aqueous phase a dispersion of an anhydrous composite material.

For the purposes of the invention, the expression "dispersion of an anhydrous composite material" denotes the fact that the anhydrous composite material is present in particulate form in the aqueous phase. These particles are in particular distributed homogeneously therein and advantageously are thus essentially in a form different from an aggregated form. Thus, the particles of the anhydrous composite material are individually isolated from the others.

Therefore, the aqueous phase of the composition of the present invention contains a dispersion of an anhydrous composite material under a particulate form.

For the purposes of the present invention, the term "anhydrous" refers to a composite material comprising a content of less than or equal to 1% by weight and preferably less than or equal to 0.5% by weight of water relative to the total weight of said anhydrous composite material, or is even free of water. Where appropriate, such small amounts of water may especially be introduced by ingredients of the composition that may contain residual amounts thereof.

For the purposed of the invention, the expression "composite material" means a material containing different compounds with distinct properties. Such compounds combine to form a unique composite material with its own properties. It may be divided in particulate sub-units but each sub-units keep the native properties of the cohesive form of the composite material.

Thus, such composite material possesses its own composition. When the composite material according to the present invention is introduced in another composition, it does not decompose and keep its own properties. In other terms, when the composite material is introduced in another composition, it remains but under another form, i.e. under a particulate form. Thus, it allows the composition containing it to benefit from its properties.

In particular, a composition according to the invention comprises from 0.1% to 30% by weight, preferably from 0.5% to 20% by weight, and better still from 1% to 5% by weight of anhydrous composite material, relative to the total weight of the composition.

Preferably, a composition according to the invention comprises a weight ratio of anhydrous composite material/hydrophilic gelling agent(s) ranging from 0.2 to 30, in particular from 0.5 to 28, preferably from 0.6 to 21 and better still from 0.6 to 10.

According to the invention, an anhydrous composite material is formed from at least one lipophilic gelling agent, fillers and a fatty phase.

Lipophilic Gelling Agent

The anhydrous composite material comprises from 3% to 15% by weight of at least one hydrophilic gelling agent, relative to the total weight of the material.

For the purposes of the present invention, the term "lipophilic gelling agent" means a compound that is capable of gelling the fatty phase of the anhydrous composite material according to the invention.

The lipophilic gelling agent(s) are liposoluble or lipodispersible.

According to a particular embodiment of the invention, the lipophilic gelling agent(s) are organic or mineral.

According to another particular embodiment of the invention, the lipophilic gelling agent(s) are non-silicone-based.

The gelling agent(s) that may be used in the context of the invention may be organic, polymeric or molecular lipophilic gelling agents.

As examples of lipophilic gelling agents that may be used in the context of the invention, mention may be made of modified natural micas such as aluminum magnesium potassium fluorosilicate, in particular the product sold by the company Sensient under the name Submica M, fatty acid esters of dextrin such as dextrin palmitate, in particular the product sold by the company Chiba Flour Milling under the name Rheopearl TL2-OR, or the dextrin palmitate sold by the same company under the name Rheopearl KL2-OR, and also the dextrin myristate, in particular the product sold by the company Chiba Flour Milling under the name Rheopearl MKL2, triesters of a $C_8$-$C_{30}$ fatty acid and of mono- or polyglycerol, such as glyceryl trihydroxystearate, in particular the product sold by the company Elementis under the name Thixcin R or Rheocin sold by the company Byk Additives & Instruments.

According to a particular embodiment of the invention, the lipophilic gelling agent(s) are organic.

According to a particular embodiment, the lipophilic gelling agent(s) that may be used in the context of the invention are chosen from $C_8$-$C_{30}$ fatty acid esters of dextrin and triesters of a $C_8$-$C_{30}$ fatty acid and of mono- or polyglycerol, in particular with 2 to 10 glycerol units, and preferably from triesters of a $C_8$-$C_{30}$ fatty acid and of mono- or polyglycerol.

Fatty Acid Esters of Dextrin

The fatty acid esters of dextrin used according to the invention may be chosen especially from monoesters or polyesters of dextrin and of at least one fatty acid, corresponding to formula (C):

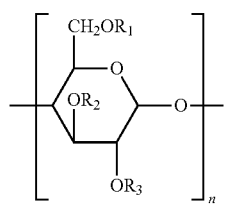

(C)

in which:
- n is an integer ranging from 3 to 150, especially from 10 to 100 and preferably from 15 to 40; and
- the radicals $R_1$, $R_2$ and $R_3$ represent a hydrogen atom or an acyl group (R—CO—) in which the radical R is a linear or branched, saturated or unsaturated hydrocarbon-based group containing from 6 to 50, especially from 8 to 30, or even 12 to 22 and better still 12 to 18 carbon atoms, with the proviso that at least one of said radicals $R_1$, $R_2$ or $R_3$ is other than a hydrogen atom.

In particular, $R_1$, $R_2$ and $R_3$ may represent hydrogen or an acyl group (R—CO—) in which R is a hydrocarbon-based radical as defined previously, with the proviso that at least two of said radicals $R_1$, $R_2$ or $R_3$ are identical and other than hydrogen.

The radicals $R_1$, $R_2$ and $R_3$ may all contain an acyl group (R—CO), which is identical or different and especially identical.

The radical R—CO— of the dextrin ester of formula (C) may be chosen especially from caprylyl, caproyl, lauroyl, myristyl, palmityl, stearyl, eicosanyl, docosanoyl, isovaleryl, 2-ethylbutyryl, ethylmethyl acetyl, isoheptanyl, 2-ethylhexanyl, isononanyl, isodecanyl, isotridecanyl, isomyristyl, isopalmityl, isostearyl, isohexanyl, decenyl, dodecenyl, tetradecenyl, myristyl, hexadecenoyl, palmitoleyl, oleyl, elaidyl, eicosenyl, sorbyl, linoleyl, linolenyl, punicyl, arachidonyl and stearolyl radicals, and mixtures thereof.

The radical R—CO is advantageously linear.

R—CO is preferably a palmityl radical or a myristyl radical, and even more preferentially a palmityl radical.

n advantageously ranges from 25 to 35, preferably from 27 to 33, and better is equal to 30.

Preferably, at least one dextrin palmitate and/or at least one dextrin myristate is used as fatty acid ester of dextrin. They may be used alone or as a mixture with other esters.

Advantageously, the fatty acid ester of dextrin has a degree of substitution of less than or equal to 2.5, especially ranging from 1.5 to 2.5, on the basis of one glucose unit. The weight-average molecular weight of the dextrin ester may in particular be from 10 000 to 150 000, especially from 12 000 to 100 000 and even from 15 000 to 80 000.

Dextrin esters are commercially available, in particular dextrin palmitates, for example under the name Rheopearl TL2-OR or Rheopearl KL2-OR from the company Chiba Flour Milling, and under the name Rheopearl KS from the company Chiba Flour Milling, and dextrin myristates, for example under the name Rheopearl MKL2 from the company Chiba Flour Milling.

According to a particular embodiment of the invention, use will be made of a mixture of a fatty acid ester of dextrin whose degree of substitution is less than 2 on the basis of one glucose unit and of a fatty acid ester of dextrin whose degree of substitution is greater than 2 on the basis of one glucose unit, as described in patent application FR 2 843 020.

According to one embodiment, the fatty acid ester of dextrin whose degree of substitution is less than 2 on the basis of one glucose unit advantageously corresponds to formula (IV) below:

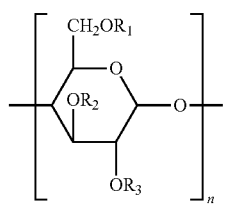

(IV)

in which:
- the radicals $R_1$, $R_2$ and $R_3$ represent a hydrogen atom or an acyl group (R—CO—) in which the radical R is a linear or branched, saturated or unsaturated hydrocarbon-based group containing from 6 to 50, especially from 8 to 30, or even 12 to 22 and better still 12 to 18 carbon atoms, with the proviso that at least one of said radicals $R_1$, $R_2$ or $R_3$ is other than a hydrogen atom;
- n is an integer ranging from 3 to 150, especially from 10 to 100 and preferably from 15 to 40.

The radical R—CO— of the dextrin ester of formula (IV) may be chosen especially from caprylyl, caproyl, lauroyl, myristyl, palmityl, stearyl, eicosanyl, docosanoyl, isovaleryl, 2-ethylbutyryl, ethylmethyl acetyl, isoheptanyl, 2-ethylhexanyl, isononanyl, isodecanyl, isotridecanyl, isomyristyl, isopalmityl, isostearyl, isohexanyl, decenyl, dodecenyl, tetradecenyl, myristyl, hexadecenoyl, palmitoleyl, oleyl, elaidyl, eicosenyl, sorbyl, linoleyl, linolenyl, punicyl, arachidonyl and stearolyl radicals, and mixtures thereof.

The radical R—CO is advantageously linear. The radical R—CO is preferably a palmityl radical or a myristyl radical, and even more preferentially a palmityl radical.

n advantageously ranges from 25 to 35, preferably from 27 to 33, and better is equal to 30.

Preferably, use is made of a fatty acid ester of dextrin whose degree of substitution is less than 2 on the basis of one glucose unit, such that the degree of substitution is less than 1.9, preferably less than 1.8 and more preferably is between 1.5 and 1.7. Some of these dextrin esters are commercially available, especially under the name Rheopearl TL from the company Chiba Flour Milling.

The weight-average molecular weight of the fatty acid ester of dextrin whose degree of substitution is less than 2 on the basis of one glucose unit is preferably between 10 000 and 30 000, more preferably between 15 000 and 20 000. The weight-average molecular weight is determined by gas chromatography, with polystyrene calibration.

According to one embodiment, the fatty acid ester of dextrin whose degree of substitution is greater than 2 on the basis of one glucose unit corresponds to formula (V):

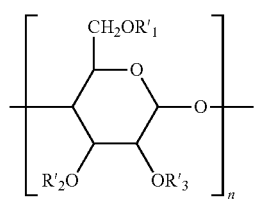

in which:

the radicals $R'_1$, $R'_2$ and $R'_3$, which may be identical or different, are chosen from a hydrogen atom and an acyl group ($R'$—CO—) in which the radical $R'$ is a linear or branched, saturated or unsaturated hydrocarbon-based group containing from 6 to 50, especially from 8 to 30, or even 12 to 22 and better still 12 to 18 carbon atoms, with the proviso that at least one of said radicals $R'_1$, $R'_2$ or $R'_3$ is other than a hydrogen atom;

n is an integer ranging from 3 to 150, especially from 10 to 100 and preferably from 15 to 40.

$R'$ and n may have the same meaning as R and n described previously.

Advantageously, the radicals $R'_1$, $R'_2$ and $R'_3$ are identical, with the proviso that at least one of said radicals $R'_1$, $R'_2$ or $R'_3$ is other than a hydrogen atom.

Preferably, use is made of a fatty acid ester of dextrin whose degree of substitution is greater than 2 on the basis of one glucose unit, such that the degree of substitution is greater than 2.1, preferably between 2.1 and 2.3.

The weight-average molecular weight of the fatty acid ester of dextrin whose degree of substitution is greater than 2 on the basis of one glucose unit is preferably between 10 000 and 30 000, more preferably between 15 000 and 20 000. The weight-average molecular weight is determined by gas chromatography, with polystyrene calibration.

As examples of dextrin esters of formula (V) according to the invention, mention may be made of Rheopearl KL sold by the company Chiba Flour Milling.

Triesters of Fatty Acid and of Mono- or Polyglycerol

According to a particular embodiment, the triester(s) of a fatty acid and of mono- or polyglycerol are triesters of fatty acid and of monoglycerol.

The term "fatty acid" means a linear or branched, saturated or unsaturated acid, comprising from 8 to 30 carbon atoms, preferably from 10 to 24 carbon atoms, even more preferentially from 12 to 22 and better still from 16 to 20 carbon atoms, optionally substituted with one or more hydroxyl groups. According to a particular embodiment of the invention, the fatty acid(s) are linear and saturated, substituted with at least one hydroxyl group.

The fatty acids may be chosen from oleic acid, lauric acid, palmitic acid, myristic acid, stearic acid, linoleic acid, capric acid and behenic acid, optionally substituted with at least one hydroxyl group, or mixtures thereof. Preferably, the fatty acid(s) are chosen from stearic acid, stearic acids substituted with at least one hydroxyl group, and mixtures thereof, and are more preferentially chosen from stearic acid, 12-hydroxystearic acid, and mixtures thereof, and even better still it is 12-hydroxystearic acid.

According to a particular embodiment of the invention, the triester of a $C_8$-$C_{30}$ fatty acid and of mono- or poly glyceryl is glyceryl tris(12-hydroxystearate).

As examples of triester of a $C_8$-$C_{30}$ fatty acid and of mono- or polyglycerol, mention may be made of glyceryl tri(hydroxystearate) (INCI name: Trihydroxystearin), for instance the product sold by the company Elementis under the name Thixcin R or the product sold by the company Byk Additives & Instruments under the name Rheocin.

According to a particular embodiment of the invention, the lipophilic gelling agent(s) that may be used in the context of the invention are chosen from fatty acid esters of dextrin, preferably dextrin palmitate and dextrin myristate.

According to another particular embodiment of the invention, the lipophilic gelling agent(s) that may be used in the context of the invention are chosen from triesters of a $C_8$-$C_{30}$ fatty acid and of monoglycerol, preferably glyceryl tri (hydroxystearate), and even more preferentially glyceryl tris(12-hydroxystearate).

The lipophilic gelling agent(s) are present in the anhydrous composite material in an amount of between 3% and 15% by weight, preferably from 5% to 12% by weight and even more preferentially from 8.5% to 10% by weight, relative to the total weight of the material.

Fillers

The anhydrous composite material in accordance with the invention comprises from 10% to 50% by weight and preferably from 20% to 50% by weight of fillers relative to the total weight of the material.

The term "filler" should be understood as meaning colorless or white, mineral or synthetic particles of any shape, which are insoluble in the medium of the composition, irrespective of the temperature at which the composition is manufactured.

The filler(s) may especially be organic fillers and/or inorganic fillers.

The fillers used in the present invention may be characterized by their specific surface area per unit mass or per unit volume, their size expressed as the volume-mean diameter D(4,3), their non-tapped density and/or their oil-absorbing capacity.

The sizes of the fillers may be measured by static light scattering using a commercial particle size analyzer such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is especially described in the publication by Van de Hulst, H. C., *Light Scattering by Small Particles*, Chapters 9 and 10, Wiley, New York, 1957.

The specific surface area per unit mass may be determined by the nitrogen absorption method, known as the BET (Brunauer-Emmett-Teller) method, described in *The Journal of the American Chemical Society*, vol. 60, page 309, February 1938 and corresponding to international standard ISO 5794/1 (annex D). The BET specific surface corresponds to the total specific surface of the particles under consideration.

The specific surface area per unit of volume is given by the relationship: $S_V = S_M \times \rho$ where $\rho$ is the tapped density, expressed in g/cm³, and $S_M$ is the specific surface area per unit of mass, expressed in m²/g, as defined above.

In the context of the present invention, this density, known as the tapped density, may be assessed according to the following protocol:

40 g of powder are poured into a measuring cylinder; the measuring cylinder is then placed on a Stay 2003 machine from Stampf Volumeter; the measuring cylinder is then subjected to a series of 2500 tapping actions (this operation is repeated until the difference in volume between two consecutive tests is less than 2%); the final volume Vf of tapped powder is then measured directly on the measuring cylinder. The tapped density is determined by the ratio m/Vf, in this instance 40/Vf (Vf being expressed in cm³ and m in g).

The oil-absorbing capacity, measured at the wet point and denoted Wp, corresponds to the amount of oil which it is necessary to add to 100 g of particles in order to obtain a homogeneous paste.

It is measured according to the "wet point" method or the method for determining the oil uptake of a powder described in standard NF T 30-022. It corresponds to the amount of oil adsorbed onto the available surface of the powder and/or absorbed by the powder by measurement of the wet point, described below:

An amount m=2 g of powder is placed on a glass plate, and the oil (isononyl isononanoate) is then added dropwise. After addition of 4 to 5 drops of oil to the powder, mixing is carried out using a spatula, and addition of the oil is continued until conglomerates of oil and powder have formed. From this point, the oil is added at the rate of one drop at a time and the mixture is subsequently triturated with the spatula. The addition of oil is stopped when a firm, smooth paste is obtained. This paste must be able to be spread over the glass plate without cracks or the formation of lumps. The volume Vs (expressed in ml) of oil used is then noted.

The oil uptake corresponds to the ratio Vs/m.

According to a particular embodiment, the fillers used in the present invention have an oil-absorbing capacity of from 0.25 to 3.5 mL/g, preferably from 0.93 to 2.5 mL/g, or even from 1.25 to 2.5 mL/g.

According to a particular embodiment, the fillers used in the present invention have a size expressed as the volume-mean diameter D(4,3) ranging from 0.1 µm to 40 µm, preferably from 0.5 µm to 20 µm and even more preferentially from 1 µm to 16 µm.

According to a particular embodiment of the invention, the fillers used in the present invention have a heterogeneous particle size, i.e. a large particle size distribution for a given size expressed as the volume-mean diameter.

According to a particular embodiment, the fillers used in the present invention have a non-tapped density ranging from 0.2 g/cm³ to 2.2 g/cm³.

Organic Fillers

In the present patent application, the term "organic filler" means any organic solid that is insoluble in the medium at room temperature (25° C.).

The term "organic" refers to any compound or polymer whose chemical structure comprises at least one or more carbon atoms.

As organic fillers that may be used in the anhydrous composite material of the invention, examples that may be mentioned include polyamide (Nylon®) particles and especially those sold under the names Orgasol® by the company Atochem; polyethylene powders; microspheres based on acrylic copolymers, such as those made of ethylene glycol dimethacrylate/lauryl methacrylate copolymer sold by the company Dow Corning under the name Polytrap®; polymethyl methacrylate microspheres, sold under the name Microsphere M-100° by the company Matsumoto or under the name Covabead LH85® by the company Wackherr; ethylene-acrylate copolymer powders, such as those sold under the name Flobeads® by the company Sumitomo Seika Chemicals; expanded powders, such as hollow microspheres and especially microspheres formed from a terpolymer of vinylidene chloride, acrylonitrile and methacrylate and sold under the name Expancel® by the company Kemanord Plast under the references 551 DE 12® (particle size of about 12 µm), 551 DE 20® (particle size of about 30 µm), 551 DE 50° (particle size of about 40 µm), or the microspheres sold under the name Micropearl F 80 ED® by the company Matsumoto; powders of natural organic materials such as polysaccharide powders, and in particular starch powders, especially of crosslinked or non-crosslinked corn, wheat or rice starch, powders of starch crosslinked with octenylsuccinate anhydride, sold under the name Dry-Flo® by the company National Starch, waxy corn starch powders such as the product sold under the names C*Gel 04201 by the company Cargill, Amidon de Mais B by the company Roquette, and Organic Corn Starch by the company Draco Natural Products; cellulose particles such as those sold under the name Cellulobeads by the company Daito Kasei Kogyo; mention may also be made of the Tencel range from the company Lenzing; silicone resin microbeads such as those sold under the name Tospearl by the company Toshiba Silicone, especially Tospearl 240; amino acid powders such as the lauroyllysine powder sold under the name Amihope LL-11® by the company Ajinomoto; wax microdispersion particles, which preferably have mean sizes of less than 25 µm, especially ranging from 0.5 µm to 25 µm, and which consist essentially of a wax or a mixture of waxes, such as the products sold under the name Aquacer by the company Byk Cera, and especially Aquacer 520 (mixture of synthetic and natural waxes), Aquacer 514° or 513° (polyethylene waxes), Aquacer 511° (polymeric wax), or such as the products sold under the name Jonwax 120 by the company Johnson Polymer (mixture of polyethylene and paraffin waxes) and under the name Ceraflour 961® by the company Byk Cera (micronized modified polyethylene wax); and mixtures thereof.

According to a particular embodiment of the invention, the organic filler(s) are chosen from spherical cellulose particles, powders of an N-acylamino acid bearing a $C_8$-$C_{22}$ acyl group, and polyamide particles, and mixtures thereof, and are preferably chosen from spherical cellulose particles and powders of an N-acylamino acid bearing a $C_8$-$C_{22}$ acyl group, and mixtures thereof.

In the context of the present invention, the term "spherical particles" means particles in the form or substantially in the form of a sphere, which are insoluble in the medium of the composition according to the invention, even at the melting point of the medium (about 100° C.).

According to a particular embodiment, the spherical cellulose particles that may be used in the context of the invention are microparticles. Preferably, they have a particle size expressed as the volume-mean diameter D(4,3) ranging from 0.1 to 35 µm, preferably from 1 to 20 µm and more particularly from 4 to 15 µm.

Examples of spherical cellulose microparticles that may especially be mentioned include the solid cellulose beads sold under the names Cellulobeads D-10, Cellulobeads D-5 and Cellulobeads USF by the company Daito Kasei Kogyo.

The N-acylamino acids comprise an acyl group containing from 8 to 22 carbon atoms, for instance a 2-ethylhexanoyl, caproyl, lauroyl, myristoyl, palmitoyl, stearoyl or cocoyl group. The amino acid may be, for example, lysine, glutamic acid or alanine, preferably lysine.

According to a particular embodiment, the N-acylamino acid(s) comprise an acyl group containing from 10 to 14 carbon atoms. Preferably, it is a lauroyl group. Advantageously, the N-acylamino acid powder may be a lauroyllysine powder such as the product sold under the name Amihope LL by the company Ajinomoto or the product sold under the name Comm 5105 S by the company Comm.

Inorganic Fillers

In the present patent application, the term "inorganic filler" means any inorganic solid that is insoluble in the medium at room temperature (25° C.).

The term "inorganic" refers to any compound or polymer whose chemical structure does not comprise any carbon atoms.

As an example of inorganic fillers, mention may be made of porous spherical silica particles with a particle size expressed as the volume-mean diameter D(4,3) ranging from 0.5 μm to 30 μm, more particularly from 1 μm to 20 μm and preferentially from 1 μm to 16 μm.

In the present patent application, the term "spherical particles" means particles in the form or substantially in the form of a sphere, which are insoluble in the medium of the composition according to the invention, even at the melting point of the medium (about 100° C.).

According to a particular embodiment, they have a specific surface area ranging from 30 m$^2$/g to 1000 m$^2$/g and more particularly from 150 m$^2$/g to 800 m$^2$/g.

According to another particular embodiment, they have an oil-absorbing capacity ranging from 0.15 ml/g to 5 ml/g and more particularly from 1.30 ml/g to 1.90 ml/g.

As examples of porous silica microbeads, use may be made of the following commercial products: Silica Beads SB-150, SB-300 or SB 700, preferentially SB 300 from the company Miyoshi Kasei; the Sunsphere range from the company Asahi Glass AGC SI-TECH, especially Sunsphere H-51 or Sunsphere 12L, Sunsphere H-201 H-52 and H-53; Sunsil 130 from the company Sunjin; Spherica P-1500 from the company Ikeda Corporation; Sylosphere from the company Fuji Silysia; the Silica Pearl and Satinier ranges from the company JGC Catalysts and Chemicals, more particularly Satinier M13 and M16, the silicas MSS-500 from the company Kobo, and more particularly MSS-500-20N, and also Silica Shells from the company Kobo.

Mention may also be made of zeolites, such as the products sold by the company Zeochem under the names Zeoflair 300, Zeoflair 200, Zeoflair 100, X-Mol and X-Mol MT.

Zeolite is a crystal formed from an aluminosilicate microporous backbone, the connected empty spaces of which are initially occupied by cations and water molecules. They are also referred to as molecular sieves.

Mention may also be made of calcium magnesium carbonate, such as the products sold by the company Imerys under the name Calcidol, by the company LCW (Sensient) under the name Carbomat or by the company Omya under the name Omyacare S 60-AV.

Mention may also be made of lamellar inorganic particles, such as talcs, micas or nacres, and mixtures thereof.

Talcs are hydrated magnesium silicates usually comprising aluminum silicate. The crystal structure of talc consists of repeated layers of a sandwich of brucite between layers of silica.

More particularly, the lamellar particles are chosen from talcs.

Advantageously, use is more particularly made, in the anhydrous composite material of the invention, as lamellar particles, of talc, such as the products sold under the names Luzenac Pharma M and UM by the company Imerys, Rose Talc and Talc SG-2000 by the company Nippon Talc; mica, such as the products sold under the names Mica M RP and Silk Mica by the company Merck; titanium micas such as mica/titanium oxide/brown iron oxide (CTFA: Mica/Iron oxides/Titanium dioxide), sold under the name Cloisonne Rouge Flambe 440 X by the company Engelhard. A mica that may be mentioned is the mica sold under the name Sericite S-152-BC by the company Miyoshi Kasei.

Among the inorganic fillers, mention may be made of perlite particles and preferably expanded perlite particles.

The perlites that may be used according to the invention are generally aluminosilicates of volcanic origin and have the composition:

70.0%-75.0% by weight of silica $SiO_2$;
12.0%-15.0% by weight of aluminum oxide $Al_2O_3$;
3.0%-5.0% of sodium oxide $Na_2O$;
3.0%-5.0% of potassium oxide $K_2O$;
0.5%-2% of iron oxide $Fe_2O_3$;
0.2%-0.7% of magnesium oxide MgO;
0.5%-1.5% of calcium oxide CaO;
0.05%-0.15% of titanium oxide $TiO_2$.

Mention may be made especially of the perlites sold under the names Optimat 2550 OR by the company World Minerals, and Europerl EMP-2 and Europerl 1 by the company Imerys.

According to a particular embodiment, the inorganic filler(s) that may be used in the context of the invention are chosen from porous spherical silica particles, and preferably porous spherical silica microparticles.

According to a preferred embodiment, the anhydrous composite material comprises one or more fillers chosen from spherical cellulose particles, powders of an N-acylamino acid bearing a $C_8$-$C_{22}$ acyl group, and polyamide particles, porous spherical silica particles and mixtures thereof, and are preferably chosen from spherical cellulose particles, powders of an N-acylamino acid bearing a $C_8$-$C_{22}$ acyl group and porous spherical silica particles, and mixtures thereof.

Preferably, the anhydrous composite material comprises at least two different fillers, and preferably at least 5% by weight of a first filler and at least 5% by weight of a second filler different from the first, relative to the total weight of the anhydrous composite material.

According to a first preferred aspect of the invention, the anhydrous composite material may comprise at least two fillers that are different from each other, one of which is chosen from spherical cellulose particles, powders of an N-acylamino acid bearing a $C_8$-$C_{22}$ acyl group, and polyamide particles, and the other is chosen from spherical cellulose particles and porous spherical silica particles, in particular porous spherical silica microparticles.

According to one embodiment, the anhydrous composite material comprises at least two fillers that are different from each other, the two being chosen from spherical cellulose particles.

According to another embodiment, the anhydrous composite material comprises at least two fillers that are different from each other, one of which is chosen from spherical cellulose particles and the other is chosen from powders of an N-acylamino acid bearing a $C_8$-$C_{22}$ acyl group.

According to one aspect of the invention, the anhydrous composite material may comprise at least two fillers that are different from each other, one of which is chosen from organic fillers and the other is chosen from inorganic fillers.

In particular, the anhydrous composite material may comprise at least two fillers that are different from each other, one of which is chosen from spherical cellulose particles, powders of an N-acylamino acid bearing a $C_8$-$C_{22}$ acyl group and polyamides particles, preferably spherical cellulose particles and powders of an N-acylamino acid bearing a $C_8$-$C_{22}$ acyl group, and the other is chosen from porous spherical silica particles, in particular porous spherical silica microparticles.

According to one embodiment, the anhydrous composite material comprises at least two fillers that are different from each other, one of which is chosen from spherical cellulose particles and the other is chosen from porous spherical silica particles, in particular porous spherical silica microparticles.

According to another embodiment, the anhydrous composite material comprises at least two fillers that are different from each other, one of which is chosen from powders of an N-acylamino acid bearing a $C_8$-$C_{22}$ acyl group and the other is chosen from porous spherical silica particles, in particular porous spherical silica microparticles.

According to another aspect of the invention, the anhydrous composite material comprises at least three fillers that are different from each other, one of which is chosen from inorganic fillers and the other two are chosen from organic fillers.

Preferably, the anhydrous composite material comprises at least three fillers that are different from each other, one of which is chosen from porous spherical silica particles, in particular porous spherical silica microparticles, and the other two are chosen from spherical cellulose particles, powders of an N-acylamino acid bearing a $C_8$-$C_{22}$ acyl group and polyamide particles, preferably spherical cellulose particles and powders of an N-acylamino acid bearing a $C_8$-$C_{22}$ acyl group.

Even more preferentially, the anhydrous composite material comprises at least three fillers that are different from each other, the first of which is chosen from porous spherical silica particles, in particular porous spherical silica microparticles, the second is chosen from spherical cellulose particles, and the third is chosen from powders of an N-acylamino acid bearing a $C_8$-$C_{22}$ acyl group.

The anhydrous composite material in accordance with the invention comprises at least 5% by weight of a first filler, preferably 5% to 25% by weight relative to the total weight of the anhydrous composite material, and at least 5% by weight of a second filler, preferably from 5% to 25% by weight relative to the total weight of the anhydrous composite material, the first filler and the second filler being chosen from spherical cellulose particles, powders of an N-acylamino acid bearing a $C_8$-$C_{22}$ acyl group, polyamide particles and porous spherical silica particles.

When the anhydrous composite material in accordance with the invention comprises at least three fillers that are different from each other, it comprises at least 5% by weight of a first filler, preferably 5% to 25% by weight relative to the total weight of the anhydrous composite material, at least 5% by weight of a second filler, preferably from 5% to 25% by weight relative to the total weight of the anhydrous composite material, and at least 5% by weight of a third filler, preferably 5% to 25% by weight relative to the total weight of the anhydrous composite material, the first, second and third fillers being chosen from spherical cellulose particles, powders of an N-acylamino acid bearing a $C_8$-$C_{22}$ acyl group, polyamide particles and porous spherical silica particles.

According to a particular embodiment, the anhydrous composite material comprises at least one filler chosen from porous spherical silica particles, in particular porous spherical silica microparticles, and the mass ratio R of silica/fillers other than silica is greater than or equal to 0.75, preferably between 0.75 and 3.

Fatty Phase

The anhydrous composite material in accordance with the invention comprises from 40% to 85% by weight of at least one fatty phase, relative to the total weight of the material.

Preferably, the anhydrous composite material is formed from at least 45% to 85% by weight of a fatty phase, preferably from at least 45% to 75% by weight of a fatty phase, and even more preferentially from at least 57% to 70% by weight of a fatty phase, relative to the total weight of the material.

As indicated previously, this amount of fatty phase does not comprise the content of lipophilic gelling agents such as those described above.

For the purpose of the invention, the fatty phase includes any fatty substance that is liquid at room temperature and atmospheric pressure, generally oils, or that is solid at room temperature and atmospheric pressure, like waxes, or any pasty compound, which are present in said anhydrous composite material.

The fatty substance(s) present in the anhydrous composite material may be chosen by a person skilled in the art on the basis of his general knowledge, so as to give the final anhydrous composite material the desired properties, especially in terms of rheological properties (penetrometry measurement, flow, consistency) or in terms of texture and stability.

It is understood that the components of the fatty phase of the anhydrous composite material are different from the other components of the anhydrous composite material, i.e. the lipophilic gelling agents and the fillers.

Pasty Compound

For the purposes of the present invention, the term "pasty compound" means a lipophilic fatty compound with a reversible solid/liquid change of state, and comprising at a temperature of 23° C. a liquid fraction and a solid fraction.

A pasty compound is, at a temperature of 23° C., in the form of a liquid fraction and a solid fraction. In other words, the starting melting point of the pasty compound is less than 23° C. The liquid fraction of the pasty compound, measured at 23° C., represents from 20% to 97% by weight of the pasty compound. This fraction that is liquid at 23° C. more preferentially represents from 25% to 85% and better still from 30% to 60% by weight of the pasty compound.

The liquid fraction by weight of the pasty compound at 23° C. is equal to the ratio of the heat of fusion consumed at 23° C. to the heat of fusion of the pasty compound.

The heat of fusion consumed at 23° C. is the amount of energy absorbed by the sample to change from the solid state to the state that it has at 23° C., formed from a liquid fraction and a solid fraction.

The heat of fusion of the pasty compound is the heat consumed by the compound in order to pass from the solid state to the liquid state. The pasty compound is said to be in the solid state when all of its mass is in solid form. The pasty compound is said to be in the liquid state when all of its mass is in liquid form.

The heat of fusion of the pasty compound is equal to the area under the curve of the thermogram obtained using a differential scanning calorimeter (DSC), such as the calorimeter sold under the name MDSC 2920 by the company TA Instruments, with a temperature rise of 5° C. or 10° C. per minute, according to standard ISO 11357-3:1999. The heat of fusion of the pasty compound is the amount of energy required to make the compound change from the solid state to the liquid state. It is expressed in J/g.

The liquid fraction of the pasty compound measured at 32° C. preferably represents from 40% to 100% by weight of the pasty compound and better still from 50% to 100% by weight of the pasty compound. When the liquid fraction of the pasty compound, measured at 32° C., is equal to 100%, the temperature of the end of the melting range of the pasty compound is less than or equal to 32° C.

The liquid fraction of the pasty compound measured at 32° C. is equal to the ratio of the heat of fusion consumed at 32° C. to the heat of fusion of the pasty compound. The heat of fusion consumed at 32° C. is calculated in the same way as the heat of fusion consumed at 23° C.

The pasty compound preferably has a hardness at 20° C. ranging from 0.001 MPa to 0.5 MPa and preferably from 0.002 MPa to 0.4 MPa.

The hardness is measured according to a method of penetration of a probe into a sample of compound and in particular using a texture analyzer (for example the TA-XT2i machine from Rheo) equipped with a stainless-steel cylinder 2 mm in diameter. The hardness measurement is performed at 20° C. at the center of five samples. The cylinder is introduced into each sample, the penetration depth being 0.3 mm. The recorded hardness value is that of the maximum peak.

The pasty compound is chosen from compounds of plant origin. A pasty compound may be obtained via synthesis from starting materials of plant origin.

The pasty compound may be chosen especially from isomerized jojoba oil such as the partially hydrogenated trans-isomerized jojoba oil manufactured or sold by the company Desert Whale under the commercial reference Iso-Jojoba-50®, orange wax, for instance the product sold under the reference Orange Peel Wax by the company Koster Keunen, cupuacu butter (Rain Forest RF3410 from the company Beraca Sabara), murumuru butter (Rain Forest RF3710 from the company Beraca Sabara), shea butter, partially hydrogenated olive oil, for instance the compound sold under the reference Beurrolive by the company Soliance, cocoa butter, mango oil, for instance Lipex 203 from the company Aarhuskarlshamn, and mixtures thereof.

Mention may also be made of mixtures of fatty acids comprising from 8 to 30 carbon atoms and of fatty alcohols comprising from 8 to 30 carbon atoms, such as mixtures of lauryl alcohol and methyl laurate, of stearyl alcohol and methyl palmitate or methyl behenate, such as the Purester range sold by the company Strahl & Pitsch, especially the lauryl laurate known under the trade name Purester 24.

Similarly, mention may be made of esters of a fatty acid comprising from 8 to 30 carbon atoms and of polyglyceryl comprising from 2 to 10 glyceryl units, such as the polyglyceryl-3 polyricinoleate sold by the company Aarhuskarlshamn under the name Akoline PGPR or alternatively a mixture of three jojoba ester waxes & *Helianthus annus* seed wax & *Acacia decurrens* extract and polyglyceryl, such as the product sold under the name Hydracire S or Acticire® by the company Gattefossé.

Mention may also be made of hydrogenated glycerol esters, for instance the product sold under the name Cegesoft HF 52 by the company Cognis (BASF), which is a mixture of hydrogenated rapeseed and palm oils, or the product sold under the name Softisan 100 Cremer by the company Oleo.

Mention may also be made of mixtures of monoester and/or diester of a fatty acid comprising from 8 to 18 carbon atoms and of mono- or polyglycerol, such as glyceryl stearate, for instance the glyceryl stearate sold under the reference Cutina GMS V by the company Cognis or the mixture of glyceryl monostearate and distearate sold by the company Stéarineries Dubois under the name Dub GMS 50/50.

When they are present, the amount of pasty compounds may range, for example, from 0.05% to 85% by weight, better still from 0.1% to 40% by weight, in particular from 0.5% to 10% by weight, relative to the total weight of the anhydrous composite material.

Waxes

Besides such a pasty fatty substance, the anhydrous composite material of the invention may also comprise at least one wax.

For the purposes of the present invention, the term "wax" means a lipophilic compound, which is solid at room temperature (25° C.), with a reversible solid/liquid change of state, having a melting point of greater than or equal to 30° C., which may be up to 120° C. In particular, the waxes have a melting point of greater than 30° C. and better still greater than 45° C.

For the purposes of the invention, the melting point corresponds to the temperature of the most endothermic peak observed on thermal analysis (differential scanning calorimetry or DSC) as described in standard ISO 11357-3; 1999. The melting point of the wax may be measured using a differential scanning calorimeter (DSC), for example the calorimeter sold under the name MDSC 2920 by the company TA Instruments.

The measurement protocol is as follows:

A 5 mg sample of wax placed in a crucible is subjected to a first temperature rise ranging from −20° C. to 100° C., at a heating rate of 10° C./minute, and then is cooled from 100° C. to −20° C. at a cooling rate of 10° C./minute and is finally subjected to a second temperature rise ranging from −20° C. to 100° C. at a heating rate of 5° C./minute. During the second temperature rise, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

For the purposes of the present invention, the term "hard wax" means a wax having, at 20° C., a hardness of greater than 5 MPa, in particular ranging from 5 to 30 MPa, preferably greater than 6 MPa and better still ranging from 6 to 25 MPa.

The hardness of the wax is determined by measuring the compressive force, measured at 20° C. using the texturometer sold under the name TA-XT2 by the company Rheo, equipped with a stainless-steel cylinder 2 mm in diameter, traveling at a measuring speed of 0.1 mm/second, and penetrating the wax to a penetration depth of 0.3 mm.

The measuring protocol is as follows: the wax is melted at a temperature equal to the melting point of the wax+10° C. The molten wax is poured into a container 25 mm in diameter and 20 mm deep. The wax is recrystallized at room temperature (25° C.) for 24 hours such that the surface of the wax is flat and smooth, and the wax is then stored for at least 1 hour at 20° C. before measuring the hardness or the tack.

The texturometer spindle is displaced at a speed of 0.1 mm/s, then penetrates the wax to a penetration depth of 0.3 mm. When the spindle has penetrated the wax to a depth of 0.3 mm, the spindle is held still for 1 second (corresponding to the relaxation time) and is then withdrawn at a speed of 0.5 mm/s.

The hardness value is the maximum compression force measured divided by the area of the texturometer cylinder in contact with the wax.

Waxes that may advantageously be used include waxes of plant origin such as beeswax, especially the product sold under the name White Beeswax SP 453P by the company Strahl & Pitsch or Cerabeil LOR by the company Baerlocher, black wheat wax such as the product sold by the company Codif, carnauba wax, candelilla wax, especially the commercial reference Candelilla Wax SP 75 G by the company Strahl & Pitsch, hydrogenated jojoba wax, sumach wax, the waxes obtained by hydrogenation of olive oil esterified with fatty alcohols bearing a $C_{12}$ to $C_{18}$ chain, sold by the company Sophim in the Phytowax range (12L44, 14L48, 16L55 and 18L57), rice bran wax, cetyl, stearyl and behenyl alcohols, laurel wax or ouricury wax.

Use may also be made of at least one ester of behenic acid and of glycerol, and in particular a mixture of esters of behenic acid and of glycerol, for instance the glyceryl dibehenate, tribehenin, glyceryl behenate mixture sold by the company Gattefossé under the reference Compritol 888 CG ATO.

When they are present, the waxes may be present in a content ranging from 0.01% to 40% by weight, preferably from 0.05% to 10% by weight and better still from 0.1% to 6% by weight relative to the total weight of the anhydrous composite material.

Oils

The anhydrous composite material according to the invention advantageously comprises at least one oil.

The term "oils" means fatty substances that are liquid at room temperature (25° C.) and atmospheric pressure.

As oils that may be used in the anhydrous composite material of the invention, examples that may be mentioned include:
  hydrocarbon-based oils, especially of plant origin, such as squalane, liquid triglycerides of fatty acids comprising from 4 to 30 carbon atoms, for instance heptanoic or octanoic acid triglycerides, or alternatively, for example, jojoba oil, babassu oil, sunflower oil, olive oil, coconut oil, Brazil nut oil, marula oil, corn oil, soybean oil, marrow oil, grapeseed oil, linseed oil, sesame seed oil, hazelnut oil, apricot oil, macadamia nut oil, arara oil, coriander oil, castor oil, avocado oil, caprylic/capric acid triglycerides, for instance those sold by the company Stéarineries Dubois or those sold under the names Miglyol 810, 812 and 818 by the company Dynamit Nobel, and shea butter oil;
  synthetic esters and ethers, especially of fatty acids and/or of fatty alcohols, for instance the oils of formulae $R^1COOR^2$ and $R^1OR^2$ in which $R^1$ represents a fatty acid residue or $R^1$ represents a fatty alcohol residue containing from 8 to 29 carbon atoms and $R^2$ represents a branched or unbranched hydrocarbon-based chain containing from 3 to 30 carbon atoms, for instance purcellin oil, 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate, triisocetyl citrate, and fatty alcohol heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate; mixtures thereof.

Mention may also be made of the following oils:
esters derived from the reaction of at least one fatty acid containing at least 6 carbon atoms, preferably from 6 to 26 carbon atoms, better still from 6 to 20 carbon atoms and even better still from 6 to 16 carbon atoms, and of at least one alcohol comprising from 1 to 17 carbon atoms and better still from 3 to 15 carbon atoms; mention may in particular be made of isopropyl myristate, such as the products sold under the name Palmester 1510 by the company KLK Oleo, under the name Lexol IPM-NF by the company Inolex Chemical Company or under the name Isopropyl Myristate by the company Cognis (BASF), isopropyl isostearate such as the product sold under the name Radia 7739 by the company Oleon, isopropyl palmitate, 2-ethylhexyl caprate/caprylate (or octyl caprate/caprylate), 2-ethylhexyl palmitate, isostearyl neopentanoate, isononyl isononanoate, hexyl laurate, lactic acid esters of fatty alcohols comprising 12 or 13 carbon atoms, and dicaprylyl carbonate, such as the product which is sold under the name Cetiol CC by the company Cognis;

fatty alcohol ethers comprising from 6 to 20 carbon atoms, preferably from 8 to 12 carbon atoms, even more preferentially from 8 to 10 carbon atoms. These ethers may be obtained from two different fatty alcohols or from two identical fatty alcohols. Preferably, they are obtained from two identical fatty alcohols such as capryl alcohol (also known as 1-octanol or n-octanol). The corresponding ether is then dicaprylyl ether, such as the product sold under the name Cetiol OE by the company Cognis;

glycerol ethers comprising from 6 to 12 carbon atoms, such as glyceryl 2-ethylhexyl ether (INCI name: ethylhexyl glycerol) such as Sensiva SC 50 from the company Schulke & Mayr GmbH. Mention may be made in particular of the mixture of esters of caprylic/capric acids and of $C_{12}$-$C_{18}$ fatty alcohols such as coco-caprylate/caprate sold under the name Cetiol LC by the company Cognis or under the name Dub 810 C by the company Stéarineries Dubois;

volatile linear alkanes, advantageously of plant origin, comprising from 7 to 17 carbon atoms, in particular from 9 to 15 carbon atoms and more particularly from 11 to 13 carbon atoms. As examples of volatile linear alkanes that are suitable for use in the invention, mention may be made of those described in patent application WO 2007/068 371 from the company Cognis. As examples of volatile linear alkanes that are suitable for use in the invention, mention may be made of n-nonane ($C_9$), n-decane ($C_{10}$), n-undecane ($C_{11}$), n-dodecane ($C_{12}$), n-tridecane ($C_{13}$), n-tetradecane ($C_{14}$), n-pentadecane ($C_{15}$), n-hexadecane ($C_{16}$) and n-heptadecane ($C_{17}$), and mixtures thereof. According to a particularly preferred embodiment, use will be made of a mixture of undecane ($C_{11}$) and of tridecane ($C_{13}$) such as the product sold under the reference Cetiol UT by the company Cognis. Mention may also be made of n-dodecane (Cu) and n-tetradecane ($C_{14}$) such as the products sold by Sasol under the respective references Parafol 12-97 and Parafol 14-97, and also mixtures thereof;

polyesters obtained by condensation of a dimer and/or trimer of a $C_8$-$C_{30}$ unsaturated fatty acid and of diol, for instance the polyesters of dilinoleic acid and of diol sold by Biosynthis under the name Viscoplast and especially the polymer bearing the INCI name dilinoleic acid/propanediol copolymer;
and mixtures thereof.

Use may also be made of Guerbet alcohols or of Guerbet alcohol derivatives, for instance esters of Guerbet alcohols and of $C_8$-$C_{30}$ fatty acid. Guerbet alcohols are obtained by converting an aliphatic primary alcohol into a beta-alkylenated alcohol dimer via the following chemical reaction:

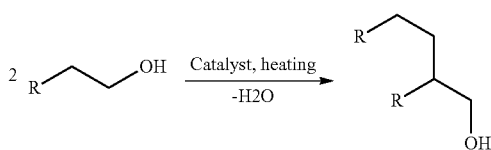

This reaction requires the presence of a base such as alkali metal hydroxides or alkali metal alkoxides, a catalyst such as Raney nickel, and high temperatures.

As Guerbet alcohols or esters of $C_8$-$C_{30}$ fatty acids and of Guerbet alcohols, mention may be made especially of octyldodecanol and octyldodecanol esters such as octyldodecyl myristate. Mention may be made in particular of octyldodecanol, such as the product sold under the name Eutanol G by the company Cognis (BASF) and the octyldodecyl myristate sold under the name Dub MOD by the company Gattefossé.

According to a preferred embodiment of the invention, the fatty phase of the anhydrous composite material comprises at least one oil, preferably at least 20% by weight of oil(s), and better still at least 25% by weight of oil(s), relative to the total weight of the material.

In particular, the fatty phase of the anhydrous composite material may have a total oil content ranging from 40% to 85% by weight, preferably from 50% to 85% by weight and better still from 54% to 77% by weight relative to the total weight of the anhydrous composite material.

According to a particular embodiment of the invention, the fatty phase of the anhydrous composite material comprises at least one oil chosen from hydrocarbon-based oils, such as triglycerides, Guerbet alcohols, esters of a $C_8$-$C_{30}$ fatty acid and of a Guerbet alcohol, fatty alcohol ethers comprising from 6 to 20 carbon atoms, and linear $C_7$-$C_{17}$ alkanes, and mixtures thereof.

According to a particular embodiment, the fatty phase of the anhydrous composite material comprises from 40% to 85% by weight of at least one oil chosen from hydrocarbon-based oils, such as triglycerides, Guerbet alcohols, esters of a $C_8$-$C_{30}$ fatty acid and of a Guerbet alcohol, and linear $C_7$-$C_{17}$ alkanes, and mixtures thereof.

According to another particular embodiment of the invention, the fatty phase of the anhydrous composite material comprises from 40% to 85% by weight and preferably from 45% to 75% by weight, relative to the total weight of the anhydrous composite material, of at least one oil chosen from hydrocarbon-based oils, preferably triglycerides, Guerbet alcohols and esters of a $C_8$-$C_{30}$ fatty acid and of a Guerbet alcohol, and from 5% to 25% by weight and preferably from 5% to 10% by weight, relative to the total weight of the composition, of at least one oil chosen from linear $C_7$-$C_{17}$ alkanes.

According to a particular embodiment of the invention, the fatty phase of the anhydrous composite material comprises at least two different oils, and preferably at least 15% to 85% by weight, relative to the total weight of the material, of an oil chosen from hydrocarbon-based oils, preferably triglycerides, Guerbet alcohols and esters of a $C_8$-$C_{30}$ fatty acid and of a Guerbet alcohol, and at least 5% to 25% by weight and preferably at least 5% to 10% by weight, relative to the total weight of the material, of at least one oil chosen from linear $C_7$-$C_{17}$ alkanes.

According to a particular embodiment, the fatty phase of the anhydrous composite material also comprises at least one wax, chosen in particular from candelilla wax, carnauba wax, beeswax, hydrogenated jojoba wax, black wheat wax, sumach wax, waxes obtained by hydrogenation of olive oil esterified with fatty alcohols bearing a $C_{12}$ to $C_{18}$ chain, rice bran wax, fatty alcohols bearing a $C_{12}$ to $C_{18}$ chain such as cetyl alcohol, stearyl alcohol and behenyl alcohol, laurel wax, ouricury wax, an ester of behenic acid and of glycerol, and in particular a mixture of esters of behenic acid and of glycerol, for instance the mixture glyceryl dibehenate, tribehenin and glyceryl behenate, and is preferably candelilla wax.

According to a first specific embodiment of the invention, the anhydrous composite material is formed from at least:
  3% to 15% by weight, relative to the total weight of the material, of at least one lipophilic gelling agent chosen from triesters of a $C_8$-$C_{30}$ fatty acid and of mono- or polyglycerol, such as glyceryl trihydroxystearate;
  10% to 50% by weight of fillers, relative to the total weight of the material, including at least 5% by weight of a first filler chosen from porous spherical silica microparticles and spherical cellulose particles, and at least 5% by weight of a second filler different from the first, chosen from spherical cellulose particles; and
  40% to 85% by weight of at least one fatty phase, relative to the total weight of the material, comprising from 25% to 58% by weight, relative to the total weight of the material, of at least one oil chosen from hydrocarbon-based oils, preferably triglycerides, and from 5% to 10% by weight of at least one oil chosen from linear $C_7$-$C_{17}$ alkanes.

According to another specific embodiment of the invention, the anhydrous composite material is formed from at least:
  3% to 15% by weight, relative to the total weight of the material, of at least one lipophilic gelling agent chosen from triesters of a $C_8$-$C_{30}$ fatty acid and of mono- or polyglycerol, such as glyceryl trihydroxystearate;
  10% to 50% by weight of fillers, relative to the total weight of the material, including at least 5% by weight of a first filler chosen from porous spherical silica microparticles, and at least 5% by weight of a second filler chosen from spherical cellulose particles; and
  40% to 85% by weight of at least one fatty phase, relative to the total weight of the material, comprising from 25% to 55% by weight, relative to the total weight of the material, of at least one oil chosen from hydrocarbon-based oils, preferably triglycerides, from 5% to 10% by weight of at least one oil chosen from linear $C_7$-$C_{17}$ alkanes, and from 3% to 10% by weight of a wax, preferably a candelilla wax.

According to another specific embodiment of the invention, the anhydrous composite material is formed from at least:
  from 3% to 15% by weight of at least one lipophilic gelling agent chosen from fatty acid esters of dextrin, preferably dextrin palmitate;
  from 10% to 50% by weight of fillers including at least 5% by weight of porous spherical silica microparticles and at least 5% by weight of powder of an N-acylamino acid bearing a $C_8$-$C_{22}$ acyl group, preferably with a mass ratio R of silica/N-acylamino acid bearing a $C_8$-$C_{22}$ acyl group of greater than or equal to 0.75, preferably between 0.75 and 3; and from 40% to 85% by weight of at least one fatty phase comprising at least one oil chosen from hydrocarbon-based oils, such as triglycerides, Guerbet alcohols, esters of a $C_8$-$C_{30}$ fatty acid and of a Guerbet alcohol, and linear $C_7$-$C_{17}$ alkanes;

the weight amounts being given relative to the total weight of the anhydrous composite material.

According to another specific embodiment of the invention, the anhydrous composite material is formed from at least:

from 3% to 15% by weight of at least one lipophilic gelling agent chosen from fatty acid esters of dextrin, preferably dextrin palmitate;

from 10% to 50% by weight of fillers including at least 5% by weight of porous spherical silica microparticles and at least 5% by weight of powders of an N-acylamino acid bearing a $C_8$-$C_{22}$ acyl group, preferably with a mass ratio R of silica/N-acylamino acid bearing a $C_8$-$C_{22}$ acyl group of greater than or equal to 0.75, and even more preferentially between 0.75 and 3; and from 40% to 85% by weight of at least one fatty phase comprising at least one oil chosen from hydrocarbon-based oils, preferably triglycerides;

the weight amounts being given relative to the total weight of the anhydrous composite material.

Preferably, the anhydrous composite material is formed from at least:

from 3% to 15% by weight of at least one lipophilic gelling agent chosen from fatty acid esters of dextrin, preferably dextrin palmitate;

from 10% to 50% by weight of fillers including at least 5% by weight of porous spherical silica microparticles and at least 5% by weight of powders of an N-acylamino acid bearing a $C_8$-$C_{22}$ acyl group, preferably with a mass ratio R of silica/N-acylamino acid bearing a $C_8$-$C_{22}$ acyl group of greater than or equal to 0.75, and even more preferentially between 0.75 and 3; and from 40% to 85% by weight of at least one fatty phase comprising from 25% to 48% by weight of at least one oil chosen from hydrocarbon-based oils, preferably triglycerides;

the weight amounts being given relative to the total weight of the anhydrous composite material.

According to another specific embodiment of the invention, the anhydrous composite material is formed from at least:

from 3% to 15% by weight of at least one lipophilic gelling agent chosen from fatty acid esters of dextrin, preferably dextrin palmitate;

from 10% to 50% by weight of fillers including at least 5% by weight of porous spherical silica microparticles and at least 5% by weight of powders of an N-acylamino acid bearing a $C_8$-$C_{22}$ acyl group, preferably with a mass ratio R of silica/N-acylamino acid bearing a $C_8$-$C_{22}$ acyl group of greater than or equal to 0.75, and even more preferentially between 0.75 and 3; and from 40% to 85% by weight of at least one fatty phase comprising at least one oil chosen from hydrocarbon-based oils, preferably triglycerides and at least one oil chosen from linear $C_7$-$C_{17}$ alkanes;

the weight amounts being given relative to the total weight of the anhydrous composite material.

Preferably, the anhydrous composite material is formed from at least:

from 3% to 15% by weight of at least one lipophilic gelling agent chosen from fatty acid esters of dextrin, preferably dextrin palmitate;

from 10% to 50% by weight of fillers including at least 5% by weight of porous spherical silica microparticles and at least 5% by weight of powders of an N-acylamino acid bearing a $C_8$-$C_{22}$ acyl group, preferably with a mass ratio R of silica/N-acylamino acid bearing a $C_8$-$C_{22}$ acyl group of greater than or equal to 0.75, and even more preferentially between 0.75 and 3; and from 40% to 85% by weight of at least one fatty phase comprising from 25% to 48% by weight of at least one oil chosen from hydrocarbon-based oils, preferably triglycerides and from 5% to 25% by weight and preferably from 5% to 10% by weight of at least one oil chosen from linear $C_7$-$C_{17}$ alkanes;

the weight amounts being given relative to the total weight of the anhydrous composite material.

According to another specific embodiment of the invention, the anhydrous composite material is formed from at least:

from 3% to 15% by weight of at least one lipophilic gelling agent chosen from fatty acid esters of dextrin, preferably dextrin palmitate;

from 10% to 50% by weight of fillers including at least 5% by weight of porous spherical silica microparticles and at least 5% by weight of spherical cellulose particles, preferably with a mass ratio R of silica/cellulose of greater than or equal to 0.75, and even more preferentially between 0.75 and 3; and from 40% to 85% by weight of at least one fatty phase comprising at least one oil chosen from hydrocarbon-based oils, preferably triglycerides, Guerbet alcohols, esters of a $C_8$-$C_{30}$ fatty acid and of a Guerbet alcohol, and linear $C_7$-$C_{17}$ alkanes;

the weight amounts being given relative to the total weight of the anhydrous composite material.

According to another specific embodiment of the invention, the anhydrous composite material is formed from at least:

from 3% to 15% by weight of at least one lipophilic gelling agent chosen from fatty acid esters of dextrin, preferably dextrin palmitate;

from 10% to 50% by weight of fillers including at least 5% by weight of porous spherical silica microparticles and at least 5% by weight of spherical cellulose particles, preferably with a mass ratio R of silica/cellulose of greater than or equal to 0.75, and even more preferentially between 0.75 and 3; and from 40% to 85% by weight of at least one fatty phase comprising at least one oil chosen from Guerbet alcohols and esters of a $C_8$-$C_{30}$ fatty acid and of a Guerbet alcohol;

the weight amounts being given relative to the total weight of the anhydrous composite material.

Preferably, the anhydrous composite material is formed from at least:

from 3% to 15% by weight of at least one lipophilic gelling agent chosen from fatty acid esters of dextrin, preferably dextrin palmitate;

from 10% to 50% by weight of fillers including at least 5% by weight of porous spherical silica microparticles and at least 5% by weight of spherical cellulose particles, preferably with a mass ratio R of silica/cellulose of greater than or equal to 0.75, and even more preferentially between 0.75 and 3; and from 40% to 85% by weight of at least one fatty phase comprising from 25% to 70% by weight and preferably from 25% to 48% by weight of at least one oil chosen from Guerbet alcohols and esters of a $C_8$-$C_{30}$ fatty acid and of a Guerbet alcohol;

the weight amounts being given relative to the total weight of the anhydrous composite material.

According to another specific embodiment of the invention, the anhydrous composite material is formed from at least:

from 3% to 15% by weight of at least one lipophilic gelling agent chosen from triesters of a $C_8$-$C_{30}$ fatty acid and of mono- or polyglycerol, such as glyceryl trihydroxystearate;

from 10% to 50% by weight of fillers including at least 5% by weight of porous spherical silica microparticles and at least 5% by weight of spherical cellulose particles, preferably with a mass ratio R of silica/cellulose of greater than or equal to 0.75, and even more preferentially between 0.75 and 3; and from 40% to 85% by weight of at least one fatty phase comprising at least one oil chosen from hydrocarbon-based oils, preferably triglycerides, Guerbet alcohols, esters of a $C_8$-$C_{30}$ fatty acid and of a Guerbet alcohol, and linear $C_7$-$C_{17}$ alkanes;

the weight amounts being given relative to the total weight of the anhydrous composite material.

According to another specific embodiment of the invention, the anhydrous composite material is formed from at least:

from 3% to 15% by weight of at least one lipophilic gelling agent chosen from triesters of a $C_8$-$C_{30}$ fatty acid and of mono- or polyglycerol, such as glyceryl trihydroxystearate;

from 10% to 50% by weight of fillers including at least 5% by weight of porous spherical silica microparticles and at least 5% by weight of spherical cellulose particles, preferably with a mass ratio R of silica/cellulose of greater than or equal to 0.75, and even more preferentially between 0.75 and 3; and from 40% to 85% by weight of at least one fatty phase comprising at least one oil chosen from hydrocarbon-based oils, preferably triglycerides and at least one oil chosen from linear $C_7$-$C_{17}$ alkanes;

the weight amounts being given relative to the total weight of the anhydrous composite material.

Preferably, the anhydrous composite material is formed from at least:

from 3% to 15% by weight of at least one lipophilic gelling agent chosen from triesters of a $C_8$-$C_{30}$ fatty acid and of mono- or polyglycerol, such as glyceryl trihydroxystearate;

from 10% to 50% by weight of fillers including at least 5% by weight of porous spherical silica microparticles and at least 5% by weight of spherical cellulose particles, preferably with a mass ratio R of silica/cellulose of greater than or equal to 0.75, and even more preferentially between 0.75 and 3; and from 40% to 85% by weight of at least one fatty phase comprising from 25% to 48% by weight of at least one oil chosen from hydrocarbon-based oils, preferably triglycerides and from 5% to 25% by weight and preferably from 5% to 10% by weight of at least one oil chosen from linear $C_7$-$C_{17}$ alkanes;

the weight amounts being given relative to the total weight of the anhydrous composite material.

According to another specific embodiment of the invention, the anhydrous composite material is formed from at least:

from 3% to 15% by weight of at least one lipophilic gelling agent chosen from fatty acid esters of dextrin, preferably dextrin myristate;

from 10% to 50% by weight of fillers including at least 5% by weight of powders of an N-acylamino acid bearing a $C_8$-$C_{22}$ acyl group and at least 5% by weight of spherical cellulose particles; and from 40% to 85% by weight of at least one fatty phase comprising at least one oil chosen from hydrocarbon-based oils, preferably triglycerides, Guerbet alcohols, esters of a $C_8$-$C_{30}$ fatty acid and of a Guerbet alcohol, and linear $C_7$-$C_{17}$ alkanes;

the weight amounts being given relative to the total weight of the anhydrous composite material.

According to another specific embodiment of the invention, the anhydrous composite material is formed from at least:

from 3% to 15% by weight of at least one lipophilic gelling agent chosen from fatty acid esters of dextrin, preferably dextrin myristate;

from 10% to 50% by weight of fillers including at least 5% by weight of powders of an N-acylamino acid bearing a $C_8$-$C_{22}$ acyl group and at least 5% by weight of spherical cellulose particles; and from 40% to 85% by weight of at least one fatty phase comprising at least one oil chosen from Guerbet alcohols and esters of a $C_8$-$C_{30}$ fatty acid and of a Guerbet alcohol;

the weight amounts being given relative to the total weight of the anhydrous composite material.

Preferably, the anhydrous composite material is formed from at least:

from 3% to 15% by weight of at least one lipophilic gelling agent chosen from fatty acid esters of dextrin, preferably dextrin myristate;

from 10% to 50% by weight of fillers including at least 5% by weight of powders of an N-acylamino acid bearing a $C_8$-$C_{22}$ acyl group and at least 5% by weight of spherical cellulose particles; and from 40% to 85% by weight of at least one fatty phase comprising from 5% to 25% by weight and preferably from 5% to 15% by weight of at least one oil chosen from Guerbet alcohols and esters of a $C_8$-$C_{30}$ fatty acid and of a Guerbet alcohol;

the weight amounts being given relative to the total weight of the anhydrous composite material.

According to another specific embodiment of the invention, the anhydrous composite material is formed from at least:

from 3% to 15% by weight of at least one lipophilic gelling agent chosen from fatty acid esters of dextrin, preferably dextrin myristate;

from 10% to 50% by weight of fillers including at least 5% by weight of porous spherical silica microparticles and at least 5% by weight of spherical cellulose particles; and from 40% to 85% by weight of at least one fatty phase comprising at least one oil chosen from hydrocarbon-based oils, preferably triglycerides, Guerbet alcohols, esters of a $C_8$-$C_{30}$ fatty acid and of a Guerbet alcohol, and linear $C_7$-$C_{17}$ alkanes;

the weight amounts being given relative to the total weight of the anhydrous composite material.

According to another specific embodiment of the invention, the anhydrous composite material is formed from at least:
- from 3% to 15% by weight of at least one lipophilic gelling agent chosen from fatty acid esters of dextrin, preferably dextrin myristate;
- from 10% to 50% by weight of fillers including at least 5% by weight of porous spherical silica microparticles and at least 5% by weight of spherical cellulose particles; and
- from 40% to 85% by weight of at least one fatty phase comprising at least one oil chosen from Guerbet alcohols and esters of a $C_8$-$C_{30}$ fatty acid and of a Guerbet alcohol;

the weight amounts being given relative to the total weight of the anhydrous composite material.

Preferably, the anhydrous composite material is formed from at least:
- from 3% to 15% by weight of at least one lipophilic gelling agent chosen from fatty acid esters of dextrin, preferably dextrin myristate;
- from 10% to 50% by weight of fillers including at least 5% by weight of porous spherical silica microparticles and at least 5% by weight of spherical cellulose particles; and
- from 40% to 85% by weight of at least one fatty phase comprising from 5% to 25% by weight and preferably from 5% to 15% by weight of at least one oil chosen from Guerbet alcohols and esters of a $C_8$-$C_{30}$ fatty acid and of a Guerbet alcohol;

the weight amounts being given relative to the total weight of the anhydrous composite material.

According to another specific embodiment of the invention, the anhydrous composite material is formed from at least:
- from 3% to 15% by weight of at least one lipophilic gelling agent chosen from fatty acid esters of dextrin, preferably dextrin myristate;
- from 15% to 50% by weight of fillers including at least three fillers that are different from each other, one of which is chosen from inorganic fillers and the other two are chosen from organic fillers, preferably at least three fillers that are different from each other, one of which is chosen from porous spherical silica particles, in particular porous spherical silica microparticles, and the other two are chosen from spherical cellulose particles, powders of an N-acylamino acid bearing a $C_8$-$C_{22}$ acyl group and polyamide particles, preferably spherical cellulose particles and powders of an N-acylamino acid bearing a $C_8$-$C_{22}$ acyl group; and
- from 40% to 85% by weight of at least one fatty phase comprising at least one oil chosen from hydrocarbon-based oils, preferably triglycerides, Guerbet alcohols, esters of a $C_8$-$C_{30}$ fatty acid and of a Guerbet alcohol, and linear $C_7$-$C_{17}$ alkanes;

the weight amounts being given relative to the total weight of the anhydrous composite material.

According to another specific embodiment of the invention, the anhydrous composite material is formed from at least:
- from 3% to 15% by weight of at least one lipophilic gelling agent chosen from fatty acid esters of dextrin, preferably dextrin myristate;
- from 15% to 50% by weight of fillers including at least three fillers that are different from each other, one of which is chosen from inorganic fillers and the other two are chosen from organic fillers, preferably at least three fillers that are different from each other, one of which is chosen from porous spherical silica particles, in particular porous spherical silica microparticles, and the other two are chosen from spherical cellulose particles, powders of an N-acylamino acid bearing a $C_8$-$C_{22}$ acyl group and polyamide particles, preferably spherical cellulose particles and powders of an N-acylamino acid bearing a $C_8$-$C_{22}$ acyl group; and
- from 40% to 85% by weight of at least one fatty phase comprising at least one oil chosen from Guerbet alcohols and esters of a $C_8$-$C_{30}$ fatty acid and of a Guerbet alcohol;

the weight amounts being given relative to the total weight of the anhydrous composite material.

Preferably, the anhydrous composite material is formed from at least:
- from 3% to 15% by weight of at least one lipophilic gelling agent chosen from fatty acid esters of dextrin, preferably dextrin myristate;
- from 15% to 50% by weight of fillers including at least three fillers that are different from each other, one of which is chosen from inorganic fillers and the other two are chosen from organic fillers, preferably at least three fillers that are different from each other, one of which is chosen from porous spherical silica particles, in particular porous spherical silica microparticles, and the other two are chosen from spherical cellulose particles, powders of an N-acylamino acid bearing a $C_8$-$C_{22}$ acyl group and polyamide particles, preferably spherical cellulose particles and powders of an N-acylamino acid bearing a $C_8$-$C_{22}$ acyl group; and
- from 40% to 85% by weight of at least one fatty phase comprising from 5% to 25% by weight, preferably from 5% to 15% by weight and even more preferentially from 5% to 10% by weight of at least one oil chosen from Guerbet alcohols and esters of a $C_8$-$C_{30}$ fatty acid and of a Guerbet alcohol;

the weight amounts being given relative to the total weight of the anhydrous composite material.

Preferably, the anhydrous composite material is formed from at least:
- from 3% to 15% by weight of at least one lipophilic gelling agent chosen from fatty acid esters of dextrin, preferably dextrin myristate;
- from 15% to 50% by weight of at least three fillers that are different from each other including at least 5% by weight of a first inorganic filler chosen from porous spherical silica particles, in particular porous spherical silica microparticles, at least 5% by weight of at least a second organic filler chosen from spherical cellulose particles, and at least 5% by weight of a third organic filler chosen from powders of an N-acylamino acid bearing a $C_8$-$C_{22}$ acyl group; and
- from 40% to 85% by weight of at least one fatty phase comprising from 5% to 25% by weight, preferably from 5% to 15% by weight and even more preferentially from 5% to 10% by weight of at least one oil chosen from Guerbet alcohols and esters of a $C_8$-$C_{30}$ fatty acid and of a Guerbet alcohol;

the weight amounts being given relative to the total weight of the anhydrous composite material.

According to another specific embodiment of the invention, the anhydrous composite material is formed from at least:

from 3% to 15% by weight of at least one lipophilic gelling agent chosen from fatty acid esters of dextrin, preferably dextrin palmitate;
from 20% to 50% by weight and preferably from 30% to 40% by weight of at least one filler, preferably a single filler, chosen from porous spherical silica particles; and
from 40% to 85% by weight of at least one fatty phase containing at least 25% by weight of at least one oil chosen from hydrocarbon-based oils, preferably triglycerides, Guerbet alcohols, esters of a $C_8$-$C_{30}$ fatty acid and of a Guerbet alcohol, fatty alcohol ethers comprising from 6 to 20 carbon atoms, and linear $C_7$-$C_{17}$ alkanes;

the weight amounts being given relative to the total weight of the anhydrous composite material.

According to another specific embodiment of the invention, the anhydrous composite material is formed from at least:
from 3% to 15% by weight of at least one lipophilic gelling agent chosen from fatty acid esters of dextrin, preferably dextrin palmitate;
from 20% to 50% by weight and preferably from 30% to 40% by weight of at least one filler, preferably a single filler, chosen from porous spherical silica particles; and
from 40% to 85% by weight of at least one fatty phase comprising at least 25% by weight of at least one oil chosen from Guerbet alcohols and esters of a $C_8$-$C_{30}$ fatty acid and of a Guerbet alcohol;

the weight amounts being given relative to the total weight of the anhydrous composite material.

Preferably, the anhydrous composite material is formed from at least:
from 3% to 15% by weight of at least one lipophilic gelling agent chosen from fatty acid esters of dextrin, preferably dextrin palmitate;
from 30% to 40% by weight of at least one filler, preferably a single filler, chosen from porous spherical silica particles; and
from 40% to 85% by weight of at least one fatty phase comprising at least 30% by weight of at least one oil chosen from Guerbet alcohols and esters of a $C_8$-$C_{30}$ fatty acid and of a Guerbet alcohol;

the weight amounts being given relative to the total weight of the anhydrous composite material.

According to another specific embodiment of the invention, the anhydrous composite material is formed from at least:
from 3% to 15% by weight of at least one lipophilic gelling agent chosen from fatty acid esters of dextrin, preferably dextrin palmitate;
from 20% to 50% by weight and preferably from 30% to 40% by weight of at least one filler, preferably a single filler, chosen from porous spherical silica particles; and
from 40% to 85% by weight of at least one fatty phase containing at least 25% by weight of at least one oil chosen from hydrocarbon-based oils, preferably triglycerides;

the weight amounts being given relative to the total weight of the anhydrous composite material.

Preferably, the anhydrous composite material is formed from at least:
from 3% to 15% by weight of at least one lipophilic gelling agent chosen from fatty acid esters of dextrin, preferably dextrin palmitate;
from 30% to 40% by weight of at least one filler, preferably a single filler, chosen from porous spherical silica particles; and
from 40% to 85% by weight of at least one fatty phase containing at least 30% by weight of at least one oil chosen from hydrocarbon-based oils, preferably triglycerides;

the weight amounts being given relative to the total weight of the anhydrous composite material.

According to another specific embodiment of the invention, the anhydrous composite material is formed from at least:
from 3% to 15% by weight of at least one lipophilic gelling agent chosen from fatty acid esters of dextrin, preferably dextrin palmitate;
from 20% to 50% by weight and preferably from 30% to 40% by weight of at least one filler chosen from porous spherical silica particles; and
from 40% to 85% by weight of at least one fatty phase containing at least 25% by weight of at least two oils, one of which is chosen from hydrocarbon-based oils, preferably triglycerides, and the other is chosen from linear $C_7$-$C_{17}$ alkanes;

the weight amounts being given relative to the total weight of the anhydrous composite material.

Preferably, the anhydrous composite material is formed from at least:
from 3% to 15% by weight of at least one lipophilic gelling agent chosen from fatty acid esters of dextrin, preferably dextrin palmitate;
from 30% to 40% by weight of at least one filler chosen from porous spherical silica particles; and
from 40% to 85% by weight of at least one fatty phase containing at least 25% by weight of at least one oil chosen from hydrocarbon-based oils, preferably triglycerides, and at least 5% by weight of at least one oil chosen from linear $C_7$-$C_{17}$ alkanes;

the weight amounts being given relative to the total weight of the anhydrous composite material.

According to another specific embodiment of the invention, the anhydrous composite material is formed from at least:
from 3% to 15% by weight of at least one lipophilic gelling agent chosen from triesters of a $C_8$-$C_{30}$ fatty acid and of mono- or polyglycerol, such as glyceryl trihydroxystearate;
from 20% to 50% by weight and preferably from 30% to 40% by weight of at least one filler chosen from powders of an N-acylamino acid bearing a $C_8$-$C_{22}$ acyl group; and
from 40% to 85% by weight of at least one fatty phase containing at least 25% by weight of at least one oil chosen from hydrocarbon-based oils, preferably triglycerides, Guerbet alcohols, esters of a $C_8$-$C_{30}$ fatty acid and of a Guerbet alcohol, fatty alcohol ethers comprising from 6 to 20 carbon atoms, and linear $C_7$-$C_{17}$ alkanes;

the weight amounts being given relative to the total weight of the anhydrous composite material.

According to another specific embodiment of the invention, the anhydrous composite material is formed from at least:
from 3% to 15% by weight of at least one lipophilic gelling agent chosen from triesters of a $C_8$-$C_{30}$ fatty acid and of mono- or polyglycerol, such as glyceryl trihydroxystearate;
from 20% to 50% by weight and preferably from 30% to 40% by weight of at least one filler chosen from powders of an N-acylamino acid bearing a $C_8$-$C_{22}$ acyl group; and from 40% to 85% by weight of at least one fatty phase containing at least 25% by weight of at least two oils, one of which is chosen from hydrocarbon-based oils, preferably triglycerides, and the other is chosen from linear $C_7$-$C_{17}$ alkanes;

the weight amounts being given relative to the total weight of the anhydrous composite material.

Preferably, the anhydrous composite material is formed from at least:
from 3% to 15% by weight of at least one lipophilic gelling agent chosen from triesters of a $C_8$-$C_{30}$ fatty acid and of mono- or polyglycerol, such as glyceryl trihydroxystearate;
from 30% to 40% by weight of at least one filler chosen from powders of an N-acylamino acid bearing a $C_8$-$C_{22}$ acyl group; and
from 45% to 85% by weight of at least one fatty phase containing at least 40% by weight of at least one oil chosen from hydrocarbon-based oils, preferably triglycerides, and at least 5% by weight of at least one oil chosen from linear $C_7$-$C_{17}$ alkanes;

the weight amounts being given relative to the total weight of the anhydrous composite material.

According to another specific embodiment of the invention, the anhydrous composite material is formed from at least:
from 3% to 15% by weight of at least one lipophilic gelling agent chosen from triesters of a fatty acid and of mono- or polyglycerol, such as glyceryl trihydroxystearate;
from 20% to 50% by weight and preferably from 30% to 40% by weight of at least one filler chosen from powders of an N-acylamino acid bearing a $C_8$-$C_{22}$ acyl group; and
from 40% to 85% by weight of at least one fatty phase containing at least 25% by weight of at least one oil chosen from fatty alcohol ethers comprising from 6 to 20 carbon atoms;

the weight amounts being given relative to the total weight of the anhydrous composite material.

Preferably, the anhydrous composite material is formed from at least:
from 3% to 15% by weight of at least one lipophilic gelling agent chosen from triesters of a fatty acid and of mono- or polyglycerol, such as glyceryl trihydroxystearate;
from 30% to 40% by weight of at least one filler chosen from powders of an N-acylamino acid bearing a $C_8$-$C_{22}$ acyl group; and
from 40% to 85% by weight of at least one fatty phase containing at least 25% by weight of at least one oil chosen from fatty alcohol ethers comprising from 6 to 20 carbon atoms;

the weight amounts being given relative to the total weight of the anhydrous composite material.

According to another specific embodiment of the invention, the anhydrous composite material is formed from at least:
from 3% to 15% by weight of at least one lipophilic gelling agent chosen from fatty acid esters of dextrin, preferably dextrin myristate;
from 20% to 50% by weight and preferably from 30% to 40% by weight of at least one filler chosen from powders of an N-acylamino acid bearing a $C_8$-$C_{22}$ acyl group; and
from 40% to 85% by weight of at least one fatty phase containing at least 25% by weight of at least one oil chosen from hydrocarbon-based oils, preferably triglycerides, Guerbet alcohols, esters of a $C_8$-$C_{30}$ fatty acid and of a Guerbet alcohol, fatty alcohol ethers comprising from 6 to 20 carbon atoms, and linear $C_7$-$C_{17}$ alkanes;

the weight amounts being given relative to the total weight of the anhydrous composite material.

According to another specific embodiment of the invention, the anhydrous composite material is formed from at least:
from 3% to 15% by weight of at least one lipophilic gelling agent chosen from fatty acid esters of dextrin, preferably dextrin myristate;
from 20% to 50% by weight and preferably from 30% to 40% by weight of at least one filler chosen from powders of an N-acylamino acid bearing a $C_8$-$C_{22}$ acyl group; and
from 40% to 85% by weight of at least one fatty phase comprising at least 25% by weight of at least one oil chosen from Guerbet alcohols and esters of a $C_8$-$C_{30}$ fatty acid and of a Guerbet alcohol;

the weight amounts being given relative to the total weight of the anhydrous composite material.

Preferably, the anhydrous composite material is formed from at least:
from 3% to 15% by weight of at least one lipophilic gelling agent chosen from fatty acid esters of dextrin, preferably dextrin myristate;
from 30% to 40% by weight of at least one filler chosen from powders of an N-acylamino acid bearing a $C_8$-$C_{22}$ acyl group; and
from 50% to 85% by weight of at least one fatty phase comprising at least 50% by weight of at least one oil chosen from Guerbet alcohols and esters of a $C_8$-$C_{30}$ fatty acid and of a Guerbet alcohol;

the weight amounts being given relative to the total weight of the anhydrous composite material.

According to another specific embodiment of the invention, the anhydrous composite material is formed from at least:
from 3% to 15% by weight of at least one lipophilic gelling agent chosen from fatty acid esters of dextrin, preferably dextrin myristate;
from 20% to 50% by weight and preferably from 20% to 30% by weight of at least one filler chosen from powders of an N-acylamino acid bearing a $C_8$-$C_{22}$ acyl group; and
from 40% to 85% by weight of at least one fatty phase containing at least 25% by weight of at least one oil chosen from hydrocarbon-based oils, preferably triglycerides;

the weight amounts being given relative to the total weight of the anhydrous composite material.

Preferably, the anhydrous composite material is formed from at least:
from 3% to 15% by weight of at least one lipophilic gelling agent chosen from fatty acid esters of dextrin, preferably dextrin myristate;
from 20% to 30% by weight of at least one filler chosen from powders of an N-acylamino acid bearing a $C_8$-$C_{22}$ acyl group; and
from 60% to 85% by weight of at least one fatty phase containing at least 60% by weight of at least one oil chosen from hydrocarbon-based oils, preferably triglycerides;

the weight amounts being given relative to the total weight of the anhydrous composite material.

According to another specific embodiment of the invention, the anhydrous composite material is formed from at least:
- from 3% to 15% by weight of at least one lipophilic gelling agent chosen from triesters of a fatty acid and of mono- or polyglycerol, such as glyceryl trihydroxystearate;
- from 20% to 50% by weight of at least one filler chosen from powders of an N-acylamino acid bearing a $C_8$-$C_{22}$ acyl group; and
- from 40% to 85% by weight of at least one fatty phase containing at least 20% by weight of at least one oil chosen from hydrocarbon-based oils, preferably triglycerides, Guerbet alcohols, esters of a $C_8$-$C_{30}$ fatty acid and of a Guerbet alcohol, fatty alcohol ethers comprising from 6 to 20 carbon atoms, and linear $C_7$-$C_{17}$ alkanes;

the weight amounts being given relative to the total weight of the anhydrous composite material.

According to another specific embodiment of the invention, the anhydrous composite material is formed from at least:
- from 3% to 15% by weight of at least one lipophilic gelling agent chosen from triesters of a fatty acid and of mono- or polyglycerol, such as glyceryl trihydroxystearate;
- from 20% to 50% by weight and preferably from 20% to 30% by weight of at least one filler chosen from powders of an N-acylamino acid bearing a $C_8$-$C_{22}$ acyl group; and
- from 40% to 85% by weight of at least one fatty phase containing at least 20% by weight of at least one oil chosen from linear $C_7$-$C_{17}$ alkanes;

the weight amounts being given relative to the total weight of the anhydrous composite material.

Preferably, the anhydrous composite material is formed from at least:
- from 3% to 15% by weight of at least one lipophilic gelling agent chosen from triesters of a fatty acid and of mono- or polyglycerol, such as glyceryl trihydroxystearate;
- from 20% to 30% by weight of at least one filler chosen from powders of an N-acylamino acid bearing a $C_8$-$C_{22}$ acyl group; and
- from 40% to 85% by weight of at least one fatty phase containing at least 20% by weight of at least one oil chosen from linear $C_7$-$C_{17}$ alkanes;

the weight amounts being given relative to the total weight of the anhydrous composite material.

According to another specific embodiment of the invention, the anhydrous composite material is formed from at least:
- from 3% to 15% by weight of at least one lipophilic gelling agent chosen from fatty acid esters of dextrin, preferably dextrin myristate;
- from 20% to 50% by weight and preferably from 40% to 50% by weight of at least one filler chosen from spherical cellulose particles; and
- from 40% to 85% by weight of at least one fatty phase containing at least 25% by weight of at least one oil chosen from hydrocarbon-based oils, preferably triglycerides, Guerbet alcohols, esters of a $C_8$-$C_{30}$ fatty acid and of a Guerbet alcohol, fatty alcohol ethers comprising from 6 to 20 carbon atoms, and linear $C_7$-$C_{17}$ alkanes;

the weight amounts being given relative to the total weight of the anhydrous composite material.

According to another specific embodiment of the invention, the anhydrous composite material is formed from at least:
- from 3% to 15% by weight of at least one lipophilic gelling agent chosen from fatty acid esters of dextrin, preferably dextrin myristate;
- from 20% to 50% by weight and preferably from 40% to 50% by weight of at least one filler chosen from spherical cellulose particles; and
- from 40% to 85% by weight of at least one fatty phase containing at least 25% by weight of at least one oil chosen from hydrocarbon-based oils, preferably triglycerides;

the weight amounts being given relative to the total weight of the anhydrous composite material.

Preferably, the anhydrous composite material is formed from at least:
- from 3% to 15% by weight of at least one lipophilic gelling agent chosen from fatty acid esters of dextrin, preferably dextrin myristate;
- from 40% to 50% by weight of at least one filler chosen from spherical cellulose particles; and
- from 40% to 85% by weight of at least one fatty phase containing at least 40% by weight of at least one oil chosen from hydrocarbon-based oils, preferably triglycerides;

the weight amounts being given relative to the total weight of the anhydrous composite material.

According to another specific embodiment of the invention, the anhydrous composite material is formed from at least:
- from 3% to 15% by weight of at least one lipophilic gelling agent chosen from triesters of a fatty acid and of mono- or polyglycerol, such as glyceryl trihydroxystearate;
- from 20% to 50% by weight and preferably from 30% to 40% by weight of at least one filler chosen from spherical cellulose particles; and
- from 40% to 85% by weight of at least one fatty phase containing at least 25% by weight of at least one oil chosen from hydrocarbon-based oils, preferably triglycerides, Guerbet alcohols, esters of a $C_8$-$C_{30}$ fatty acid and of a Guerbet alcohol, fatty alcohol ethers comprising from 6 to 20 carbon atoms, and linear $C_7$-$C_{17}$ alkanes;

the weight amounts being given relative to the total weight of the anhydrous composite material.

According to another specific embodiment of the invention, the anhydrous composite material is formed from at least:
- from 3% to 15% by weight of at least one lipophilic gelling agent chosen from triesters of a fatty acid and of mono- or polyglycerol, such as glyceryl trihydroxystearate;
- from 20% to 50% by weight and preferably from 30% to 40% by weight of at least one filler chosen from spherical cellulose particles; and
- from 40% to 85% by weight of at least one fatty phase containing at least 25% by weight of at least two oils, one of which is chosen from hydrocarbon-based oils, preferably triglycerides, and the other is chosen from linear $C_7$-$C_{17}$ alkanes;

the weight amounts being given relative to the total weight of the anhydrous composite material.

Preferably, the anhydrous composite material is formed from at least:

from 3% to 15% by weight of at least one lipophilic gelling agent chosen from triesters of a fatty acid and of mono- or polyglycerol, such as glyceryl trihydroxystearate;

from 30% to 40% by weight of at least one filler chosen from spherical cellulose particles; and from 45% to 85% by weight of at least one fatty phase containing at least 25% by weight of at least one oil chosen from hydrocarbon-based oils, preferably triglycerides, and at least 20% by weight of at least one oil chosen from linear $C_7$-$C_{17}$ alkanes;

the weight amounts being given relative to the total weight of the anhydrous composite material.

According to another specific embodiment of the invention, the anhydrous composite material is formed from at least:

from 3% to 15% by weight of at least one lipophilic gelling agent chosen from fatty acid esters of dextrin, preferably dextrin palmitate;

from 20% to 50% by weight and preferably from 30% to 40% by weight of at least one filler chosen from spherical cellulose particles; and from 40% to 85% by weight of at least one fatty phase containing at least 25% by weight of at least one oil chosen from hydrocarbon-based oils, preferably triglycerides, Guerbet alcohols, esters of a $C_8$-$C_{30}$ fatty acid and of a Guerbet alcohol, fatty alcohol ethers comprising from 6 to 20 carbon atoms, and linear $C_7$-$C_{17}$ alkanes;

the weight amounts being given relative to the total weight of the anhydrous composite material.

According to another specific embodiment of the invention, the anhydrous composite material is formed from at least:

from 3% to 15% by weight of at least one lipophilic gelling agent chosen from fatty acid esters of dextrin, preferably dextrin palmitate;

from 20% to 50% by weight and preferably from 30% to 40% by weight of at least one filler chosen from spherical cellulose particles; and from 40% to 85% by weight of at least one fatty phase comprising at least 25% by weight of at least one oil chosen from Guerbet alcohols and esters of a $C_8$-$C_{30}$ fatty acid and of a Guerbet alcohol;

the weight amounts being given relative to the total weight of the anhydrous composite material.

Preferably, the anhydrous composite material is formed from at least:

from 3% to 15% by weight of at least one lipophilic gelling agent chosen from fatty acid esters of dextrin, preferably dextrin palmitate;

from 30% to 40% by weight of at least one filler chosen from spherical cellulose particles; and from 40% to 85% by weight of at least one fatty phase comprising at least 30% by weight of at least one oil chosen from Guerbet alcohols and esters of a $C_8$-$C_{30}$ fatty acid and of a Guerbet alcohol;

the weight amounts being given relative to the total weight of the anhydrous composite material.

Other Ingredients

It is understood that the aqueous phase of a composition according to the invention may comprise, besides the hydrophilic gelling agent and the dispersion of anhydrous composite material, other common cosmetic compounds.

The continuous aqueous phase may consist essentially of water, of hydrophilic gelling agent and of the dispersion of the anhydrous composite material. It may also comprise a water-miscible solvent (miscibility in water of greater than 50% by weight at 25° C.).

For example, the aqueous phase may contain one or more polyols comprising from 2 to 8 carbon atoms.

The term "polyol" should be understood as meaning any organic molecule comprising at least two free hydroxyl groups. Examples of polyols that may be mentioned include glycerol, glycols, for instance butylene glycol, propylene glycol, isoprene glycol, dipropylene glycol, hexylene glycol, polyethylene glycols and polypropylene glycol and especially dipropylene glycol, 1,2-propanediol and 1,3-propanediol.

According to a particular embodiment of the invention, the polyol is chosen from glycerol and 1,3-propanediol.

Preferably, the polyol is glycerol.

Examples that may be mentioned include the glycerol sold under the name Glycerine 4810 by the company Oleon or under the name Palmera G995V by the company KLK Oleo or alternatively under the name Refined Glycerine 99.5% PH. EURO by the company Cargill.

Mention may also be made of the 1,3-propanediol sold under the name Zemea Propanediol by the company Dupont Tate and Lyle Bio Products.

Mention may also be made of the butylene glycol sold under the name 1,3 Butylene Glycol by the company Alzo or alternatively Daicel.

Mention may also be made of the propylene glycol sold under the name Radianol 4710 by the company Oleon.

The amount of polyols may range, for example, from 0% to 20% by weight, especially from 0.1% to 20% by weight, preferably from 3% to 17% by weight, better still from 4% to 15% by weight and even better still from 5% to 10% by weight, relative to the total weight of the composition.

The composition in accordance with the invention may also comprise one or more primary alcohols, i.e. an alcohol comprising from 2 to 6 carbon atoms, such as ethanol, propanol, isopropanol, butanol, pentanol or hexanol, and in particular ethanol and isopropanol. It is preferably ethanol.

The addition of such an alcohol may especially be suitable when the composition according to the invention is used as a product for the body, the face or the hair.

The amount of primary alcohols may range, for example, from 0% to 35% by weight, especially from 0.1% to 35% by weight, preferably from 1% to 15% by weight and even more preferentially from 5% to 10% by weight, relative to the total weight of the composition.

Cosmetic Composition

Needless to say, the compositions according to the invention comprise a physiologically acceptable medium.

The term "physiologically acceptable medium" is intended to denote a medium that is particularly suitable for applying a composition of the invention to keratin materials, especially the skin and more particularly to facial skin, the lips and the nails. The physiologically acceptable medium is generally suited to the nature of the support onto which the product is to be applied.

They also contain ingredients usually selected for the formulation of cosmetic compositions intended for care and/or makeup.

Fatty Phase

Needless to say, a composition according to the invention may comprise a fatty phase different from that under consideration in the anhydrous composite material.

The compound(s) present in such a fatty phase may be chosen by a person skilled in the art on the basis of his general knowledge, so as to give the final composition the desired properties, especially in terms of rheological properties (penetrometry measurement, flow, consistency) or in terms of texture and stability.

For the purpose of the invention, the fatty phase includes any fatty substance that is liquid at room temperature and atmospheric pressure, generally oils, or that is solid at room temperature and atmospheric pressure, like waxes, or any pasty compound, especially as defined previously.

The fatty phase may be present in a composition according to the invention in an amount ranging from 0.1% to 30% by weight, better still ranging from 1% to 25% by weight and preferably from 2.5% to 20% by weight relative to the total weight of the composition.

Needless to say, this content does not comprise the fatty phase of the anhydrous composite material.

Adjuvants and Active Agents

The composition of the invention may also contain one or more adjuvants that are common in the cosmetic and dermatological fields, such as surfactants, moisturizers, hydrophilic or lipophilic active agents, free-radical scavengers, antioxidants, preserving agents, fragrances, film-forming agents, dyestuffs, such as nacres, reflective particles, pigments and/or dyes, and fillers, and mixtures thereof.

The composition in accordance with the invention may also comprise one or more active agents.

Nonlimiting examples of active agents that may be mentioned include ascorbic acid and derivatives thereof such as 5,6-di-O-dimethylsilyl ascorbate (sold especially by the company Exsymol under the reference PRO-AA), the potassium salt of dl-alpha-tocopheryl-2l-ascorbyl phosphate (sold especially by the company Senju Pharmaceutical under the reference Sepivital EPC), magnesium ascorbyl phosphate, sodium ascorbyl phosphate (sold especially by the company Roche under the reference Stay-C 50); phloroglucinol; enzymes; and mixtures thereof.

According to a preferred embodiment of the invention, use is made, among oxidation-sensitive hydrophilic active agents, of ascorbic acid. The ascorbic acid can be of any nature. Thus, it may be of natural origin in powder form or in the form of orange juice, preferably orange juice concentrate. It may also be of synthetic origin, preferably in powder form.

As other active agents that may be used in the composition of the invention, examples that may be mentioned include moisturizers, such as protein hydrolyzates; natural extracts; anti-inflammatories; oligomeric proanthocyanidins; vitamins such as vitamin A (retinol), vitamin E (tocopherol) and other antioxidants such as extract of rosemary, vitamin B5 (panthenol), vitamin B3 (niacinamide), derivatives of these vitamins (especially esters) and mixtures thereof; urea, caffeine, adenosine, depigmenting agents such as kojic acid, hydroquinone and caffeic acid; salicylic acid and derivatives thereof; alpha-hydroxy acids, such as lactic acid and glycolic acid and derivatives thereof; retinoids, such as carotenoids and vitamin A derivatives; hydrocortisone; melatonin; extracts of algae, of fungi, of plants, of yeasts, of bacteria; steroids; antibacterial active agents, matt-effect agents, for instance fibers; tensioning agents, UV-screening agents, essential oils, ceramides, and sodium hyaluronate, and mixtures thereof.

Preferably, a composition according to the invention also contains at least one active agent, preferably at least one sodium hyaluronate.

The amounts of these various adjuvants and/or active agents are those conventionally used in the fields under consideration. In particular, these amounts vary according to the desired aim and may range, for example, from 0.01% to 20% and preferably from 0.1% to 12% by weight relative to the total weight of the composition.

Needless to say, a person skilled in the art will take care to select the optional adjuvant(s) and/or active agent(s) added to the composition according to the invention such that the advantageous properties intrinsically associated with the composition in accordance with the invention are not, or are not substantially, adversely affected by the envisioned addition.

Presentation Form and Application

The composition according to the invention may be used for any topical application. In particular, it may constitute a cosmetic or dermatological composition, preferably a cosmetic composition, and in particular in the cosmetic field with immediate perceived efficacy.

It may in particular be used for caring for and/or removing makeup from the skin, the lips and/or the eyes, and also as a haircare composition. It may also be used as a deodorant or as an antisun product, and also for cleansing the skin.

The composition in accordance with the invention may especially be used as a product for cosmetic use for caring for the skin with regard to antiaging care, greasy skin, antisun protection, antiperspirants and deodorants, hair and/or scalp products, and also styling products, fragrancing products and makeup products.

A subject of the invention is also the cosmetic use of a composition as defined above, for caring for, removing makeup from and/or cleansing the skin, the lips and/or the eyes, and/or for haircare.

A subject of the present invention is also a cosmetic process for removing makeup from and/or caring for the skin, the lips and/or the eyes, in which a composition as defined above is applied to the skin, the lips and/or the eyes.

A subject of the present invention is also a cosmetic haircare process, in which a composition as defined above is applied to the hair.

A subject of the present invention is also a cosmetic treatment process for hiding skin color imperfections and/or skin relief imperfections.

According to a preferred embodiment of the invention, the composition is a composition for caring for bodily and/or facial skin, preferably facial skin.

A composition according to the invention may be in various presentation forms normally used in cosmetics.

A composition according to the invention is preferably in the form of a serum.

Throughout the description, including the claims, the term "comprising a" should be understood as being synonymous with "comprising at least one", unless otherwise specified.

The terms "between . . . and . . . " and "ranging from . . . to . . . " should be understood as being inclusive of the limits, unless otherwise specified.

The term "at least one" is equivalent to "one or more".

The invention is illustrated in greater detail by the examples described below, which are given as nonlimiting illustrations.

The percentages are weight percentages.

In the examples that follow, the weight percentages are indicated relative to the total weight of the material or of the composition.

EXAMPLES

Example I: Anhydrous Composite Materials

The various anhydrous composite materials 1 to 4 below in accordance with the invention are first prepared:

Anhydrous Composite Material 1

| Phase | Compounds | Composite material 1 (%) |
|---|---|---|
| A1 | Mixture of caprylic/capric acid triglycerides (70/30 $C_8C_{10}$ triglycerides - Dub MCT 7030 from Stearineries Dubois) | 46.00 |
|  | Candelilla wax (Candelilla Wax SP 75 G from Strahl & Pitsch) | 5.00 |
| A2 | Mixture based on undecane and tridecane (Cetiol UT from BASF) | 9.00 |
| A3 | Triester of glycerol and of hydroxystearic acid (Thixcin R from Elementis) | 5.00 |
| B1 | Porous silica microbeads (1-16 μm) (Silica, SB-300 Bead from Miyoshi Kasei) | 25.00 |
| B2 | Spherical cellulose beads (4-7 μm) (Cellulobeads USF from Daito Kasei Kogyo) | 10.00 |

Anhydrous Composite Material 2

| Phase | Compounds | Composite material 2 (%) |
|---|---|---|
| A1 | Mixture of caprylic/capric acid triglycerides (70/30 $C_8C_{10}$ triglycerides - Dub MCT 7030 from Stearineries Dubois) | 51.00 |
| A2 | Mixture based on undecane and tridecane (Cetiol UT from BASF) | 9.00 |
| A3 | Triester of glycerol and of hydroxystearic acid (Thixcin R from Elementis) | 5.00 |
| B1 | Porous silica microbeads (1-16 μm) (Silica, SB-300 Bead from Miyoshi Kasei) | 25.00 |
| B2 | Spherical cellulose beads (4-7 μm) (Cellulobeads USF from Daito Kasei Kogyo) | 10.00 |

Anhydrous Composite Materials 3 and 4

| Phase | Compounds | Composite material 3 (%) | Composite material 4 (%) |
|---|---|---|---|
| A1 | Mixture of caprylic/capric acid triglycerides (70/30 $C_8C_{10}$ triglycerides - Dub MCT 7030 from Stearineries Dubois) | 55.00 | 53.50 |
| A2 | Mixture based on undecane and tridecane (Cetiol UT from BASF) | 9.00 | 9.00 |
| A3 | Triester of glycerol and of hydroxystearic acid (Thixcin R from Elementis) | 6.00 | 7.50 |
| B1 | Cellulose (Cellulobeads D-5 from Kobo) | 5.00 | 5.00 |
| B2 | Spherical cellulose beads (4-7 μm) (Cellulobeads USF from Daito Kasei Kogyo) | 25.00 | 25.00 |

Preparation Process

The anhydrous composite materials 1 to 4 were obtained according to the following protocol:

Phase A1 is heated to a temperature of 75-80° C. with a deflocculator. The mixture is left at 75-80° C. for a minimum of 15 minutes until a homogenization is complete (total dissolution).

The mixture is cooled to 50° C. During the cooling, at 70° C., phase A2 is added. At 50° C., phase A3 is then dispersed in the mixture of phases A1 and A2. The mixture is stirred for 10 minutes at 3300 rpm.

The mixture is then transferred into a kneader with a flexible anchor, the tank being preheated to 50° C.

Half of phase B1 is then added, and the mixture is stirred for 3 minutes at minimum speed 1 (Kenwood "Chef Titanium" machine).

The other half of phase B1 is then added, and the mixture is stirred for 3 minutes at minimum speed 1.

Half of phase B2 is then added and the mixture is stirred for 1 minute at minimum speed 1.

The other half of phase B2 is then added, and the mixture is stirred for 2 minutes 30 seconds at minimum speed 1.

The mixture is then stirred at minimum speed 1 and manual scraping is performed. The mixture is then stirred for 3 minutes at medium speed 3-4 and manual scraping is again performed. Finally, the mixture is stirred for 2 minutes at high speed 6. In parallel, the mixture is cooled in a water bath at 20° C., down to a temperature below 30° C.

To finish, manual scraping is again performed and the mixture is then stirred for 5 minutes at high speed 6 and then for 2 minutes at low speed 1-2.

Example II: Care Compositions

Care compositions 1 to 4 below in accordance with the invention are prepared.

Care Composition 1

| Phase | Compounds | Composition 1 (%) |
|---|---|---|
| A | Water | 25.00 |
|  | Cellulose, microcrystalline cellulose and cellulose gum (Natpure Cellgum Plus from Sensient) | 1.00 |
|  | Glycerol | 3.00 |
| B | Water | 52.85 |
|  | Adenosine (Adenosine 0909 from Cheng Yi Pharmaceutical) | 0.10 |
|  | Powdered potassium sorbate | 0.13 |
| C | Iota-carrageenan (Genuvisco Carrageenan CG-131 from CP Kelco) | 0.48 |
|  | Xanthan gum (Rhodicare XC from Rhodia (Solvay)) | 0.10 |
|  | 1,3-Propanediol (Zemea Propanediol from DuPont Tate and Lyle Bioproducts) | 3.00 |

-continued

| Phase | Compounds | Composition 1 (%) |
|---|---|---|
| D | Methyl glucoside sesquistearate (Mono/Di-Tri Ester 40/22) (Glucate SS Emulsifier from Lubrizol) | 0.10 |
| | Mixture based on undecane and tridecane (Cetiol UT from BASF) | 1.00 |
| E | Glyceryl caprylate | 0.50 |
| F | Sodium hyaluronate (MW: 1 100 000) powder (Cristalhyal LO from Soliance) | 0.60 |
| G | Anhydrous composite material 1 | 1.50 |
| H | Water | 3.00 |
| | Plant extract | 1.50 |
| I | Ethyl alcohol | 5.15 |
| | Fragrance | 0.20 |
| J | Citric acid | 0.16 |
| | Water | 0.63 |

Care Compositions 2 to 4

| Phase | Compounds | Composition 2 (%) | Composition 3 (%) | Composition 4 (%) |
|---|---|---|---|---|
| A | Water | 70.64 | 71.14 | 71.64 |
| | Cellulose, microcrystalline cellulose and cellulose gum (Natpure Cellgum Plus from Sensient) | 1.00 | 1.00 | 1.00 |
| | Glycerol | 3.00 | 3.00 | 3.00 |
| B | Water | 5.00 | 5.00 | 5.00 |
| | Adenosine (Adenosine 0909 from Cheng Yi Pharmaceutical) | 0.10 | 0.10 | 0.10 |
| | Powdered potassium sorbate | 0.13 | 0.13 | 0.13 |
| C | Iota-carrageenan (Genuvisco Carrageenan CG-131 from CP Kelco) | 0.48 | 0.48 | 0.48 |
| | Xanthan gum (Rhodicare XC from Rhodia (Solvay)) | 0.10 | 0.10 | 0.10 |
| | 1,3-Propanediol (Zemea Propanediol from DuPont Tate and Lyle Bioproducts) | 3.00 | 3.00 | 3.00 |
| D | Methyl glucoside sesquistearate (Mono/Di-Tri Ester 40/22) (Glucate SS Emulsifier from Lubrizol) | 0.10 | 0.10 | 0.10 |
| | Mixture based on undecane and tridecane (Cetiol UT from BASF) | 1.00 | 1.00 | 1.00 |
| E | Glyceryl caprylate | 0.50 | 0.50 | 0.50 |
| F | Sodium hyaluronate (MW: 1 100 000) powder (Cristalhyal LO from Soliance) | 0.60 | 0.60 | 0.60 |
| G | Anhydrous composite material 1 | 2.50 | 2.00 | 1.50 |
| H | Water | 5.00 | 5.00 | 5.00 |
| | Plant extract | 1.50 | 1.50 | 1.50 |
| | Sodium Phytate (Dermofeel PA-3 from Dr Straetmans) | 0.15 | 0.15 | 0.15 |
| I | Ethyl alcohol | 5.00 | 5.00 | 5.00 |
| | Fragrance | 0.20 | 0.20 | 0.20 |

Preparation Process

Compositions 1 to 4 were obtained according to the following protocol:

The ingredients of phase A are mixed for 20 minutes with a rotor-stator at a speed of 3300 rpm at room temperature (between 25° C. and 30° C.).

Phase B is added with rotor-stator stirring at a speed of 2000 rpm.

The mixture is then heated to a temperature equal to 65° C. During the temperature increase, phase C is added with rotor-stator stirring at a speed of 3300 rpm.

In parallel, phase D is heated on a water bath to 65° C. It is added immediately to the preceding mixture with rotor-stator stirring at a speed of 3300 rpm over 6 minutes.

The mixture is cooled. During the cooling, at a temperature of between 50° C. and 60° C., phase E is added.

Cooling is performed with paddle stirring at a speed of 150 rpm down to a temperature equal to 30° C.

The mixture is kept at a temperature below 30° C., and phase F is added with rotor-stator stirring at a speed of 3300 rpm over 15 minutes.

Phase G containing the anhydrous composite material 1 is added to the preceding mixture at a temperature of 25° C. Once the anhydrous composite material 1 disperses correctly, the mixture is stirred at room temperature (between 25° C. and 30° C.) for 5 minutes with rotor-stator stirring at a speed of between 3000 and 3300 rpm. It is checked that the anhydrous composite material 1 does not agglomerate on the walls of the container, the base or the paddles. Where appropriate, additional stirring for 2 to 3 minutes is performed, the total stirring time not exceeding 8 minutes. The anhydrous composite material 1 is visible in suspension by microscope.

Phases H and I are added to the mixture with stirring at a speed of 200 rpm.

Finally, the mixture is stirred with a rotor-stator for 1 minute at a speed of 2500 rpm.

The compositions according to the invention have a soft, smooth texture. They leave a light, fresh, soft, silky and smooth finish after application to the skin. Furthermore, they are easy to apply and penetrate quickly into the skin.

Example III: Composition not in Accordance with the Invention

Composition 5 below not in accordance with the invention is prepared.

Composition 5 not in Accordance with the Invention

| Phase | Compounds | Composition 5 (%) |
|---|---|---|
| A | Water | 70.97 |
|   | Cellulose, microcrystalline cellulose and cellulose gum (Natpure Cellgum Plus from Sensient) | 1.00 |
|   | Glycerol | 3.00 |
| B | Water | 5.00 |
|   | Adenosine (Adenosine 0909 from Cheng Yi Pharmaceutical) | 0.10 |
|   | Powdered potassium sorbate | 0.13 |
| C | Iota-carrageenan (Genuvisco Carrageenan CG-131 from CP Kelco) | 0.48 |
|   | Xanthan gum (Rhodicare XC from Rhodia (Solvay)) | 0.10 |
|   | 1,3-Propanediol (Zemea Propanediol from DuPont Tate and Lyle Bioproducts) | 3.00 |
| D | Methyl glucoside sesquistearate (Mono/Di-Tri Ester 40/22) (Glucate SS Emulsifier from Lubrizol) | 0.10 |
|   | Mixture based on undecane and tridecane (Cetiol UT from BASF) | 1.00 |
| E | Glyceryl caprylate | 0.50 |
| F | Sodium hyaluronate (MW: 1 100 000) powder (Cristalhyal LO from Soliance) | 0.60 |
| G | Porous silica microbeads (1-16 µm) (Silica, SB-300, Bead from Miyoshi Kasei) | 0.38 |
|   | Spherical cellulose beads (4-7 µm) (Cellulobeads USF from Daito Kasei Kogyo) | 0.15 |
| H | Water | 5.00 |
|   | Plant extract | 1.50 |
| I | Ethyl alcohol | 5.00 |
|   | Fragrance | 0.20 |
| J | Citric acid | 0.79 |
|   | Water | 1.00 |

Preparation Process

Composition 5 not in accordance with the invention is characterized in that it does not contain any anhydrous composite material prepared beforehand. Various fillers are added to the composition individually.

Composition 5 was obtained according to the following protocol:

The ingredients of phase A are mixed for 20 minutes with rotor-stator stirring at a speed of 3300 rpm at room temperature.

Phase B is added to phase A with rotor-stator stirring at a speed of 1400 rpm. The mixture is then heated to a temperature equal to 65° C.

During the temperature increase, at about 40° C., phase C is added with rotor-stator stirring at a speed of 3300 rpm.

In parallel, phase D is heated on a water bath to 65° C. It is added immediately to the preceding mixture with rotor-stator stirring at a speed of 3300 rpm over 6 minutes.

The mixture is cooled. During the cooling, at a temperature of between 50° C. and 60° C., phase E is added.

Cooling is performed with paddle stirring down to a temperature equal to 30-35° C.

The mixture is kept at a temperature below 30° C. using a bath of cold water, and phase F is added with rotor-stator stirring at a speed of 3300 rpm over 15 minutes.

Phase G is then added to the mixture at a temperature of 25° C., followed by phase H, with rotor-stator stirring for 5 minutes.

Phases I and J are added to the mixture with paddle stirring.

Finally, the pH of the mixture is adjusted to a pH of 4.8±0.2.

Composition 1 according to the invention and composition 5 not in accordance with the invention were compared. 16 women from 30 to 65 years old, having wrinkles and fine lines, and who are daily users of facial antiaging composition, applied each of the two compositions to the face for 7 days.

The effect on the visibility of the wrinkles is evaluated according to the Chromasphere® evaluation.

The Chromasphere® evaluation makes it possible to evaluate the effects on the visibility of wrinkles and also on the homogeneity and color of the complexion.

Principle

Chromosphere® is an imaging platform for acquiring, under diffuse daylight illumination, calibrated color images (profile).

Analysis of the images makes it possible to obtain parameters Ra and Rz, by using the software Visibility 1.4.4 for evaluation of the effects on the visibility of wrinkles. It also makes it possible to obtain homogeneity parameters (ICOX) and color parameters (L*, a*, b* and delta E), using the software Chromalys pro 1.5 for evaluation of the homogeneity and color of the complexion.

Application of the Products

Each half-face of a face receives 300 mg of cosmetic composition (mg-µL equivalence established after three weighings). The choice of each half-face is made randomly according to a table established by the instruction center.

The technician in charge applies the compositions to each half-face, beginning with the forehead and going down to the chin in small deposits. He spreads the composition via movements from the center to the outer parts of the face, using four fingers, first on the forehead, then on the eye and the forehead, and finally on the lower part of the face.

Marking-Out of the Images

An image of each half-face chosen at random (randomization performed initially on 24 individuals so as to be equilibrated) is taken by the technician in charge. The images are taken at t=0 and at t=10 minutes.

Evaluation of the Effect on the Visibility of the Wrinkles

For the evaluation of the effect on the visibility of the wrinkles, the parameters obtained are Ra which represents the mean deviation of the side view along a median line, and Rb which represents the mean roughness.

Results

The results are expressed for each parameter:

- as a mean value, minimum, maximum and average standard deviation for each experimental time (t=0 and t=10 minutes),
- as a percentage of variation of the means at t=10 minutes relative to t=0 [mean variables %=((mean t=10 minutes−mean t=0)/(mean t=0))×100],
- as a mean value, minimum, maximum and average standard deviation for the difference (t=10 minutes−t=0).

Composition 1 makes it possible to further reduce the appearance of the wrinkles and fine lines when compared with composition 5. In addition, it was noted that composition 1 made it possible to give the facial skin a smoother appearance, compared with composition 5.

Example IV: Care Compositions

Care compositions 6 to 11 below in accordance with the invention are prepared.
Care Compositions 6 to 11

| Phase | Compounds | Composition 6 (%) | Composition 7 (%) | Composition 8 (%) | Composition 9 (%) | Composition 10 (%) | Composition 11 (%) |
|---|---|---|---|---|---|---|---|
| A1 | Water | 20.00 | 20.00 | 20.00 | 20.00 | 20.00 | 20.00 |
|  | Glycerol | 5.00 | 5.00 | 5.00 | 5.00 | 5.00 | 5.00 |
|  | Adenosine (Adenosine 0909 from Cheng Yi Pharmaceutical) | 0.10 | 0.10 | 0.10 | 0.10 | 0.10 | 0.10 |
|  | PEG-20 methyl glucoside sesquistearate (Glucamate SSE-20 Emulsifier from Lubrizol) | 0.20 | 0.20 | 0.20 | 0.20 | 0.20 | 0.20 |
|  | Caprylyl glycol | 0.30 | 0.30 | 0.30 | 0.30 | 0.30 | 0.30 |
|  | Phenoxyethanol | 0.50 | 0.50 | 0.50 | 0.50 | 0.50 | 0.50 |
|  | Disodium EDTA (EDETA BD from BASF) | 0.10 | 0.10 | 0.10 | 0.10 | 0.10 | 0.10 |
| A2 | Water | 33.03 | 40.65 | 45.65 | 43.15 | 33.03 | 33.03 |
| A3 | Bifida Ferment Lysate (Repair Complex CLR PF from CLR) | 10.00 | 10.00 | 10.00 | 10.00 | 10.00 | 10.00 |
| B | Sodium hyaluronate (Cristalhyal LO from Soliance) | 0.20 | 0.20 | 0.20 | 0.20 | 0.20 | 0.20 |
|  | Ammonium polyacryloyldimethyl taurate (Hostacerin AMPS from Clariant) | 0.40 | 0.40 | 0.40 | 0.40 | 0.40 | 0.40 |
|  | Xanthan gum (Keltrol CG-T from CP Kelco) | 0.20 | 0.20 | 0.20 | 0.20 | 0.20 | 0.20 |
| C | Water | 5.00 | 5.00 | 5.00 | 5.00 | 5.00 | 5.00 |
|  | Sodium hydroxide (Sodium hydroxide from PT Sulfindo Adiusaha) | 0.05 | 0.05 | 0.05 | 0.05 | 0.05 | 0.05 |
|  | Yeast extract (Firmalift GR from Silab) | 1.00 | / | / | / | 1.00 | 1.00 |
| D | Ethyl alcohol | 5.00 | 5.00 | 5.00 | 5.00 | 5.00 | 5.00 |
|  | Capryloyl salicylic acid (Mexoryl SAB from Chimex) | 0.30 | 0.30 | 0.30 | 0.30 | 0.30 | 0.30 |
|  | Octyldodecanol | 0.50 | 0.50 | 0.50 | 0.50 | 0.50 | 0.50 |
|  | Fragrance | 0.12 | / | / | / | 0.12 | 0.12 |
| E | Dimethicone (Belsil DM 100 from Wacker) | 1.00 | 1.00 | 1.00 | 1.00 | 1.00 | 1.00 |
|  | BIS-PEG/PPG-16/16 PEG/PPG-16/16 Dimethicone and mixture of caprylic/capric acid triglycerides (Abil Care 85 from Evonik Goldschmidt) | 0.50 | 0.50 | 0.50 | 0.50 | 0.50 | 0.50 |
| F | Anhydrous composite material 2 | 16.50 | 10.00 | 5.00 | 7.50 | / | / |
|  | Anhydrous composite material 3 | / | / | / | / | 16.5 | / |
|  | Anhydrous composite material 4 | / | / | / | / | / | 16.5 |

Preparation Process

Compositions 6 to 11 were obtained according to the following protocol:

A temperature of 35° C. is maintained during the preparation process.

The ingredients of phase A1 are dispersed with a deflocculator for homogenization, and then mixed for 5 minutes with rotor-stator stirring at a speed of 400 rpm.

Phase A2 and then phase A3 are added, and then mixed with rotor-stator stirring at a speed of 1300 rpm for 5 minutes.

Phase B is premixed with a spatula, and then introduced very carefully into the mixture. The mixture is kept stirring for 10 minutes at a speed of 3300 rpm, in a bath of cold water to avoid an excessive temperature increase (ice cubes are gradually added to the water bath).

Phase C is added with rotor-stator stirring at a speed of 3300 rpm. The mixture is kept stirring for 5 minutes.

The stirring speed is reduced to 1500 rpm to cool the mixture down to a temperature below 30° C.

Phase D is premixed until the ingredients have fully dissolved, and is then added to the mixture with rotor-stator stirring at a speed of 3300 rpm over 5 minutes.

Phase E is added with a deflocculator. The mixture is kept stirring at a speed of 3300 rpm for 5 minutes.

Phase F containing the anhydrous composite material is added to the preceding mixture at a temperature of 25° C. The mixture is stirred with a rotor-stator for 5 minutes at a speed of 3300 rpm, so as to fully disperse the anhydrous composite material without emulsifying it. After 2 minutes of stirring, it is checked that there are no lumps of anhydrous composite material stuck in the rotor. The anhydrous composite material in the form of lumps in suspension is visible by microscope.

Finally, the pH of the mixture is adjusted to a pH of 5.8±0.3.

The compositions were tested, especially by means of the Chromasphere evaluation as described previously.

The compositions according to the invention make it possible to reduce the skin sheen, and induce a reduction in the visibility of the pores. The dryness striations, wrinkles and fine lines are attenuated, especially for the wrinkles under the eyes. The visibility of the dyschromia (redness and shadows) is also reduced.

Example V: Composition not in Accordance with the Invention

Composition 12 below not in accordance with the invention is prepared.
Composition 12 not in Accordance with the Invention

| Phase | Compounds | Composition 12 (%) |
|---|---|---|
| A1 | Water | 20.00 |
|  | Glycerol | 5.00 |

-continued

| Phase | Compounds | Composition 12 (%) |
|---|---|---|
|  | Adenosine (Adenosine 0909 from Cheng Yi Pharmaceutical) | 0.10 |
|  | PEG-20 methyl glucose sesquistearate (Glucamate SSE-20 Emulsifier from Lubrizol) | 0.20 |
|  | Caprylyl glycol | 0.30 |
|  | Phenoxyethanol | 0.50 |
|  | Disodium EDTA (EDETA BD from BASF) | 0.10 |
| A2 | Water | 33.03 |
| A3 | Bifida Ferment Lysate (Repair Complex CLR PF from CLR) | 10.00 |
| B | Sodium hyaluronate (Cristalhyal LO from Soliance) | 0.20 |
|  | Ammonium polyacryloyldimethyl taurate (Hostacerin AMPS from Clariant) | 0.40 |
|  | Xanthan gum (Rhodicare XC from Rhodia (Solvay)) | 0.20 |
| C | Yeast extract (Firmalift GR from Silab) | 1.00 |
| D | Water | 5.00 |
|  | Sodium hydroxide (Sodium hydroxide from PT Sulfindo Adiusaha) | 0.05 |
| E1 | Ethyl alcohol | 5.00 |
|  | Caprylyl salicylic acid (Mexoryl SAB from Chimex) | 0.30 |
|  | Octyldodecanol | 0.50 |
|  | Fragrance | 0.12 |
| E3 | Dimethicone (Belsil DM 100 from Wacker) | 1.00 |
|  | Polysilicone-11 (Gransil RPS-D6 from Grant Industries) | 15.00 |
|  | BIS-PEG/PPG-16/16 PEG/PPG-16/16 Dimethicone and mixture of caprylic/capric acid triglycerides (Abil Care 85 from Evonik Goldschmidt) | 0.50 |
|  | Polymethylsilsesquioxane (Tospearl 2000 B - Momentive Performance Materials) | 1.50 |

Preparation Process

Composition 12 not in accordance with the invention does not comprise the compounds of the anhydrous composite material, whether they are intimately mixed beforehand or added individually. Instead, it comprises silicone polymers such as polysilicone-11 and polymethylsilsesquioxane.

Composition 12 was obtained according to the following protocol:

A temperature of 35° C. is maintained during the preparation process.

The ingredients of phase A1 are dispersed with a deflocculator for homogenization, and then mixed for 5 minutes with rotor-stator stirring at a speed of 400 rpm.

Phase A2 and then phase A3 are added, and then mixed with rotor-stator stirring at a speed of 1300 rpm for 5 minutes.

Phase B is premixed with a spatula, and then introduced very carefully into the mixture. The mixture is kept stirring for 10 minutes at a speed of 3300 rpm, in a bath of cold water to avoid an excessive temperature increase (ice cubes are gradually added to the water bath).

Phase C is added with rotor-stator stirring at a speed of 3300 rpm. The mixture is kept stirring for 5 minutes.

Phase D is added with rotor-stator stirring at a speed of 3300 rpm. The mixture is kept stirring for 5 minutes.

The stirring speed is reduced to 1500 rpm to cool the mixture down to a temperature below 30° C.

Phase E1 is premixed until the ingredients have fully dissolved.

Phase E2 is also premixed.

Phases E1 and E2 are mixed with a deflocculator until homogeneous.

Phase E3 is dispersed in the mixture of phases E1 and E2 with a deflocculator.

The mixture of phases E1, E2 and E3 is added to the preceding mixture of phases A to D with rotor-stator stirring at a speed of 3300 rpm over a maximum of 2 minutes.

Finally, the pH of the mixture is adjusted to a pH of 5.8±0.3.

The optical properties of compositions 6 to 9 according to the invention were compared with those of composition 12 not in accordance with the invention, by means of the Haze measurement (veil effect) with a commercial Hazemeter machine.

The measurements were taken according to the following protocol: on a transparent plastic film (Byk), a coat with a wet thickness of 25.4 µm of the composition whose haze it is desired to evaluate is spread out, using an automatic spreader. The coat is left to dry for 1 hour at room temperature, and measurement of the haze index is then taken using a Byk Gardner brand Haze-gard.

The measurements taken show that the compositions in accordance with the invention make it possible to obtain a much larger soft-focus effect when compared with composition 12.

The invention claimed is:

1. Composition, different from cosmetic compositions comprising interpenetrated gelled aqueous phase and gelled lipophilic phase, comprising at least one aqueous phase containing at least:
   a hydrophilic gelling agent; and
   a dispersion of at least one anhydrous composite material formed from at least:
      3% to 15% by weight of at least one lipophilic gelling agent, said lipophilic gelling agent(s) being chosen from $C_8$-$C_{30}$ fatty acid esters of dextrin and triesters of a $C_8$-$C_{30}$ fatty acid and of mono- or polyglycerol, relative to the total weight of the material;
      10% to 50% by weight of fillers, said filler(s) being chosen from spherical cellulose particles, powders of an N-acylamino acid bearing a $C_8$-$C_{22}$ acyl group, and polyamide particles, porous spherical silica particles and mixtures thereof, relative to the total weight of the material; and
      40% to 85% by weight of at least one fatty phase, relative to the total weight of the material,
   said anhydrous composite material being present in particulate form in the aqueous phase, and wherein said anhydrous composite material possesses its own composition, does not decompose and maintains the independent properties of the anhydrous composite material.

2. Composition according to claim 1, wherein the aqueous phase is present in a content at least equal to 40% by weight, relative to the total weight of the composition.

3. Composition according to claim 1, comprising from 0.01% to 10% by weight, of hydrophilic gelling agent(s), relative to the total weight of the composition.

4. Composition according to claim 1, wherein the hydrophilic gelling agent is chosen from synthetic polymeric gelling agents, polymeric gelling agents that are natural or of natural origin, mixed silicates and fumed silicas, and mixtures thereof.

5. Composition according to claim 1, wherein the hydrophilic gelling agent is chosen from polysaccharides, and non-particulate synthetic polymeric gelling agents, and mixtures thereof.

6. Composition according to claim 1, wherein the hydrophilic gelling agent is chosen from xanthans, galactans, celluloses and derivatives thereof, and 2-acrylamido-2-methylpropanesulfonic acid polymers and copolymers, and mixtures thereof.

7. Composition according to claim 1, comprising from 0.1% to 30% by weight of anhydrous composite material, relative to the total weight of the composition.

8. Composition according to claim 1, comprising a weight ratio of anhydrous composite material/hydrophilic gelling agent(s) ranging from 0.2 to 30.

9. Composition according to claim 1, wherein the lipophilic gelling agent(s) of the anhydrous composite material are chosen from mono- or polyesters of dextrin and of at least one fatty acid corresponding to formula (C):

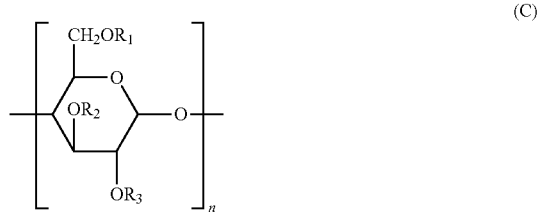

(C)

in which:
n is an integer ranging from 3 to 150; and
the radicals $R_1$, $R_2$ and $R_3$ represent a hydrogen atom or an acyl group (R—CO—) in which the radical R is a linear or branched, saturated or unsaturated hydrocarbon-based group containing from 6 to 50, with the proviso that at least one of said radicals $R_1$, $R_2$ or $R_3$ is other than a hydrogen atom.

10. Composition according to claim 1, wherein the mono- or polyesters of dextrin and of at least one fatty acid correspond to formula (C) in which:
n advantageously ranges from 25 to 35; and
the radical R—CO— is chosen from caprylyl, caproyl, lauroyl, myristyl, palmityl, stearyl, eicosanyl, docosanoyl, isovaleryl, 2-ethylbutyryl, ethylmethylacetyl, isoheptanyl, 2-ethylhexanyl, isononanyl, isodecanyl, isotridecanyl, isomyristyl, isopalmityl, isostearyl, isohexanyl, decenyl, dodecenyl, tetradecenyl, myristyl, hexadecenoyl, palmitoleyl, oleyl, elaidyl, eicosenyl, sorbyl, linoleyl, linolenyl, punicyl, arachidonyl and stearolyl radicals, and mixtures thereof.

11. Composition according to claim 1, wherein the lipophilic gelling agent(s) of the anhydrous composite material are chosen from triesters of a $C_8$-$C_{30}$ fatty acid and of monoglycerol.

12. Composition according to claim 1, wherein the anhydrous composite material is formed from at least 20% to 50% by weight of fillers, relative to the total weight of the material.

13. Composition according to claim 1, wherein the anhydrous composite material comprises at least two different fillers.

14. Composition according to claim 1, wherein the anhydrous composite material comprises at least two fillers that are different from each other, one of which is chosen from spherical cellulose particles, powders of an N-acylamino acid bearing a $C_8$-$C_{22}$ acyl group, and polyamide particles, and the other is chosen from spherical cellulose particles and porous spherical silica particles.

15. Composition according to claim 14, wherein the anhydrous composite material comprises at least two fillers that are different from each other, one of which is chosen from spherical cellulose particles and the other is chosen from porous spherical silica particles.

16. Composition according to claim 14, wherein the anhydrous composite material comprises at least two fillers that are different from each other, one of which is chosen from powders of an N-acylamino acid bearing a $C_8$-$C_{22}$ acyl group and the other is chosen from porous spherical silica particles.

17. Composition according to claim 14, wherein the anhydrous composite material comprises at least two fillers that are different from each other, the two being chosen from spherical cellulose particles.

18. Composition according to claim 1, wherein the anhydrous composite material is formed from at least 45% to 85% by weight of a fatty phase relative to the total weight of the material.

19. Composition according to claim 1, wherein the fatty phase of the anhydrous composite material comprises at least one oil.

20. Composition according to claim 1, wherein the fatty phase of the anhydrous composite material comprises at least one oil chosen from hydrocarbon-based oils, Guerbet alcohols, esters of a $C_8$-$C_{30}$ fatty acid and of a Guerbet alcohol, fatty alcohol ethers comprising from 6 to 20 carbon atoms, and linear $C_7$-$C_{17}$ alkanes, and mixtures thereof.

21. Composition according to claim 1, wherein the fatty phase of the anhydrous composite material comprises at least two different oils.

22. Composition according to claim 1, wherein the fatty phase of the anhydrous composite material also comprises at least one wax.

23. Composition according to claim 1, wherein the anhydrous composite material is formed from at least:
3% to 15% by weight, relative to the total weight of the material, of at least one lipophilic gelling agent chosen from triesters of a $C_8$-$C_{30}$ fatty acid and of mono- or polyglycerol;
10% to 50% by weight of fillers, relative to the total weight of the material, including at least 5% by weight of a first filler chosen from porous spherical silica microparticles and spherical cellulose particles, and at least 5% by weight of a second filler different from the first, chosen from spherical cellulose particles; and
40% to 85% by weight of at least one fatty phase, relative to the total weight of the material, comprising from 25% to 58% by weight, relative to the total weight of the material, of at least one oil chosen from hydrocarbon-based oils, and from 5% to 10% by weight of at least one oil chosen from linear $C_7$-$C_{17}$ alkanes.

24. Composition according to claim 1, wherein the anhydrous composite material is formed from at least:
3% to 15% by weight, relative to the total weight of the material, of at least one lipophilic gelling agent chosen from triesters of a $C_8$-$C_{30}$ fatty acid and of mono- or polyglycerol;
10% to 50% by weight of fillers, relative to the total weight of the material, including at least 5% by weight of a first filler chosen from porous spherical silica microparticles, and at least 5% by weight of a second filler chosen from spherical cellulose particles; and
40% to 85% by weight of at least one fatty phase, relative to the total weight of the material, comprising from 25% to 55% by weight, relative to the total weight of the material, of at least one oil chosen from hydrocarbon-based oils, from 5% to 10% by weight of at least one oil chosen from linear $C_7$-$C_{17}$ alkanes, and from 3% to 10% by weight of a wax.

25. Composition according to claim 1, containing at least one active agent.

26. Cosmetic process for making up and/or caring for a keratin material, comprising at least one step that consists in applying to said keratin material a composition as defined according to claim 1.

27. Composition, different from cosmetic compositions comprising interpenetrated gelled aqueous phase and gelled lipophilic phase, comprising at least one aqueous phase containing at least:
- a hydrophilic gelling agent, said hydrophilic gelling agent is at least chosen from polymeric gelling agents that are natural or of natural origin;
- a dispersion of at least one anhydrous composite material formed from at least:
- 3% to 15% by weight of at least one lipophilic gelling agent, said lipophilic gelling agent(s) being chosen from at least triesters of a C8-C30 fatty acid and of monoglycerol, relative to the total weight of the material;
- 10% to 50% by weight of fillers, said filler(s) being chosen from spherical cellulose particles, powders of an N-acylamino acid bearing a C8-C22 acyl group, and polyamide particles, porous spherical silica particles and mixtures thereof, relative to the total weight of the material; and
- 40% to 85% by weight of at least one fatty phase, relative to the total weight of the material, said anhydrous composite material being present in particulate form in the aqueous phase, and wherein said anhydrous composite material possesses its own composition, does not decompose and maintains the independent properties of the anhydrous composite material.

\* \* \* \* \*